(12) United States Patent
Prakash et al.

(10) Patent No.: US 6,921,812 B1
(45) Date of Patent: Jul. 26, 2005

(54) METHODS OF MODULATING PHARMACOKINETICS OF OLIGONUCLEOTIDES

(75) Inventors: Thazha P. Prakash, Carlsbad, CA (US); Muthiah Manoharan, Weston, MA (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 356 days.

(21) Appl. No.: 10/058,740

(22) Filed: Jan. 28, 2002

Related U.S. Application Data

(63) Continuation-in-part of application No. 09/932,898, filed on Aug. 20, 2001, now abandoned.
(60) Provisional application No. 60/302,683, filed on Jul. 3, 2001.

(51) Int. Cl.[7] .......................... C07H 21/00; C07H 21/02; C07H 21/04
(52) U.S. Cl. ...................... 536/23.1; 536/24.3; 536/25.3
(58) Field of Search .............................. 536/23.1, 24.3, 536/25.3

(56) References Cited

U.S. PATENT DOCUMENTS

| | | | |
|---|---|---|---|
| 5,149,798 A | 9/1992 | Agrawal et al. | 536/27 |
| 5,539,082 A | 7/1996 | Nielsen et al. | 530/300 |
| 6,147,200 A | 11/2000 | Manoharan et al. | 536/23.1 |
| 6,239,272 B1 | 5/2001 | Beigelman et al. | 536/24.5 |

FOREIGN PATENT DOCUMENTS

| | | |
|---|---|---|
| WO | 92/20702 | 11/1992 |
| WO | 92/20703 | 11/1992 |
| WO | 93/12129 | 6/1993 |

OTHER PUBLICATIONS

Manoharan et al. Bioorganic & Medicinal Chemistry Letters 1993, 3(12) 2765–70.*
Copy of the PCT International Search Report dated May 2, 2003 (PCT/US02/20940).
Prakash, T.P., et al., 2'-O-[2-(methylthio)ethyl]-modified oligonucleotide: an analogue of 2'-O-[2-(methoxy)-ethyl]-modified oligonucleotide with improved protein binding properties and high binding affinity to target RNA, *Biochemistry*, 2002, 41, 11642–11648.
U.S. Appl. No. 09/115,043, filed Jul. 14, 1998, Manoharan et al.
Anklam, E. et al., "Pulse Radiolytic Studies of 1–Halo–2–(methylthio)ethanes in Hexane and 1,2–Dichlorethane: Formation of an Intermolecular Species with a Three–Electron Bond between Sulfur and Iodine", *Helv. Chim. Acta*, 1987, 70, 2110–2117.
Baker, A. D. et al., "Ultra long–range through–bond interactions in dithiaspirane disulfoxides as revealed by photoelectron spectroscopy", *Tetrahedron Lett.*, 1983, 24(29), 2957–2960.

(Continued)

*Primary Examiner*—Jezia Riley
(74) *Attorney, Agent, or Firm*—Isis Patent Department; Woodcock Washburn LLP

(57) ABSTRACT

2'-O-(2-Methylthioethyl), has been incorporated into oligonucleotides and evaluated for antisense properties in comparison with the known 2'-O-(2-methoxyethyl) 2'-O-MOE modification. The 2'-O-MTE modified oligonucleotides exhibit improved binding to human serum albumin compared with the 2'-O-MOE modified oligonucleotides and maintain high binding affinity to target RNA.

28 Claims, 28 Drawing Sheets

OTHER PUBLICATIONS

Bannwarth, W., "Synthesis of Oligodeoxynucleotides by the Phosphite–Triester Method Using Dimer Units and Different Phosphorous–Protecting Groups," *Helvetica Chim. Acta*, 1985, 68, 1907–1913.

Bayer, E. et al., "Improved Conditions for Solid Phase Synthesis for Oligonucleotides on PS–PEG Copolymers," *Z. Naturforsch*, 1995, 50b, 1096–1100.

Beaucage, S. L. et al., "Deoxynucleoside Phosphoramidites—A New Class of Key Intermediates for Deoxypolynucleotide Synthesis," *Tetrahedron Letts.*, 1981, 22(20), 1859–1862.

Beaudry et al., "Determination of drug–plasma protein binding using human serum albumin chromatographic column and multiple linear regression model," *Biomed. Chromatogr.*, 1999, 13, 401–406.

Divakar, K. J. et al., "4–(1,2,4–Triazol–1–ly)–and 4–(3–Nitro–1,2,4–triazol–1–yl)–1–($\beta$–D–2,3,5–tri–O––acetylarabinofuranosyl) pyrimidin–2(1H)–ones. Valuable Intermediates in the Synthesis of Derivatives of 1–($\beta$–D–Arabinofuranosyl)cytosine (Ara–C)," *J.C.S. Perkin I*, 1982, 1171–1176.

Egholm, M. et al., "Peptide Nucleic Acids (PNA). Oligonucleotide Analogues with an Achiral Peptide Backbone," *J. Am. Chem Soc.*, 1992, 114, 1895–1897.

Egholm, M. et al., "Recognition of Guanine and Adenine in DNA by Cytosine and Thymine Containing Peptide Nucleic Acids (PNA)," *J. Am. Chem Soc.*, 1992, 114, 9677–9678.

Khorana, H. et al., "Studies on Polynucleotides: Total Synthesis of the Structural Gene for an Alanine Transfer Ribonucleic Acid from Yeast," *J. Mol. Biol.*, 1972, 72, 209–217.

Knudsen, H. et al., "Antisense Properties of duplex–and triplex–forming PNA," *Nucl. Acids Res.*, 1996, 24(3), 494–500.

Kumar, G. et al., "Improvements in Oligodeoxyribonucleotide Synthesis: Methyl N,N–Dialkylphosphoramidite Dimer Units for Solid Support Phosphite Methodology," *J. Org. Chem.*, 1984, 49, 4905–4912.

Kumar, P. et al., Express Protocol for Functionalization of Polymer Supports for Oligonucleotide Synthesis, *Nucleosides and Nucleotides*, 1996, 15(4), 879–888.

LaFrancois, C. J. et al., "Synthesis and Characterization of Isotopically Enriched Pyrimidine Deoxynucleoside Oxidation Damage Products," *Chem. Res. Toxicol.*, 1998, 11(1), 75–83.

Miura, K. et al., "Blockwise Mechanical Synthesis of Oligonucleotides by the Phosphoramidite Method," *Chem Pharm. Bull.*, 1987, 35(2), 833–836.

Montgomery, J. et al., "Synthesis of Potential Anticancer Agents. XX. 2–Fluoropurines," *Chem. Soc.*, 1960, 82, 463–468.

Nielsen, P. E. et al., "Sequence–Selective Recognition of DNA by Strand Displacement with a Thymine–Substituted Polyamide," *Science*, 1991, 254, 1497–1500.

Nielsen, P. E. et al., "Strand Displacement to Binding of a Duplex–Forming Homopurine PNA to a Homopyrimidine Duplex DNA Target," *J. Am. Chem. Soc.*, 1996, 118, 2287–2288.

Patel, D. J., "Marriage of Convenience," *Nature*, 1993, 365, 490–492.

Rasmussen, H. et al., "Crystal structure of a peptide nucleic acid (PNA) duplex at 1.7 Å resolution," *Nature Struct. Biol.*, 1997, 4(2), 98–101.

Reese, C. B. et al., "The Chemical Synthesis of Oligo–and Poly–Nucleotides by the Phosphotriester Approach," *Tetrahedron*, 1978, 34, 3143–3179.

Ross, B. S. et al., "A novel and economical synthesis of 2'–O–alkyl–uridines," *Nucleosides Nucleotides*, 1997, 16(7–9), 1641–1643.

Wolter, A. et al., "Polymer Support Oligonucleotide Synthesis XX: Synthesis of a Henhectacosa Deoxynucleotide by use of a Dimeric Phosphoramidite," *Nucleosides & Nucleotides*, 1986, 5(1), 65–77.

Vivès, E., et al., "Selective coupling of a highly basic peptide to an oligonucleotide," *Tetrahedron Letters*, 1997, 38(7), 1183–1186.

Zuckermann, R.N., et al., "Site–selective cleavage of RNA by a hybrid enzyme," *J. Am. Chem. Soc.*, 1988, 110, 1614–1615.

Zuckermann, R., et al., "Efficient methods for attachment of thiol specific probes to the 3'–ends of synthetic," *Nucleic Acids Res.*, 1987, 15((13), 5305–5321.

* cited by examiner

Figur 7

METHODS OF MODULATING PHARMACOKINETICS OF OLIGONUCLEOTIDES

CROSS REFERENCE TO RELATED APPLICATIONS

This application is a continuation-in-part of U.S. patent application Ser. No. 09/932,898 filed Aug. 20, 2001, now abandoned which claims benefit of U.S. provisional application Ser. No. 60/302,683 filed Jul. 3, 2001, the contents of which are incorporated by reference herein in their entirety.

FIELD OF INVENTION

This invention is directed to novel methods of increasing the binding of oligomeric compounds to proteins and oligomeric compounds useful therefor. Oligomeric compounds of the invention include modified oligonucleotides and modified peptide nucleic acids. The modified oligomeric compounds of the invention exhibit improved protein binding and high binding affinity to target RNA.

BACKGROUND OF THE INVENTION

Efficacy and sequence specific behavior of antisense oligonucleotides (ONs) in biological systems depend upon their resistance to enzymatic degradation. It is therefore essential, when designing potent antisense drugs, to combine features such as high binding affinity and mismatch sensitivity with nuclease resistance. Unmodified phosphodiester antisense oligonucleotides are degraded rapidly in biological fluids containing hydrolytic enzymes (Shaw, J. P.; Kent, K.; Bird, J.; Fishback, J.; Froehler, B. *Nucleic Acids Res.* 1991, 19, 747–750; Woolf, T. M.; Jennings, C. G. B.; Rebagliati, M; Melton, D. A. *Nucleic Acids Res.* 1990, 18, 1763–1769), and the first generation of modified antisense oligonucleotide drugs, such as 2'-deoxyphosphorothioate oligonucleotides, were also subject to enzymatic degradation (Maier, M.; Bleicher, K.; Kalthoff, H.; Bayer, E. *Biomed. Pept., Proteins Nucleic Acids* 1995, 1, 235–241; Agrawal, S.; Temsamani, J.; Tang, J. Y. *Proc. Natl. Acad. Sci.* 1991, 88, 7595–7599). Extensive stability against the various nucleases present in biological systems can best be achieved by modified oligonucleotides. Since 3' exonuclease activity is predominantly responsible for enzymatic degradation in serum-containing medium and in various eukaryotic cell lines, modifications located at the 3'-terminus significantly contribute to the nuclease resistance of an oligonucleotide (Shaw, J.-P.; Kent, K.; Bird, J.; Fishback, J.; Froehler, B. *Nucleic Acids Res.* 1991, 19, 747–750; Maier, M.; Bleicher, K.; Kalthoff, H.; Bayer, E. *Biomed. Pept., Proteins Nucleic Acids* 1995, 1,235–241).

The ribosyl sugar moiety has also been extensively studied to evaluate the effect its modification has on the properties of oligonucleotides relative to unmodified oligonucleotides. The 2'-position of the sugar moiety is one of the most studied sites for modification. Certain 2'-substituent groups have been shown to increase the lipohpilicity and enhance properties such as binding affinity to target RNA, chemical stability and nuclease resistance of oligonucleotides. Many of the modifications at the 2'-position that show enhanced binding affinity also force the sugar ring into the $C_3$-endo conformation.

One 2'-substituent group that has been shown to enhance the properties of oligonucleotides for antisense applications is the 2'-O—$CH_2CH_2$—O—$CH_3$ (2'-O-MOB). This modification in phosphodiester ONs offers about a 2° C. increase in tm/modification relative to 2'-deoxyphosphorothioate ONs. A phosphodiester ON modified with a 2'-O-MOE has about the same nuclease resistance as a 2'-deoxyphosphorothioate ON as shown by the half-life of the full-length oligonucleotide, $t_{1/2}$.

Although the 2'-position is a commonly used position for antisense applications, modifications of the 3' and 5' terminal hydroxyls of an oligonucleotide hav also been shown to be advantageous sites for modifications. Oligonucleotides bearing conjugate groups at these positions have shown improved pharmacokinetic and biodistribution properties including enhanced protein binding Peptide nucleic acids (PNAs) are compounds that in some respects are analogous to oligonucleotides, but which differ in structure. In peptide nucleic acids, the deoxyribose backbone has been replaced with a backbone having peptide linkages. Each subunit has attached a naturally occurring or non-naturally occurring base. One such backbone is constructed of repeating units of N-(2-aminoethyl)glycine linked through amide bonds. The synthesis of PNAs via preformed monomers was previously described in WO 92/20702 and WO 92/20703, the contents of which are herein incorporated by reference. More recent advances in the structure and synthesis of PNAs are illustrated in WO 93/12129 and U.S. Pat. No. 5,539,082, issued Jul. 23, 1996, the contents of both are incorporated herein by reference. Further, the literature is replete with publications describing synthetic procedures, biological properties and uses of PNAs. For example, PNAs possess the ability to effect strand displacement of double-stranded DNA. Patel, *Nature*, 1993, 365, 490. Improved synthetic procedures for PNAs have also been described. Nielsen et al., *Science*, 1991, 254, 1497; and Egholm, *J. Am. Chem. Soc.*, 1992, 114, 1895. PNAs form duplexes and triplexes with complementary DNA or RNA. Knudson et al., *Nucleic Acids Research*, 1996, 24, 494; Nielsen et al., *J. Am. Chem. Soc.*, 1996, 118, 2287; Egholm et al., *Science*, 1991, 254, 1497; Egholm et al., *J. Am. Chem. Soc.*, 1992, 114, 1895; and Egholm et al., *J. Am. Chem. Soc.*, 1992, 114, 9677.

PNA binds both DNA and RNA to form PNA/DNA or PNA/RNA duplexes. The resulting PNA/DNA or PNA/RNA duplexes are bound with greater affinity than corresponding DNA/DNA or DNA/RNA duplexes as evidence by their higher melting temperatures(tm). This high thermal stability has been attributed to the neutrality of the PNA backbone, which does not encounter the charge repulsion present in DNA or RNA duplexes. The neutral backbone of the PNA also renders the tm of PNA/DNA(RNA) duplexes practically independent of salt concentration. Thus the PNA/DNA duplex differs from the DNA/DNA duplex interactions which are highly dependent on ionic strength. Homopyrimidine PNAs have been shown to bind complementary DNA or RNA forming $(PNA)_2$/DNA(RNA) triplexes of high thermal stability (see, e.g., Egholm, et al., Science, 1991, 254, 1497; Egholm, et al., J. Am. Chem. Soc., 1992, 114, 1895; Egholm, et al., J. Am. Chem. Soc., 1992, 114, 9677).

The binding of a PNA strand to a DNA or RNA strand can occur in one of two orientations. The orientation is said to be anti-parallel when the DNA or RNA strand in a 5' to 3' orientation binds to the complementary PNA strand such that the carboxyl end of the PNA is directed towards the 5' end of the DNA or RNA and amino end of the PNA is directed towards the 3' end of the DNA or RNA. In the parallel orientation the carboxyl end and amino end of the PNA are in reverse orientation with respect to the 5'–3' direction of the DNA or RNA.

Human serum albumin (HSA) is an important protein that plays a crucial role in in vivo distribution and pharmacokinetics of many substances taken up in blood plasma. Human serum albumin is the principal protein found in blood plasma (approximately 60% of the total), that is responsible for much of the plasma colloidal osmotic pressure and serves as a transport protein carrying large organic anions. HSA in blood plasma binds to many endogenous and exogenous compounds with association constants typically in the range of $10^4$ to $10^6$ $M^{-1}$. As the most abundant protein in plasma (35–50 mg/mL) it plays an important role in the maintenance of blood pH and colloids and transports the drug substances to different parts in the body. It is also an important drug carrier in plasma. The ability of an oligomeric compound to bind to human serum albumin is an important property that determines its ability to distribute to all target tissues of interest.

Diester oligodeoxynucleotides don't show significant binding to HSA, however, phosphorothioate oligodeoxynucleotides bind with micromolar affinity. While phosphorothioate oligonucleotides exhibit both acceptable levels of nuclease resistance and HSA binding suitable for therapeutic applications, their "stickiness" to serum proteins other than HSA results in inhibitory effects of these proteins. Diester linked oligonucleotides modified with selected 2'-substituent groups have improved pharmacological properties and enhanced nuclease resistance. Combining 2'-modifications with the phosphodiester backbone offers a solution to overcome the stickiness of phosphorothioates and also maintain the nuclease resistance. However, these compounds lack the desired level of HSA binding.

Accordingly, it is the object of this invention to provide methods of increasing the binding of modified oligomeric compounds, particular oligonucleotides, oligonucleosides, and PNA's to proteins such as human serum albumin.

It is also the object of this invention to provide compounds that exhibit high binding affinity to target RNA.

Additional objects, advantages and novel features of this invention will become apparent to those skilled in the art upon examination of the following descriptions, figures and claims thereof, which are not intended to be limiting.

BRIEF DESCRIPTION OF THE DRAWINGS

The drawings presented herewith and the attendant examples are not to be construed as limited the invention in any way, but rather as serving only for purpose of exemplification.

Figure 18:
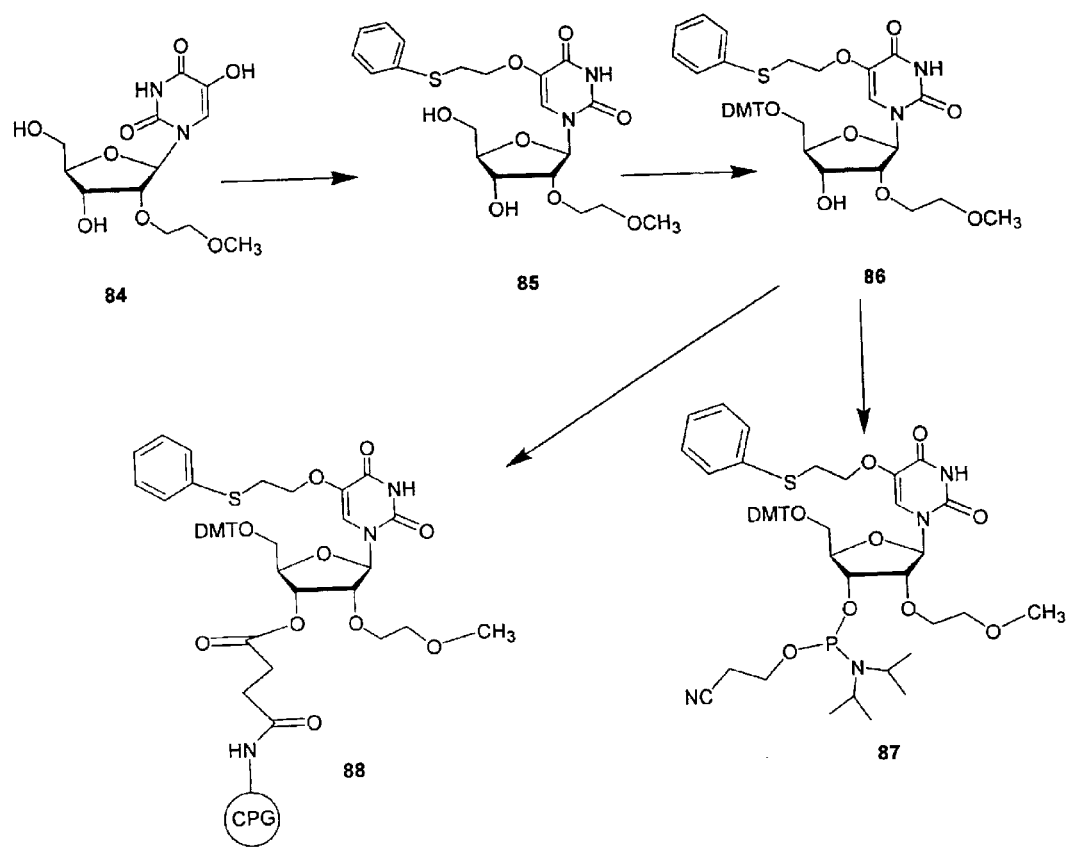

FIG. 18 depicts formation of 5'-O-DMT-2'-O-[2-(methoxy)ethyl]-5-[[2-(phenylthio)ethyl]oxo]uridine-3'-[(2-cyanoethyl)-N,N-diisopropylphosphoramidite] 87 and 5'-O-DMT-2'-O-[2-(methoxy)ethyl]-5-[[2-(phenylthio)ethyl]oxo]uridine-3'-O-succinyl CPG 88.

Figure 19:
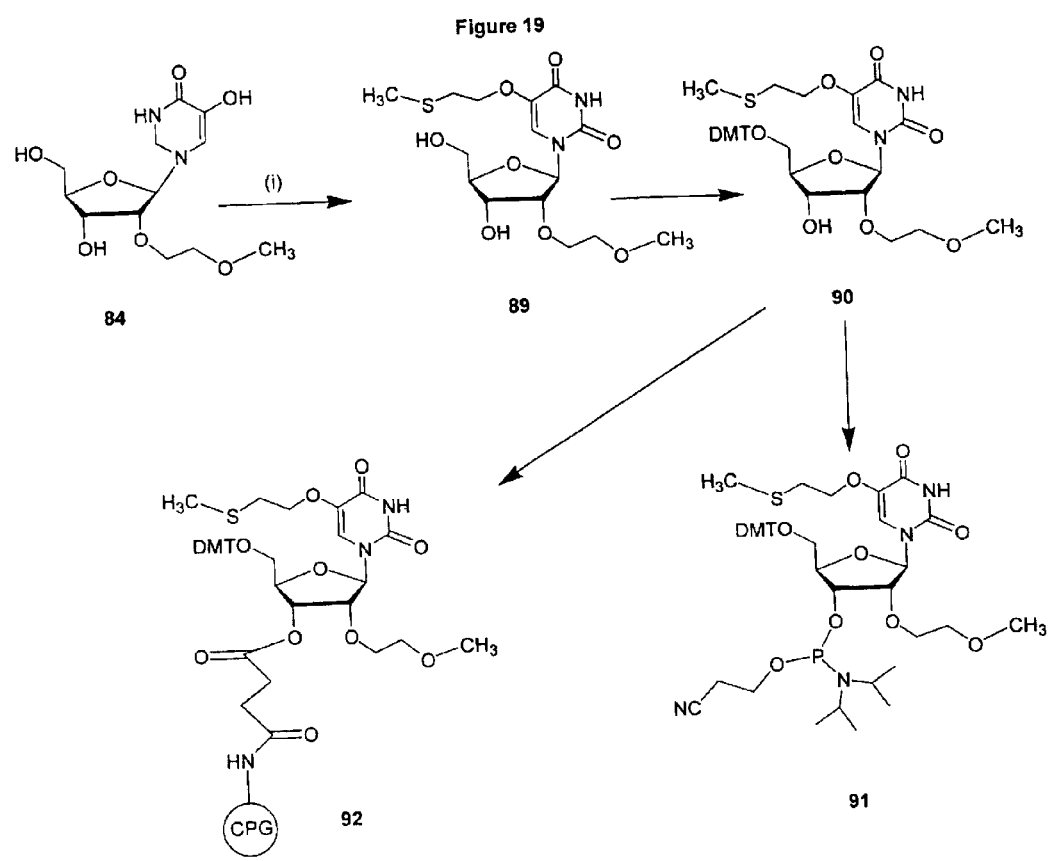

FIG. 19 depicts formation of 5'-O-DMT-2'-O-[2-(methoxy)ethyl]-5-[[2-(methylthio)ethyl]oxo]uridine-3'-[(2-cyanoethyl)-N,N-diisopropylphosphoramidite] 91 and 5-O-DMT-2'-O-[2-(methoxy)ethyl]-5-[[2-(phenylthio)ethyl]oxo]urdine-3'-O-succinyl CPG 92.

Figure 20:
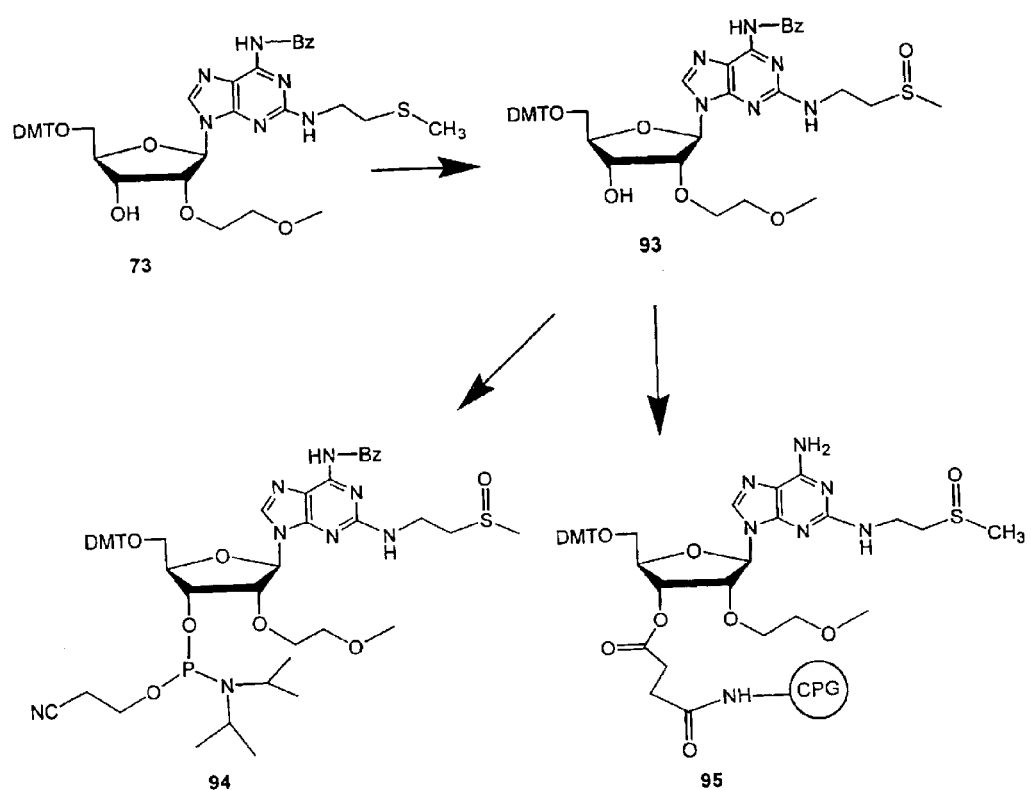

FIG. 20 depicts formation of N4-Benzoyl-5'-O-DMT-2'-O-[2-(methoxy)ethyl]-N²-[2-(methanesulfinyl)ethyl]-2-aminoadenosine-3'-[(2-cyanoethyl) -N,N-diisopropylphosphoramidite] 94 and N4-Benzoyl-5'-O-DMT-2'-O-[2-(methoxy)ethyl]-[N²-2-(methanesulfinyl)ethyl]-2-aminoadenosine-3'-O-succinyl CPG 95.

Figure 21:
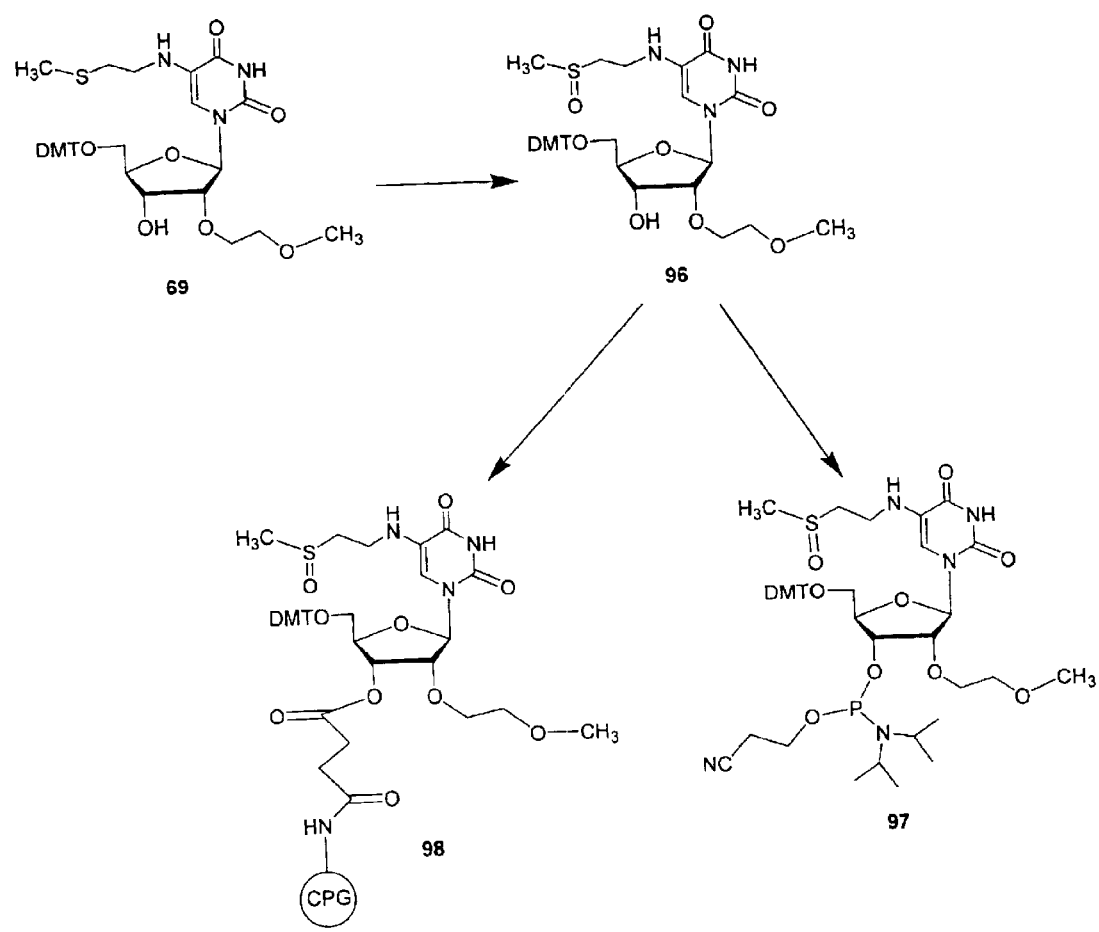

FIG. 21 depicts formation of 5'-O-DMT-2'-O-[2-(methoxy)ethyl]-5-[2-(methanesulfinyl) ethyl] aminouridine-3'-[(2-cyanoethyl)-N,N-diisopropylphosphoramidite] 97 and 5'-O-DMT-2'-O-[2-(methoxy)ethyl]-5-[2-(methanesulfinyl)ethyl]aminouridine-3'-O-succinyl CPG 98.

Figure 22:
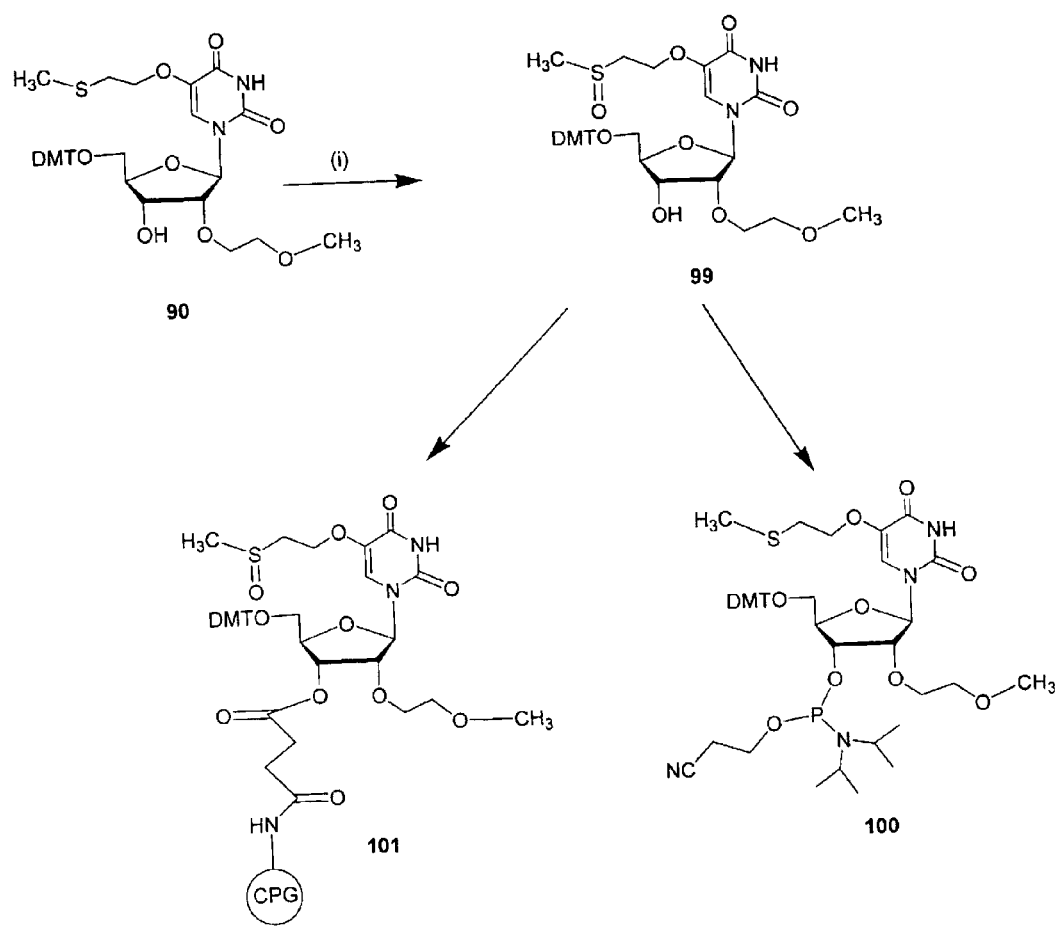

FIG. 22 depicts formation of 5'-O-DMT-2'-O-[2-(methoxy)ethyl]-5-[2-(methanesulfinyl)ethyl]oxouridine-3'-[(2-cyanoethyl)-N,N-diisopropylphosphoramidite] 100 and 5'-O-DMT-2'-O-[2-(methoxy)ethyl]-5-[2-(methanesulfinyl)ethyl]oxouridine-3'-O-succinyl CPG 101.

Figure 23:
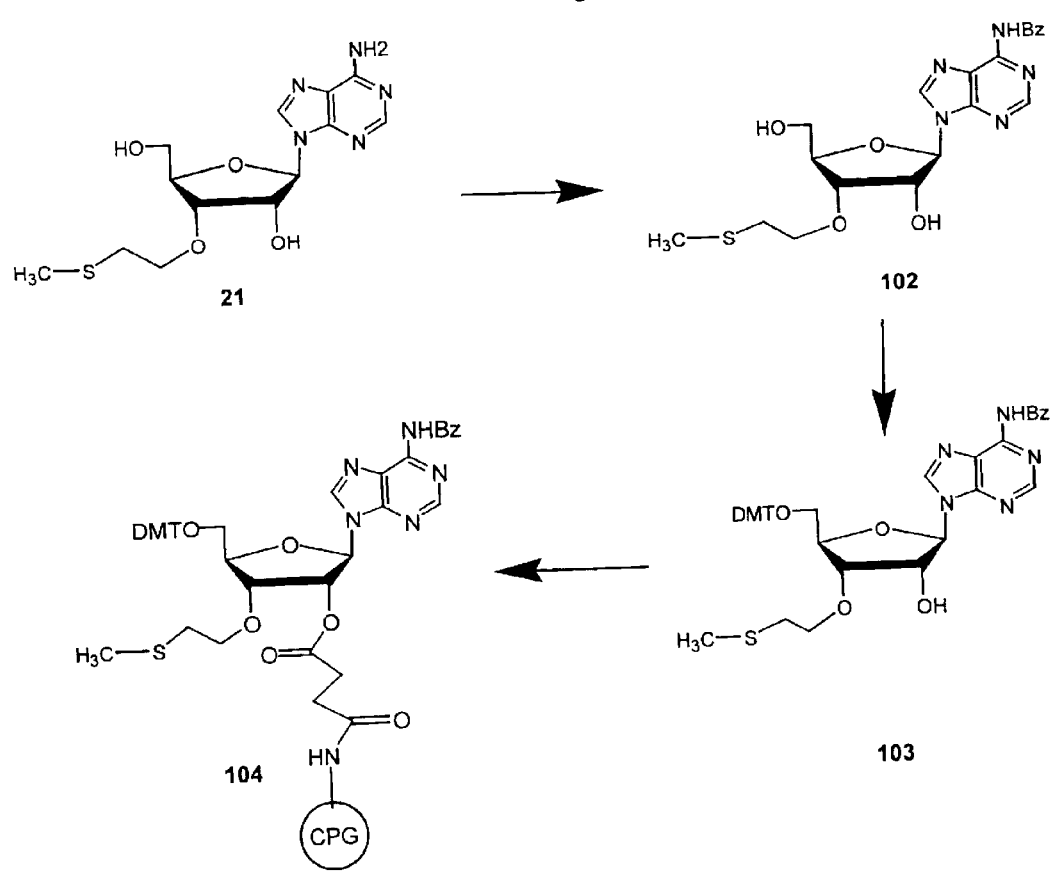

FIG. 23 depicts formation of 5'-O-DMT-3'-O-[2-(methylthio)ethyl]-N⁶-benzoyl-adenosine-2'-O-succinyl CPG 104.

Figure 24:
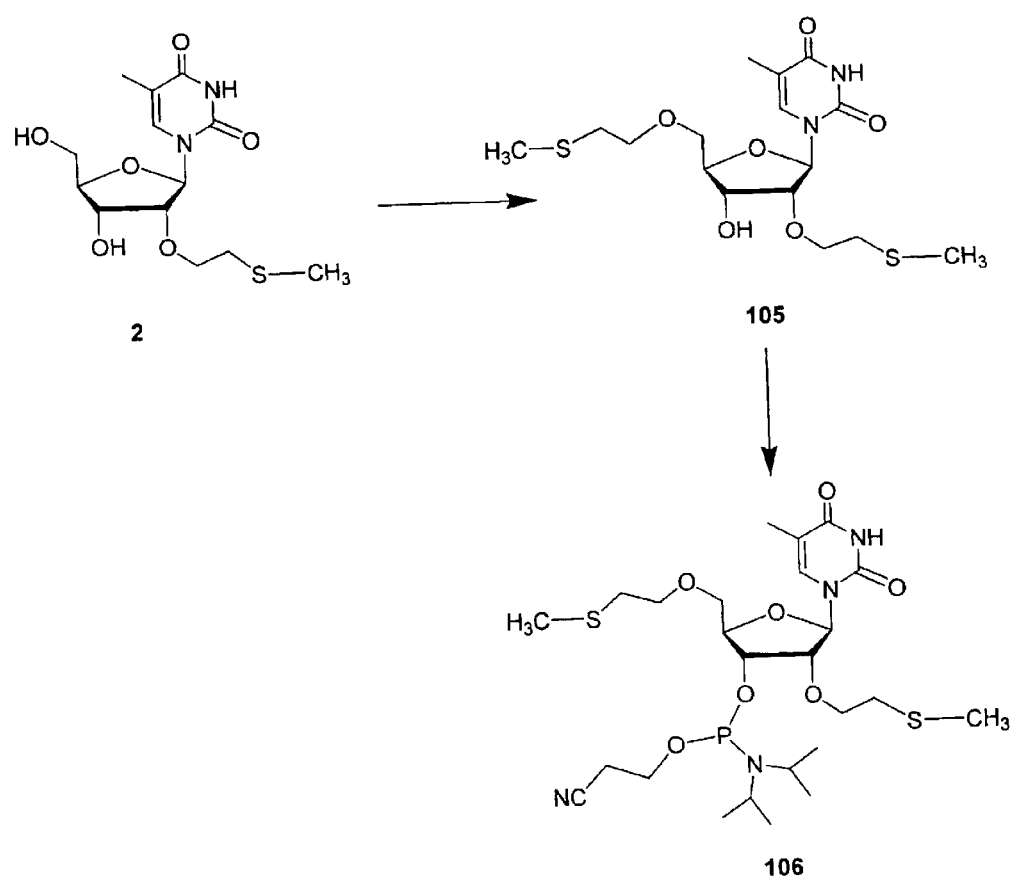

FIG. 24 depicts formation of 5'-O-[2-(methylthio)ethyl]-2'-O-[2-(methylthio)ethyl]-5-methyluridine-3'-[(2-cyanoethyl)-N,N-diisopropylphosphoramidite] 106.

Figure 25:
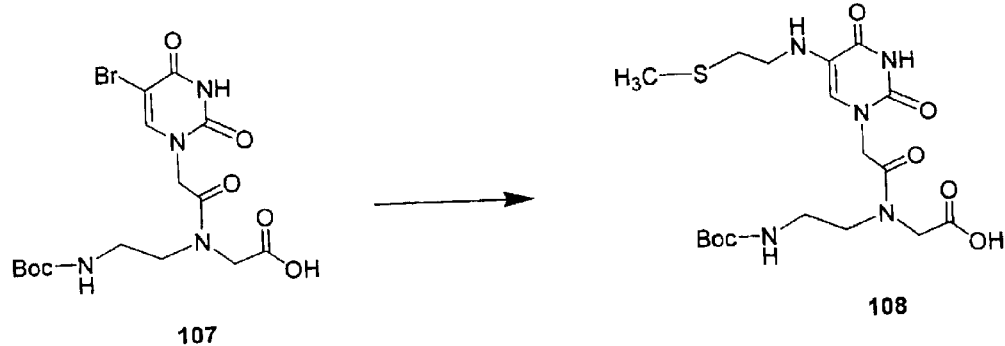

FIG. 25 depicts formation of N-[2-(tert-Butyloxycarbonylamino)ethyl]-N-[5-[2-(methylthio)ethyl] urac-1-yl]acetylglycine 108.

Figure 26:
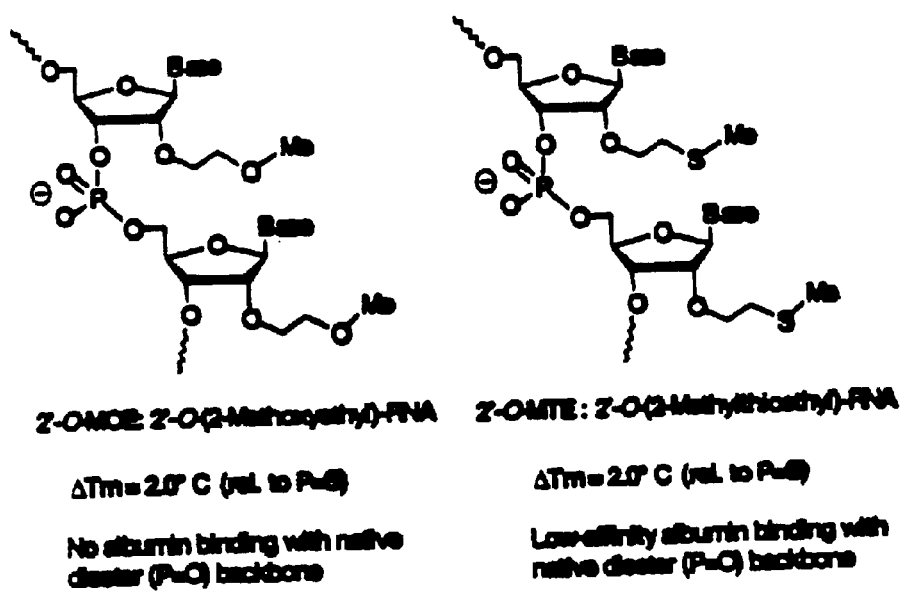

FIG. 26 depicts 2'-modifications including 2'-O-(2-methodyethyl) modification and 2'-O-[(2-methylthio)ethyl].

Figure 27:
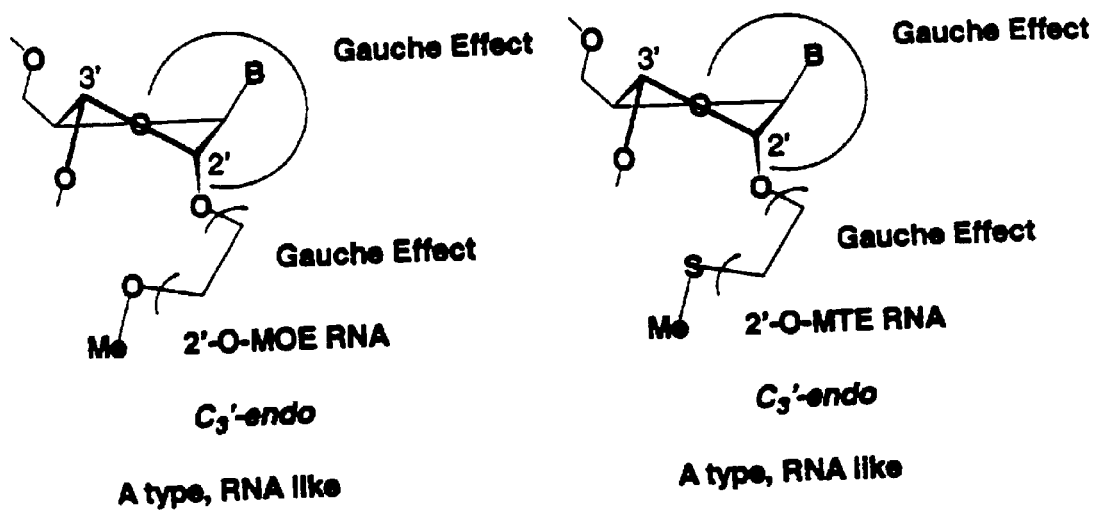

FIG. 27 depicts conformational preorganization of 2'-O-MOE RNA due to multiple gauche effects and possibility of similar effects in 2'-O-MTE RNA.

Figure 28:
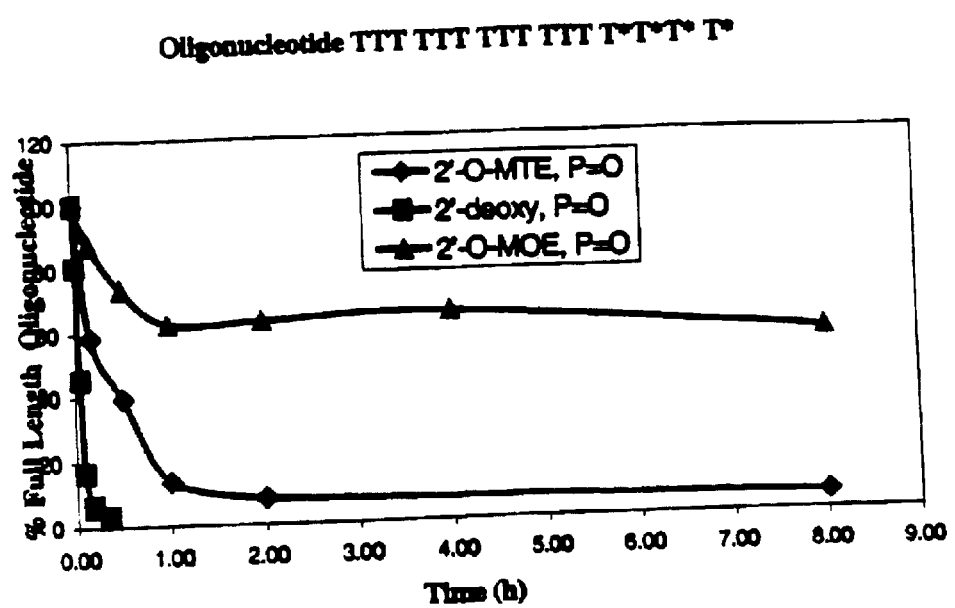

FIG. 28 depicts a table of digestion over time of oligonucleotide 121667 with Snake Venom Phosphodiesterase.

SUMMARY OF INVENTION

The present invention includes methods of increasing the binding of an oligomeric compound to proteins. The invention also includes novel compounds useful in the present methods. The methods include preparing an oligomeric compound having at least one group of formula I:

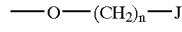
(I)

wherein:
each n is, independently, from 1 to about 10;
each J is, independently, a sulfonic acid (—S(=O)₂OH), a sulfonate salt (—S(=O)₂O⁻X⁺), a sulfoxide (—S(=O)—Z), a sulfone (—S(=O)₂—Z), —SH, —S—S—Z, or a thiol (—S—Z);

each X⁺ is a metal cation;
each Z is, independently, selected from the group consisting of substituted or unsubstituted C₁–C₂₀ alkyl, substituted or unsubstituted C₂–C₂₀ alkenyl, substituted or unsubstituted C₂–C₂₀ alkynyl, substituted or unsubstituted C₅–C₂₀ aryl wherein said substitution is alkyl or aryl;

covalently attached thereto thereby providing an enhanced oligomeric compound.

A preferred group of oligomeric compounds are oligonucleotides, oligonucleosides, and peptide nucleic acids as well as other oligomeric compounds bearing a base capable of binding to nucleic acids or proteins or as catalytic agents for nucleic acids, i.e. ribozymes.

In one embodiment of the invention, methods include compounds of formula I II

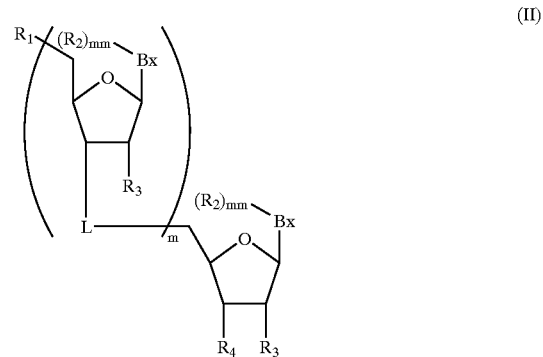
(II)

wherein:
each Bx is, independently, an optionally protected heterocyclic base moiety;
R₁ is hydrogen, hydroxyl, a protected hydroxyl, a nucleoside, a nucleotide, an oligonucleoside, an oligonucleotide or a group of formula I;
R₄ is hydrogen, hydroxyl, a protected hydroxyl, a nucleoside, a nucleotide, an oligonucleoside, an oligonucleotide or a group of formula I;
each R₂ is a group of formula I;
each R₃ is, independently, hydrogen, hydroxyl, a protected hydroxyl, an optionally protected sugar substituent group or a group of formula I;
L is an internucleoside linking group;
m is from 3 to about 50; and
each mm is, independently, 0 or 1;
wherein at least one R₁, R₂, R₃ or R4 is a group of formula I.

In a further preferred embodiment of the methods of the invention the oligomeric compounds are compounds of formula III:

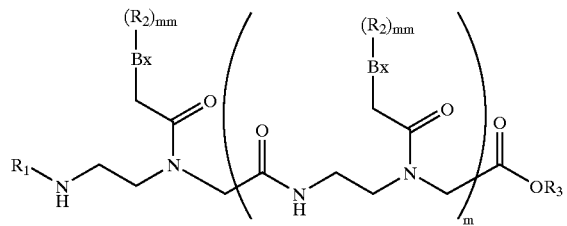
(III)

wherein:

each Bx is an optionally protected heterocyclic base moiety;

$R_1$ is hydrogen or an amino protecting group;

each $R_2$ is a group of formula I;

$R_3$ is hydrogen or a hydroxyl protecting group;

m is from 3 to about 50; and each mm is, independently, 0 or 1;

and at least one mm is 1.

The present invention also provides compounds of formula II:

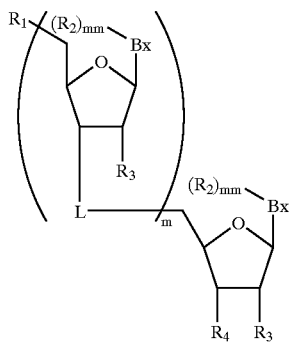

(II)

wherein:

each Bx is an optionally protected heterocyclic base moiety;

$R_1$ is hydrogen, hydroxyl, a protected hydroxyl, a nucleoside, a nucleotide, an oligonucleoside, an oligonucleotide or a group of formula I;

$R_4$ is hydrogen, hydroxyl, a protected hydroxyl, a nucleoside, a nucleotide, an oligonucleoside, an oligonucleotide or a group of formula I;

each $R_2$ is a group of formula I:

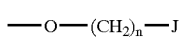

(I)

wherein:

each n is, independently, from 1 to about 10;

each J is, independently, a sulfonic acid (—S(=O)$_2$OH), a sulfonate salt (—S(=O)$_2$O$^-$X$^+$), a sulfoxide (—S(=O)—Z), a sulfone (—S(=O)$_2$—Z), —SH, —S—S—Z, or a thiol (—S—Z);

each X$^+$ is a metal cation;

each Z is, independently, selected from the group consisting of $C_1$–$C_{20}$ alkyl, $C_2$–$C_{20}$ alkenyl, $C_2$–$C_{20}$ alkynyl, $C_1$–$C_{20}$ aryl and $C_5$–$C_{20}$ aryl substituted $C_1$–$C_{20}$ alkyl;

each $R_3$ is, independently, hydrogen, hydroxyl, a protected hydroxyl, an optionally protected sugar substituent group or a group of formula I;

L is an internucleoside linking group;

m is from 3 to about 50; and each mm is, independently, 0 or 1;

wherein at least one of said L is other than a phosphodiester internucleoside linkage and at least one of said $R_1$, $R_2$, $R_3$ and $R_4$ is a compound of formula I.

The present invention also provides compounds of formula III:

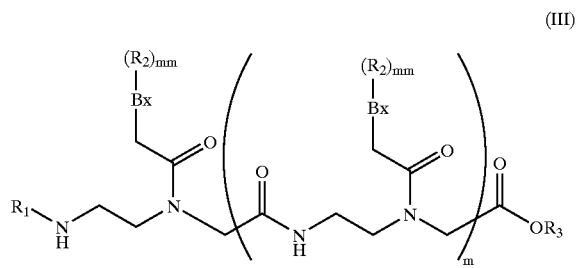

(III)

wherein:

each Bx is an optionally protected heterocyclic base moiety;

$R_1$ is hydrogen or an amino protecting group;

each $R_2$ is a group of formula I;

$R_3$ is hydrogen or a hydroxyl protecting group;

m is from 3 to about 50; and each mm is, independently, 0 or 1;

and at least one mm is 1.

The present invention also includes compounds of formula (IV):

(IV)

wherein:

each Bx is independently an optionally protected heterocyclic base moiety;

$R_1$ is hydrogen, hydroxyl, a protected hydroxyl group, a leaving group or a group of formula I;

(I)

wherein:

each n is, independently, from 1 to about 10;

each J is, independently, a sulfonic acid (—S(=O)$_2$OH), a sulfonate salt (—S(=O)$_2$O$^-$X$^+$), a sulfoxide (—S(=O)—Z), a sulfone (—S(=O)$_2$—Z), —SH, —S—S—Z, or a thiol (—S—Z);

each X$^+$ is a metal cation;

each Z is, independently, selected from the group consisting of substituted or unsubstituted $C_1$–$C_{20}$ alkyl, substituted or unsubstituted $C_2$–$C_{20}$ alkenyl, substituted or unsubstituted $C_2$–$C_{20}$ alkynyl, substituted or unsubstituted $C_5$–$C_{20}$ aryl wherein said substitution is alkyl or aryl;

$R_4$ is hydrogen, hydroxyl, a protected hydroxyl, an optionally protected sugar substituent group or a group of formula I;

each $R_2$ is a group of formula I;

each $R_3$ is, independently, hydrogen, hydroxyl, a protected hydroxyl, an optionally protected sugar substituent group or a group of formula I;

mm is 0 or 1;

wherein at least one $R_1$, $R_2$, $R_3$ or $R_4$ is a group of formula I.

In yet another embodiment, the present invention relates to compounds of formula (V):

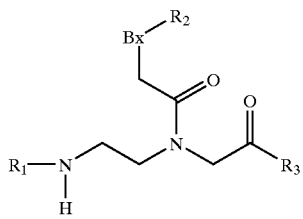

(V)

wherein:

Bx is an optionally protected heterocyclic base moiety;

$R_1$ is hydrogen, hydroxyl or a protected hydroxyl group;

$R_2$ is a group of formula I:

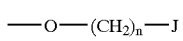

(I)

wherein:

n is from 1 to about 10;

J is a sulfonic acid (—S(=O)$_2$OH), a sulfonate salt (—S(=O)$_2$O$^-$X$^+$), a sulfoxide (—S(=O)—Z), a sulfone (—S(=O)$_2$—Z), —SH, —S—S—Z, or a thiol (—S—Z);

X$^+$ is a metal cation;

Z is selected from the group consisting of substituted or unsubstituted $C_1$–$C_{20}$ alkyl, substituted or unsubstituted $C_2$–$C_{20}$ alkenyl, substituted or unsubstituted $C_2$–$C_{20}$ alkynyl, substituted or unsubstituted $C_5$–$C_{20}$ aryl wherein said substitution is alkyl or aryl; and $R_3$ is hydrogen or an amino protecting group.

DESCRIPTION OF PREFERRED EMBODIMENTS

The present invention presents novel methods directed to increasing the binding of oligomeric compounds to proteins. The present invention also includes novel oligomeric compounds having increased protein binding. The compositions used in the present methods include at least one group of formula I:

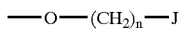

(I)

wherein:

each n is, independently, from 1 to about 10;

each J is, independently, a sulfonic acid (—S(=O)$_2$OH), a sulfonate salt (—S(=O)$_2$O$^-$X$^+$), a sulfoxide (—S(=O)—Z), a sulfone (—S(=O)$_2$—Z), —SH, —S—S—Z, or a thiol (—S—Z);

each X$^+$ is a metal cation;

each Z is, independently, selected from the group consisting of substituted or unsubstituted $C_1$–$C_{20}$ alkyl, substituted or unsubstituted $C_2$–$C_{20}$ alkenyl, substituted or unsubstituted $C_2$–$C_{20}$ alkynyl, substituted or unsubstituted $C_5$–$C_{20}$ aryl wherein said substitution is alkyl or aryl;

covalently attached thereto thereby providing an enchanced oligomeric compound.

As used herein, the term oligomeric compound is intended to include oligonucleotides, oligonucleotide analogs, oligonucleosides, PNAs and PNA analogues. Oligonucleotides and peptide nucleic acids, or more broadly oligomeric compounds, according to the present invention can exist in a variety of oligomer lengths. The ranges of the lengths disclosed herein include all combinations and subcombinations of ranges and specific oligomer amounts therein. When used as "building blocks" in assembling larger oligomeric compounds (i.e., as synthons), smaller oligomeric compounds are preferred. Libraries of dimeric, trimeric, or higher order compounds can be prepared for use as synthons in the methods of the invention. The use of small sequences synthesized via solution phase chemistries in automated synthesis of larger oligonucleotides enhances the coupling efficiency and the purity of the final oligonucleotides. See for example: Miura, K., et al., *Chem. Pharm. Bull.*, 1987, 35, 833–836; Kumar, G., and Poonian, M. S., *J. Org. Chem.*, 1984, 49,4905–4912; Bannwarth, W., *Helvetica Chim Acta*, 1985, 68, 1907–1913; Wolter, A., et al., *nucleosides and nucleotides*, 1986, 5, 65–77, each of which are hereby incorporated by reference in their entirety.

The oligomeric compounds of the invention can include more than one group of formula I at various positions. Oligomeric compounds comprised of linked nucleoside units can include groups of formula I covalently attached to the heterocyclic base moiety or the ribosyl sugar moiety. A single nucleoside within an oligomeric compound can include more than one group of formula I. A plurality of groups of formula I can be included at various positions of individual nucleosides within and oligomeric compound. Groups of formula I can be located at one or both of the 3' and 5'-termini of an oligomeric compound. Alternatively, one or more groups of formula I can be located internally within an oligomeric compound. Thus all manner of single or multiple substitutions imparting advantageous properties to an oligomeric compound are envisioned by the present invention.

In certain preferred embodiments, J is —S—Z and Z is a straight or branched $C_1$ to $C_{20}$ alkyl group. Preferred alkyl groups are methyl, ethyl, or propyl. Particularly preferred for the alkyl group is methyl. When J is —S—Z, Z can be an aryl having 5 to about 14 carbon atoms. Z can also be phenyl. In a certain embodiments at least one J is a sulfonic acid and in others, at least one J is a sulfonate salt. Of the latter embodiments, X$_+$ can be various salts including Na+. In other embodiments at least one J is a sulfoxide. When at least one J is a sulfoxide, Z can be substituted or unsubstituted $C_1$–$C_{20}$ alkyl or substituted or unsubstituted $C_5$–$C_{20}$ aryl. In further embodiments at least one J is a sulfone and Z can be a substituted or unsubstituted $C_1$–$C_{20}$ alkyl or substituted or unsubstituted $C_5$–$C_{20}$ aryl.

In certain particular embodiments of the methods of the present invention, the oligomeric compounds have formula II:

(II)

[Structure of formula II showing sugar-base oligomer]

wherein:

each Bx is, independently, an optionally protected heterocyclic base moiety;

$R_1$ is hydrogen, hydroxyl, a protected hydroxyl, a nucleoside, a nucleotide, an oligonucleoside, an oligonucleotide or a group of formula I;

$R_4$ is hydrogen, hydroxyl, a protected hydroxyl, a nucleoside, a nucleotide, an oligonucleoside, an oligonucleotide or a group of formula I;

each $R_2$ is a group of formula I;

each $R_3$ is, independently, hydrogen, hydroxyl, a protected hydroxyl, an optionally protected sugar substituent group or a group of formula I;

L is an internucleoside linking group;

m is from 3 to about 50; and each mm is, independently, 0 or 1;

wherein at least one $R_1$, $R_2$, $R_3$, or $R_4$ is a group of formula I.

A preferred internucleoside linking is one that contain a phosphorus atom. Preferred internucleoside linking groups that include a phosphorus atom include phosphodiesters, phosphorothioates and phosphorodithioates.

In other general embodiments, m is from about 8 to about 30. In more general embodiments, m is from about 15 to about 25. In some embodiments, mm is 0. There are also methods wherein at least two $R_1$, $R_2$, $R_3$, and $R_4$ are groups of formula I. Substantially all $R_3$ can be groups of formula I in many embodiments. In others, $R_1$ is a compound of formula I and in more embodiments, $R_4$ is a group of formula I.

In other embodiments of the methods of this invention, the oligomeric compounds have formula III:

(III)

[Structure of formula III]

wherein:

each Bx is an optionally protected heterocyclic base moiety;

$R_1$ is hydrogen or an amino protecting group;

each $R_2$ is a group of formula I;

$R_3$ is hydrogen or a hydroxyl protecting group;

m is from 3 to about 50; and each mm is, independently, 0 or 1 with the proviso that at least one mm is 1.

"m" can be selected to be from about 8 to about 30. A more preferred range for m is from about 15 to about 25. Each mm is selected, independently, to be 1 or 0.

The present invention also provides compounds of formula II:

(II)

[Structure of formula II]

wherein:

each Bx is an optionally protected heterocyclic base moiety;

$R_1$ is hydrogen, hydroxyl, a protected hydroxyl, a nucleoside, a nucleotide, an oligonucleoside, an oligonucleotide or a group of formula I;

$R_4$ is hydrogen, hydroxyl, a protected hydroxyl, a nucleoside, a nucleotide, an oligonucleoside, an oligonucleotide or a group of formula I;

each $R_2$ is a group of formula I:

$$-O-(CH_2)_n-J \qquad (I)$$

wherein:

each n is, independently, from 1 to about 10;

each J is, independently, a sulfonic acid ($-S(=O)_2OH$), a sulfonate salt ($-S(=O)_2O^-X^+$), a sulfoxide ($-S(=O)-Z$), a sulfone ($-S(=O)_2-Z$), $-SH$, $-S-S-Z$, or a thiol ($-S-Z$);

each $X^+$ is a metal cation;

each Z is, independently, selected from the group consisting of $C_1-C_{20}$ alkyl, $C_2-C_{20}$ alkenyl, $C_2-C_{20}$ alkynyl, $C_5-C_{20}$ aryl and $C_5-C_{20}$ aryl substituted $C_1-C_{20}$ alkyl;

each $R_3$ is, independently, hydrogen, hydroxyl, a protected hydroxyl, an optionally protected sugar substituent group or a group of formula I;

L is an internucleoside linking group;

m is from 3 to about 50; and each mm is, independently, 0 or 1;

wherein at least one L is other than a phosphodiester internucleoside linkage and at least one $R_1$, $R_2$, $R_3$, or $R_4$ is a compound of formula I.

Particular variations of this embodiment of the invention include compounds of formula II wherein $R_3$ is an optionally protected sugar substituent group. In other compounds on the invention at least two of $R_1$, $R_2$, $R_3$, and $R_4$ are selected as groups of formula I. At least two of $R_3$ can be, independently, groups of formula I. There are also those compounds wherein substantially all $R_3$ groups are of formula I. In other embodiments, just $R_1$ is a group of formula I and, on others, just $R_4$ is a group of formula I.

In other variations of the above embodiment, J is —S—Z and Z is a straight chained or branched $C_1$ to $C_{20}$ alkyl group. Preferred alkyl groups are methyl, ethyl, or propyl, particularly methyl. In other embodiments of the invention, J is —S—Z and Z is aryl having from 5 to about 14 carbon atoms. Z can be phenyl. In other embodiments, at least one J is a sulfonic acid or a sulfonate salt. $X^+$ can be various cations including $K^+$ and $Na^+$. At least one J can be a sulfoxide or a sulfone. In either of the preceding variations, Z can be substituted or unsubstituted $C_1$–$C_{20}$ alkyl or substituted or unsubstituted $C_5$–$C_{20}$ aryl.

In other embodiments m is selected to be from about 8 to about 30. In more preferred compounds m is selected to be from about 15 to 25.

Other embodiments of the present invention include compounds of formula III:

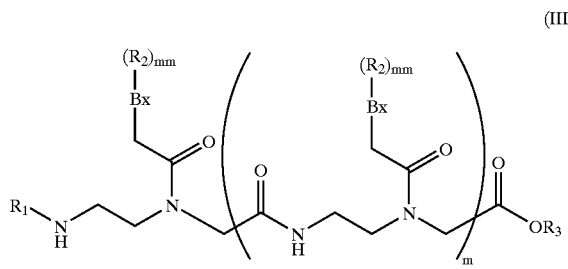

(III)

wherein:
each Bx is, independently, an optionally protected heterocyclic base moiety;
$R_1$ is hydrogen or an amino protecting group;
$R_3$ is hydrogen or a hydroxyl protecting group;
each $R_2$ is a group of formula I;

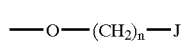

(I)

wherein:
each n is, independently, from 1 to about 10;
each J is, independently, a sulfonic acid (—S(=O)$_2$OH), a sulfonate salt (—S(=O)$_2$O$^-$X$^+$), a sulfoxide (—S(=O)—Z), a sulfone (—S(=O)$_2$—Z), —SH, —S—S—Z, or a thiol (—S—Z);
each $X^+$ is a metal cation;
each Z is, independently, selected from the group consisting of substituted or unsubstituted $C_1$–$C_{20}$ alky, substituted or unsubstituted $C_2$–$C_{20}$ alkenyl, substituted or unsubstituted $C_2$–$C_{20}$ alkynyl, substituted or unsubstituted $C_5$–$C_{20}$ aryl wherein said substitution is alkyl or aryl;
m is from 3 to about 50; and
each mm is, independently, 0 or 1 with the proviso that at least one mm is 1.

J can be —S—Z and Z is a straight or branched $C_1$ to $C_{20}$ alkyl group. Preferred alkyl groups are methyl, ethyl or propyl, particularly methyl. Z can be aryl having from 6 to about 14 carbon atoms. In other embodiments, Z is phenyl or particularly sulfonyl. There are embodiments of the present invention wherein n is selected to be 2. In other embodiments, m can be in a range from about 8 to about 30, particularly from about 15 to about 25. In some embodiments of the present invention, at least two $R_2$ are groups of formula I or, in others, all $R_2$ are groups of formula I.

In another aspect, the present invention relates to compounds of formula (IV):

(IV)

100811 wherein:
each Bx is independently an optionally protected heterocyclic base moiety;
$R_1$ is hydrogen, hydroxyl, a protected hydroxyl group, a leaving group or a group of formula I;

(I)

wherein:
each n is, independently, from 1 to about 10;
each J is, independently, a sulfonic acid (—S(=O)$_2$OH), a sulfonate salt (—S(=O)$_2$O$^-$X$^+$), a sulfoxide (—S(=O)—Z), a sulfone (—S(=O)$_2$—Z), —SH, —S—S—Z, or a thiol (—S—Z);
each $X^+$ is a metal cation;
each Z is, independently, selected from the group consisting of substituted or unsubstituted $C_1$–$C_{20}$ alkyl, substituted or unsubstituted $C_2$–$C_{20}$ alkenyl, substituted or unsubstituted $C_2$–$C_{20}$ alkynyl, substituted or unsubstituted $C_5$–$C_{20}$ aryl wherein said substitution is alkyl or aryl;
$R_4$ is hydrogen, hydroxyl, a protected hydroxyl, an optionally protected sugar substituent group or a group of formula I;
each $R_2$ is a group of formula I;
each $R_3$ is, independently, hydrogen, hydroxyl, a protected hydroxyl, an optionally protected sugar substituent group or a group of formula I; mm is 0 or 1;

wherein at least one $R_1$, $R_2$, $R_3$ or $R_4$ is a group of formula I. In particular embodiments of the present invention, J can be —S—Z and Z is $C_1$–$C_{20}$ alkyl. Preferred alkyl are methyl, ethyl, or propyl, particularly methyl. In other embodiments, J is —S—Z and Z is aryl having from 6 to about 14 carbon atoms. Z can be phenyl or sulfonyl. In some embodiments, n is selected to be 2. In certain embodiments, mm is selected to be 0.

In yet other embodiments of the present invention, there are compounds of formula (V):

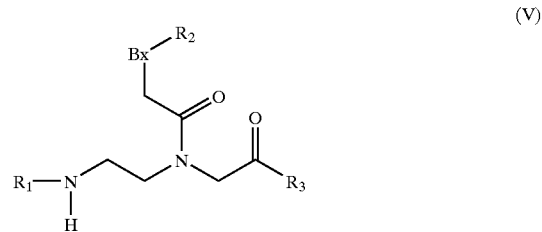

(V)

wherein:

Bx is an optionally protected heterocyclic base moiety;
R₁ is hydrogen, hydroxyl or a protected hydroxyl group;
R₂ is a group of formula I:

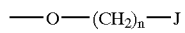  (I)

wherein:

each n is, independently, from 1 to about 10;
each J is, independently, a sulfonic acid (—S(=O)₂OH), a sulfonate salt (—S(=O)₂O⁻X⁺), a sulfoxide (—S(=O)—Z), a sulfone (—S(=O)₂—Z), —SH, —S—S—Z, or a thiol (—S—Z);
each X⁺ is a metal cation;
each Z is, independently, selected from the group consisting of substituted or unsubstituted C₁–C₂₀ alkyl, substituted or unsubstituted C₂–C₂₀ alkenyl, substituted or unsubstituted C₂–C₂₀ alkynyl, substituted or unsubstituted C₅C₂₀ aryl wherein said substitution is alkyl or aryl; and
R₃ is hydrogen or an amino protecting group.

In certain embodiments having compounds of formula V, J is —S—Z and Z is a straight or branched C₁ to C₂₀ alkyl group. Preferred alkyl groups are methyl, ethyl or propyl, particularly, methyl. Z can be aryl having from 6 to about 14 carbon atoms. There are embodiments wherein Z can be phenyl or, particularly, sulfonyl. In other embodiments, J is a sulfonic acid or a sulfonate salt. X⁺ can be various cations including K⁺ and Na⁺ in some instances. J can be a sulfoxide or a sulfone. In either of the preceding variations, Z can be substituted or unsubstituted C₁–C₂₀ alkyl or substituted or unsubstituted C₅–C₂₀ aryl, respectively. There are other embodiments wherein n can be 2 and mm can be 0 in others.

In one aspect of the present invention the methods of enhancing the protein binding of oligomeric compounds are useful in the preparation of antisense therapeutics. Antisense oligonucleotides have been employed as therapeutic moieties in the treatment of disease states in animals and man. Antisense oligonucleotide drugs, including ribozymes, have been safely and effectively administered to humans and numerous clinical trials are presently underway. It is thus established that oligonucleotides can be useful therapeutic modalities that can be configured to be useful in treatment regimes for treatment of cells, tissues and animals, especially humans.

As used herein the term "protein" is intended to include any of a group of complex organic compounds, consisting essentially of combinations of amino acids linked via peptide linkages, that include carbon, hydrogen, oxygen, nitrogen, and sometimes sulfur./*−+ One such protein is serum albumin, more particularly human serum albumin. Human serum albumin is a component of blood serum and is water soluble. The binding of compounds to serum albumin can be used to estimate plasma protein binding (see, for example, Beaudry et al., "Determination of drug-plasma protein binding using human serum albumin chromatographic column and multiple linear regression model," Biomed. Chromatogr. 13:401–406 (1999)). Beaudry et al. found a strong correlation between the binding of pharmaceutical compounds to human serum albumin and to plasma proteins in general.

In the context of this invention, the term "oligonucleotide" refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

While antisense oligonucleotides are a preferred form of antisense compound, the present invention comprehends other oligomeric compounds useful in antisense applications, including but not limited to oligonucleotide mimetics such as are described below. The antisense compounds in accordance with this invention preferably comprise from about 8 to about 50 nucleobases (i.e. from about 8 to about 50 linked nucleosides). Particularly preferred antisense compounds are antisense oligonucleotides, even more preferably those comprising from about 12 to about 30 nucleobases. Antisense compounds include ribozymes, external guide sequence (EGS) oligonucleotides (oligozymes), and other short catalytic RNAs or catalytic oligonucleotides which hybridize to the target nucleic acid and modulate its expression.

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'–5' linkages, 2'–5' linked analogs of these, and those having inverted polarity wherein one or more internucleotide linkages is a 3' to 3', 5' to 5' or 2' to 2' linkage. Preferred oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

Representative United States patents that teach the preparation of the above a phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, certain of which are commonly owned with this application, and each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

In other preferred oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., *Science,* 1991, 254, 1497–1500.

Most preferred embodiments of the invention are oligonucleotides with phosphorothioate backbones and oligonucleosides with heteroatom backbones, and in particular —$CH_2$—NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —O—N($CH_3$)—$CH_2$—$CH_2$— [wherein the native phosphodiester backbone is represented as —O—P—O—$CH_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Each optionally protected sugar substituent group is, independently, $C_1$–$C_{20}$ alkyl, $C_2$–$C_{20}$ alkenyl, $C_2$–$C_{20}$ alkynyl, $C_5$–$C_{20}$ aryl, —O-alkyl, —O-alkenyl, —O-alkynyl, —O-alkylamino, —O-alkylalkoxy, —O-alkylaminoalkyl, —O-alkyl imidazole, —OH, —SH, —S-alkyl, —S-alkenyl, —S-alkynyl, —N(H)-alkyl, —N(H)-alkenyl, —N(H) alkynyl, —N(alkyl)$_2$, —O-aryl, —S-aryl, —NH-aryl, —O-aralkyl, —S-aralkyl, —N(H)-aralkyl, phthalimido (attached at N), halogen, amino, keto (—C(=O)—R), carboxyl (—C(=O)OH), nitro (—$NO_2$), nitroso (—N=O), cyano (—CN), trifluoromethyl (—$CF_3$), trifluoromethoxy (—O—$CF_3$), imidazole, azido (—$N_3$), hydrazino (—N(H)—$NH_2$), aminooxy (—O—$NH_2$), isocyanato (—N=C=O), sulfoxide (—S(—O)—R), sulfone (—S(=O)$_2$—R), disulfide (—S—S—R), silyl, heterocycle, carbocycle, intercalator, reporter group, conjugate, polyamine, polyamide, polyalkylene glycol, and polyethers of the formula (—O-alkyl)$_m$, where m is 1 to about 10; wherein each R is, independently, hydrogen, a protecting group or substituted or unsubstituted alkyl, alkenyl, or alkynyl wherein said substituted alkyl, alkenyl, or alkynyl are substituted with haloalkyl, alkenyl, alkoxy, thioalkoxy, haloalkoxy, aryl groups as well as halogen, hydroxyl, amino, azido, carboxy, cyano, nitro, mercapto, sulfides, sulfones, and sulfoxides. A particularly preferred sugar substituent group of formula I is 2'-O—$CH_2$—$CH_2$—S—$CH_3$ (referred to as 2'-O-MTE)

or each sugar substituent group has one of formula VI or VII:

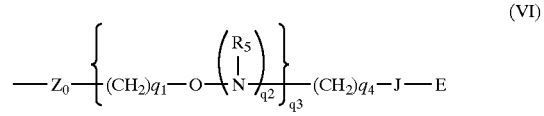

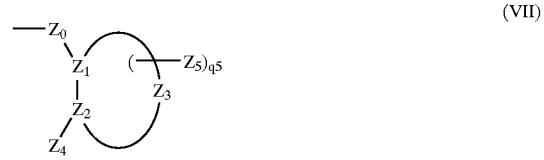

101001 wherein:

$Z_0$ is O, S or NH;

J is a single bond, O or C(=O);

E is $C_1$–$C_{10}$ alkyl, N($R_5$)($R_6$), N($R_5$)($R_7$), N=C($R_{5a}$)($R_{6a}$), N=C($R_{5a}$)($R_{7a}$) or has formula IX;

each $R_8$, $R_9$, $R_{11}$ and $R_{12}$ is, independently, hydrogen, C(O)$R_{13}$, substituted or unsubstituted $C_1$–$C_{10}$ alkyl, substituted or unsubstituted $C_2$–$C_{10}$ alkenyl, substituted or unsubstituted $C_2$–$C_{10}$ alkynyl, alkylsulfonyl, arylsulfonyl, a chemical functional group or a conjugate group, wherein the substituent groups are selected from hydroxyl, amino, alkoxy, carboxy, benzyl, phenyl, nitro, thiol, thioalkoxy, halogen, alkyl, aryl, alkenyl and alkynyl;

or optionally, $R_{11}$ and $R_{12}$, together from a phthalimido moiety with the nitrogen atom to which they are attached;

each $R_{13}$ is, independently, substituted or unsubstituted $C_1$–$C_{10}$ alkyl, trifluoromethyl, cyanoethyloxy, methoxy, ethoxy, t-butoxy, allyloxy, 9-fluorenylmethoxy, 2-(trimethylsilyl)-ethoxy, 2,2,2-trichloroethoxy, benzyloxy, butyryl, iso-butyryl, phenyl or aryl;

$R_5$ is hydrogen, a nitrogen protecting group or —T—L,
$R_{5a}$ is hydrogen, a nitrogen protecting group or —T—L,
T is a bond or a linking moiety;
L is a chemical functional group, a conjugate group or a solid support material;

each $R_6$ and $R_7$ is, independently, H, a nitrogen protecting group, substituted or unsubstituted $C_1$–$C_{10}$ alkyl, substituted or unsubstituted $C_2$–$C_{10}$ alkenyl, substituted or unsubstituted $C_2$–$C_{10}$ alkynyl, wherein said substitution is hydroxyl, amino, alkoxy, carboxy, benzyl, phenyl, nitro, thiol, thioalkoxy, halogen, alkyl, aryl, alkenyl, alkynyl; $NH_3^+$, /$N(R_{14})(R_{15})$, guanidino or acyl where said acyl is an acid amide or an ester;

or $R_6$ and $R_7$, together, are a nitrogen protecting group, are joined in a ring structure that optionally includes an additional heteroatom selected from N and O or are a chemical functional group;

each $R_{14}$ and $R_{15}$ is, independently, H, $C_1$–$C_{10}$ alkyl, a nitrogen protecting group, or $R_{14}$ and $R_{15}$, together, are a nitrogen protecting group;

or $R_{14}$ and $R_{15}$ are joined in a ring structure that optionally includes an additional heteroatom selected from N and O;

$Z_4$ is OX, SX or $N(X)_2$;

each X is, independently, H, $C_1$–$C_8$ alkyl, $C_1$–$C_8$ haloalkyl, C(=NH)N(H)$R_{16}$, C(=O)N(H)$R_{16}$ or OC(=O)N(H)$R_{16}$;

$R_{16}$ is H or $C_1$–$C_8$ alkyl;

$Z_1$, $Z_2$ and $Z_3$ comprise a ring system having from about 4 to about 7 carbon atoms or having from about 3 to about 6 carbon atoms and 1 or 2 heteroatoms wherein said heteroatoms are selected from oxygen, nitrogen and sulfur and wherein said ring system is aliphatic, unsaturated aliphatic, aromatic, or saturated or unsaturated heterocyclic;

$Z_5$ is alkyl or haloalkyl having 1 to about 10 carbon atoms, alkenyl having 2 to about 10 carbon atoms, alkynyl having 2 to about 10 carbon atoms, aryl having 6 to about 14 carbon atoms, $N(R_5)(R_6)$ $OR_5$, halo, $SR_5$ or CN;

each $q_1$ is, independently, an integer from 1 to 10;
each $q_2$ is, independently, 0 or 1;
$q_3$ is 0 or an integer from 1 to 10;
$q_4$ is an integer from 1 to 10;
$q_5$ is from 0, 1 or 2; and provided that when $q_3$ is 0, $q_4$ is greater than 1. Preferred sugar substituent groups include: OH; F; O—, S—, or N-alkyl; O—, S—, or N-alkenyl; O—, S— or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_2CH_3]_2$, where n and m are from 1 to about 10. Other preferred oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—$CH_2CH_2OCH_3$, also known as 2'-O-(2-1 methoxyethyl) or 2'-MOE) (Martin et al., *Helv. Chim. Acta*, 1995, 78, 486–504) i.e., an alkoxyalkoxy group. A further preferred modification includes 2'-dimethylaminooxyethoxy, i.e., a $O(CH_2)_2ON(CH_3)_2$ group, also known as 2'-DMAOE, as described in examples hereinbelow, and 2'-dimethylaminoethoxyethoxy (also known in the art as 2'-O-dimethylaminoethoxyethyl or 2'-DMAEOE), i.e., 2'-O —$CH_2$—O—$CH_2$—$N(CH_3)_2$, also described in examples herein below.

Other preferred sugar substituent groups include: 2'-methoxy (2'-O—$CH_3$), 2'-aminopropoxy (2'-$OCH_2CH_2CH_2NH_2$), 2'-allyl (2'-$CH_2$—CH=$CH_2$), 2'-O-allyl (2'-O—$CH_2$—CH=$CH_2$) and 2'-fluoro (2'-F). The 2'-modification may be in the arabino (up) position or ribo (down) position. A preferred 2'-arabino modification is 2'-F. Similar modifications may also be made at other positions on the oligonucleotide, particularly the 3' position of the sugar on the 3' terminal nucleotide or in 2'–5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,18,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, certain of which are commonly owned with the instant application, and each of which is herein incorporated by reference in its entirety.

A further preferred modification of the sugar moiety is a locked nucleic acid structure (LNA) in which the 2'-hydroxyl group is linked to the 3' or 4' carbon atom of the sugar ring thereby forming a bicyclic sugar moiety. The linkage is preferably a metheyne (—$CH_2$—)$_n$ group bridging the 2' oxygen atom and the 4' carbon atom wherein n is 1 or 2. LNAs and preparation thereof are described in WO 98/39352 and WO 99/14226.

Oligonucleotides may also include nucleobase (often referred to in the art simply as "base" or "heterocyclic base moiety") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me—C), 5-hydroxymethyl cytosine, xanthine, hypoxanthine, 2-amninoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 92-aminoethoxy)-H-pyrimido[5,4-b][1,4]benzoxazin-2 (3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687, 808, those disclosed in *The Concise Encyclopedia Of Polymer Science And Engineering*, pages 858–859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289–302, Crooke, S. T. and Lebleu, B., ed., CRC Press, 1993. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6–1.2° C. (Sanghvi, Y. S., Crooke, S. T. and Lebleu, B., eds., *Antisense Research and Applications*, CRC Press, Boca Raton, 1993, pp. 276–278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,645,985; 5,830,653; 5,763,588; 6,005,096; and 5,681,941, certain of which are commonly owned with the instant application, and each of which is herein incorporated by reference, and U.S. Pat. No. 5,750,692, which is commonly owned with the instant application and also herein incorporated by reference.

Another modification of the oligonucleotides of the invention involves chemically linking to the oligonucleotide one or more moieties or conjugates which enhance the activity, cellular distribution or cellular uptake of the oligonucleotide. The compounds of the invention can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugates groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve oligomer uptake, enhance oligomer resistance to degradation, and/or strengthen sequence-specific hybridization with RNA. Groups that enhance the pharmacokinetic properties, in the context of this invention, include groups that improve oligomer uptake, distribution, metabolism or excretion. Representative conjugate groups are disclosed in International Patent Application PCT/US92/09196, filed Oct. 23, 1992 the entire disclosure of which is incorporated herein by reference. Conjugate moieties include but are not limited to lipid moieties such as a cholesterol moiety (Letsinger et al., *Proc. Natl. Acad. Sci. USA*, 1989, 86, 6553–6556), cholic acid (Manoharan et al., *Bioorg. Med. Chem. Let.*, 1994, 4, 1053–1060), a thioether, e.g., hexyl-S-tritylthiol (Manoharan et al., *Ann. N.Y. Acad. Sci.*, 1992, 660, 306–309; Manoharan et al., *Bioorg. Med. Chem. Let.*, 1993, 3, 2765–2770), a thiocholesterol (Oberhauser et al., *Nucl. Acids Res.*, 1992, 20, 533–538), an aliphatic chain, e.g., dodecandiol or undecyl residues (Saison-Behmoaras et al., *EMBO J.*, 1991, 10,1111–1118; Kabanov et al., *FEBS Lett.*, 1990, 259, 327–330; Svinarchuk et al., *Biochimie*, 1993, 75, 49–54), a phospholipid, e.g., di-hexadecyl-rac-glycerol or triethylammonium 1,2-di-O-hexadecyl-rac-glycero-3-H-phosphonate (Manoharan et al., *Tetrahedron Lett.*, 1995, 36, 3651–3654; Shea et al., *Nucl. Acids Res.*, 1990, 18, 3777–3783), a polyamine or a polyethylene glycol chain (Manoharan et al., *Nucleosides & Nucleotides*, 1995, 14, 969–973), or adamantane acetic acid (Manoharan et al., *Tetrahedron Lett.*, 1995, 36, 3651–3654), a palmityl moiety (Mishra et al., *Biochim. Biophys. Acta*, 1995, 1264, 229–237), or an octadecylamine or hexylamino-carbonyl-oxycholesterol moiety (Crooke et al., *J. Pharmacol. Exp. Ther.*, 1996, 277, 923–937. Oligonucleotides of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130 (filed Jun. 15, 1999) which is incorporated herein by reference in its entirety.

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, certain of which are commonly owned with the instant application, and each of which is herein incorporated by reference.

It is not necessary for all positions in a given compound to be uniformly modified, and in fact more than one of the aforementioned modifications may be incorporated in a single compound or even at a single nucleoside within an oligonucleotide. The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

Chimeric antisense compounds of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety.

The oligomeric compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

The compounds of the invention may also be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption. Representative United States patents that teach the preparation of such uptake, distribution and/or absorption assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

The antisense compounds of the invention encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl) phosphate] derivatives according to the methods disclosed in WO 93/24510 to Gosselin et al., published Dec. 9, 1993 or in WO 94/26764 and U.S. Pat. No. 5,770,713 to Imbach et al.

The term "pharmaceutically acceptable salts" refers to physiologically and pharmaceutically acceptable salts of the compounds of the invention: i.e., salts that retain the desired biological activity of the parent compound and do not impart undesired toxicological effects thereto.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge et al., "Pharmaceutical Salts," *J. of Pharma Sci.,* 1977, 66, 1–19). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention. As used herein, a "pharmaceutical addition salt" includes a pharmaceutically acceptable salt of an acid form of one of the components of the compositions of the invention. These include organic or inorganic acid salts of the amines. Preferred acid salts are the hydrochlorides, acetates, salicylates, nitrates and phosphates. Other suitable pharmaceutically acceptable salts are well known to those skilled in the art and include basic salts of a variety of inorganic and organic acids, such as, for example, with inorganic acids, such as for example hydrochloric acid, hydrobromic acid, sulfuric acid or phosphoric acid; with organic carboxylic, sulfonic, sulfo or phospho acids or N-substituted sulfamic acids, for example acetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid; and with amino acids, such as the 20 alpha-amino acids involved in the synthesis of proteins in nature, for example glutamic acid or aspartic acid, and also with phenylacetic acid, methanesulfonic acid, ethanesulfonic acid, 2-hydroxyethanesulfonic acid, ethane-1,2-disulfonic acid, benzenesulfonic acid, 4-methylbenzenesulfonic acid, naphthalene-2-sulfonic acid, naphthalene-1,5-disulfonic acid, 2- or 3-phosphoglycerate, glucose-6-phosphate, N-cyclohexylsulfamic acid (with the formation of cyclamates), or with other acid organic compounds, such as ascorbic acid. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible.

For oligonucleotides, preferred examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

The antisense compounds of the present invention can be utilized for diagnostics, therapeutics, prophylaxis and as research reagents and kits. For therapeutics, an animal, preferably a human, suspected of having a disease or disorder which can be treated by modulating the expression of Hck is treated by administering antisense compounds in accordance with this invention. The compounds of the invention can be utilized in pharmaceutical compositions by adding an effective amount of an antisense compound to a suitable pharmaceutically acceptable diluent or carrier. Use of the antisense compounds and methods of the invention may also be useful prophylactically, e.g., to prevent or delay infection, inflammation or tumor formation, for example.

The antisense compounds of the invention are useful for research and diagnostics, because these compounds hybridize to nucleic acids encoding Hck, enabling sandwich and other assays to easily be constructed to exploit this fact. Hybridization of the antisense oligonucleotides of the invention with a nucleic acid encoding Hck can be detected by means known in the art. Such means may include conjugation of an enzyme to the oligonucleotide, radiolabelling of the oligonucleotide or any other suitable detection means. Kits using such detection means for detecting the level of Hck in a sample may also be prepared.

The present invention also includes pharmaceutical compositions and formulations which include the antisense compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful. Preferred topical formulations include those in which the oligonucleotides of the invention are in admixture with a topical delivery agent such as lipids, liposomes, fatty acids, fatty acid esters, steroids, chelating agents and surfactants. Preferred lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA). Oligonucleotides of the invention may be encapsulated within liposomes or may form complexes thereto, in particular to cationic liposomes. Alternatively, oligonucleotides may be complexed to lipids, in particular to cationic lipids. Preferred fatty acids and esters include but are not limited arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a $C_{1-10}$ alkyl ester (e.g. isopropylmyristate IPM), monoglyceride, diglyceride or pharmaceutically acceptable salt thereof. Topical formulations are described in detail in U.S. patent application Ser. No. 09/315,298 filed on May 20, 1999 which is incorporated herein by reference in its entirety.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Preferred oral formulations are those in which oligonucleotides of the invention are administered in conjunction with one or more penetration enhancers surfactants and chelators. Preferred surfactants include fatty acids and/or esters or salts thereof, bile acids and/or salts thereof. Prefered bile acids/salts include chenodeoxycholic acid (CDCA) and ursodeoxychenodeoxycholic acid (UDCA), cholic acid, dehydrocholic acid, deoxycholic acid, glucholic acid, glycholic acid, glycodeoxycholic acid, taurocholic acid, taurodeoxycholic acid, sodium tauro-24,25-dihydro-fusidate, sodium glycodihydrofusidate. Prefered fatty acids include arachidonic acid, undecanoic acid, oleic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1 dodecylazacycloheptan-2-one, an acylcarnitine, an acylcholine, or a monoglyceride, a diglyceride or a pharmaceutically acceptable salt thereof (e.g. sodium). Also prefered are combinations of penetration enhancers, for example, fatty acids/salts in combination with bile acids/salts. A particularly prefered combination is the sodium salt of lauric acid, capric acid and UDCA. Further penetration enhancers include polyoxyethylene-9-lauryl ether, polyoxyethylene-20-cetyl ether. Oligonucleotides of the invention may be delivered orally in granular form including sprayed dried particles, or complexed to form micro or nanoparticles. Oligonucleotide complexing agents include poly-amino acids; polyimines; polyacrylates; polyalkylacrylates, polyoxethanes, polyalkylcyanoacrylates; cationized gelatins, albumins, starches, acrylates, polyethyleneglycols (PEG) and starches;

polyalkylcyanoacrylates; DEAE-derivatized polyimines, pollulans, celluloses and starches. Particularly preferred complexing agents include chitosan, N-trimethylchitosan, poly-L-lysine, polyhistidine, polyornithine, polyspermines, protamine, polyvinylpyridine, polythiodiethylaminomethylethylene P(TDAE), polyaminostyrene (e.g. p-amino), poly(methylcyanoacrylate), poly (ethylcyanoacrylate), poly(butylcyanoacrylate), poly (isobutylcyanoacrylate), poly(isohexylcynaoacrylate), DEAE-methacrylate, DEAE-hexylacrylate, DEAE-acrylamide, DEAE-albumin and DEAE-dextran, polymethylacrylate, polyhexylacrylate, poly(D,L- lactic acid), poly(DL-lactic-co-glycolic acid (PLGA), alginate, and polyethyleneglycol (PEG). Oral formulations for oligonucleotides and their preparation are described in detail in U.S. application Ser. Nos. 08/886, 829 (filed Jul. 1, 1997), 09/108,673 (filed Jul. 1, 1998), 09/256,515 (filed Feb. 23, 1999), 09/082,624 (filed May 21, 1998) and 09/315,298 (filed May 20, 1999) each of which is incorporated herein by reference in their entirety.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient (s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product. The preparation of such compositions and formulations is generally known to those skilled in the pharmaceutical and formulation arts and may be applied to the formulation of the compositions of the present invention.

The compositions of the present invention may be prepared and formulated as emulsions. Emulsions are typically heterogenous systems of one liquid dispersed in another in the form of droplets usually exceeding 0.1 $\mu$m in diameter. (Idson, in *Pharmaceutical Dosage Forms*, Lieberman, Rieger and Banker (Eds.), 1988, Marcel Dekker, Inc., New York, N.Y., volume 1, p. 199; Rosoff, in *Pharmaceutical Dosage Forms*, Lieberman, Rieger and Banker (Eds.), 1988, Marcel Dekker, Inc., New York, N.Y., Volume 1, p. 245; Block in *Pharmaceutical Dosage Forms*, Lieberman, Rieger and Banker (Eds.), 1988, Marcel Dekker, Inc., New York, N.Y., volume 2, p. 335; Higuchi et al., in *Remington's Pharmaceutical Sciences*, Mack Publishing Co., Easton, Pa., 1985, p. 301). Emulsions are often biphasic systems comprising of two immiscible liquid phases intimately mixed and dispersed with each other. In general, emulsions may be either water-in-oil (w/o) or of the oil-in-water (o/w) variety. When an aqueous phase is finely divided into and dispersed as minute droplets into a bulk oily phase the resulting composition is called a water-in-oil (w/o) emulsion. Alternatively, when an oily phase is finely divided into and dispersed as minute droplets into a bulk aqueous phase the resulting composition is called an oil-in-water (o/w) emulsion. Emulsions may contain additional components in addition to the dispersed phases and the active drug which may be present as a solution in either the aqueous phase, oily phase or itself as a separate phase. Pharmaceutical excipients such as emulsifiers, stabilizers, dyes, and anti-oxidants may also be present in emulsions as needed. Pharmaceutical emulsions may also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion may be a semisolid or a solid, as is the case of emulsion-style ointment bases and creams. Other means of stabilizing emulsions entail the use of emulsifiers that may be incorporated into either phase of the emulsion. Emulsifiers may broadly be classified into four categories: synthetic surfactants, naturally occurring emulsifiers, absorption bases, and finely dispersed solids (Idson, in *Pharmaceutical Dosage Forms*, Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (Rieger, in *Pharmaceutical Dosage Forms,* Lieberman, Rieger and Banker (Eds.), 1988, Marcel Dekker, Inc., New York, N.Y., volume 1, p. 285; Idson, in *Pharmaceutical Dosage Forms*, Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants may be classified into different classes based on the nature of the hydrophilic group: nonionic, anionic, cationic and amphoteric (Rieger, in *Phar-* maceutical Dosage Forms, Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives and antioxidants (Block, in *Pharmaceutical Dosage Forms*, Lieberman, Rieger and Banker (Eds.), 1988, Marcel Dekker, Inc., New York, N.Y., volume 1, p. 335; Idson, in *Pharmaceutical Dosage Forms*, Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that may readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used may be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The application of emulsion formulations via dermatological, oral and parenteral routes and methods for their manufacture have been reviewed in the literature (Idson, in *Pharmaceutical Dosage Forms*, Lieberman, Rieger and Banker (Eds.), 1988, Marcel Dekker, Inc., New York, N.Y., volume 1, p. 199). Emulsion formulations for oral delivery have been very widely used because of reasons of ease of formulation, efficacy from an absorption and bioavailability standpoint. (Rosoff, in *Pharmaceutical Dosage Forms*, Lieberman, Rieger and Banker (Eds.), 1988, Marcel Dekker, Inc., New York, N.Y., volume 1, p. 245; Idson, in *Pharmaceutical Dosage Forms*, Lieberman, Rieger and Banker (Eds.), 1988, Marcel Dekker, Inc., New York, N.Y., volume 1, p. 199). Mineral-oil base laxatives, oil-soluble vitamins and high fat nutritive preparations are among the materials that have commonly been administered orally as o/w emulsions.

In one embodiment of the present invention, the compositions of oligonucleotides and nucleic acids are formulated as microemulsions. A microemulsion may be defined as a system of water, oil and amphiphile which is a single optically isotropic and thermodynamically stable liquid solution (Rosoff, in *Pharmaceutical Dosage Forms*, Lieberman, Rieger and Banker (Eds.), 1988, Marcel Dekker, Inc., New York, N.Y., volume 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: *Controlled Release of Drugs: Polymers and Aggregate Systems*, Rosoff, M., Ed., 1989, VCH Publishers, New York, pages 185–215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in *Remington's Pharmaceutical Sciences*, Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (Rosoff, in *Pharmaceutical Dosage Forms*, Lieberman, Rieger and Banker (Eds.), 1988, Marcel Dekker, Inc., New York, N.Y., volume 1, p. 245; Block, in *Pharmaceutical Dosage Forms*, Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), decaglycerol decaoleate (DAO750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions may, however, be prepared without the use of cosurfactants and alcohol-free self-emulsifying microemulsion systems are known in the art. The aqueous phase may typically be, but is not limited to, water, an aqueous solution of the drug, glycerol, PEG300, PEG400, polyglycerols, propylene glycols, and derivatives of ethylene glycol. The oil phase may include, but is not limited to, materials such as Captex 300, Captex 355, Capmul MCM, fatty acid esters, medium chain (C8–C12) mono, di, and tri-glycerides, polyoxyethylated glyceryl fatty acid esters, fatty alcohols, polyglycolized glycerides, saturated polyglycolized C8–C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (Constantinides et al., *Pharmaceutical Research*, 1994, 11, 1385–1390; Ritschel, *Meth. Find. Exp. Clin. Pharmacol.*, 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (Constantinides et al., *Pharmaceutical Research*, 1994, 11, 1385; Ho et al., *J. Pharm. Sci.*, 1996, 85, 138–143). Often microemulsions may form spontaneously when their components are brought together at ambient temperature. This may be particularly advantageous when formulating thermolabile drugs, peptides or oligonucleotides. Microemulsions have also been effective in the transdermal delivery of active components in both cosmetic and pharmaceutical applications. It is expected that the microemulsion compositions and formulations of the present invention will facilitate the increased systemic absorption of oligonucleotides and nucleic acids from the gastrointestinal tract, as well as improve the local cellular uptake of oligonucleotides and nucleic acids within the gastrointestinal tract, vagina, buccal cavity and other areas of administration.

Microemulsions of the present invention may also contain additional components and additives such as sorbitan monostearate (Grill 3), Labrasol, and penetration enhancers to improve the properties of the formulation and to enhance the absorption of the oligonucleotides and nucleic acids of the present invention. Penetration enhancers used in the microemulsions of the present invention may be classified as belonging to one of five broad categories—surfactants, fatty acids, bile salts, chelating agents, and non-chelating non-surfactants (Lee et al., *Critical Reviews in Therapeutic Drug Carrier Systems*, 1991, p. 92). Each of these classes has been discussed above.

There are many organized surfactant structures besides microemulsions that have been studied and used for the formulation of drugs. These include monolayers, micelles, bilayers and vesicles. Vesicles, such as liposomes, have attracted great interest because of their specificity and the duration of action they offer from the standpoint of drug delivery. As used in the present invention, the term "liposome" means a vesicle composed of amphiphilic lipids arranged in a spherical bilayer or bilayers.

Liposomes are unilamellar or multilamellar vesicles which have a membrane formed from a lipophilic material and an aqueous interior. The aqueous portion contains the composition to be delivered. Cationic liposomes possess the advantage of being able to fuse to the cell wall. Non-cationic liposomes, although not able to fuse as efficiently with the cell wall, are taken up by macrophages in vivo.

In order to cross intact mammalian skin, lipid vesicles must pass through a series of fine pores, each with a diameter less than 50 nm, under the influence of a suitable transdermal gradient. Therefore, it is desirable to use a liposome which is highly deformable and able to pass through such fine pores.

Further advantages of liposomes include; liposomes obtained from natural phospholipids are biocompatible and biodegradable; liposomes can incorporate a wide range of water and lipid soluble drugs; liposomes can protect encapsulated drugs in their internal compartments from metabolism and degradation (Rosoff, in *Pharmaceutical Dosage Forms*, Lieberman, Rieger and Banker (Eds.), 1988, Marcel Dekker, Inc., New York, N.Y., volume 1, p. 245). Important considerations in the preparation of liposome formulations are the lipid surface charge, vesicle size and the aqueous volume of the liposomes.

Liposomes are useful for the transfer and delivery of active ingredients to the site of action. Because the liposomal membrane is structurally similar to biological membranes, when liposomes are applied to a tissue, the liposomes start to merge with the cellular membranes. As the merging of the liposome and cell progresses, the liposomal contents are emptied into the cell where the active agent may act.

Liposomal formulations have been the focus of extensive investigation as the mode of delivery for many drugs. There is growing evidence that for topical administration, liposomes present several advantages over other formulations. Such advantages include reduced side-effects related to high systemic absorption of the administered drug, increased accumulation of the administered drug at the desired target, and the ability to administer a wide variety of drugs, both hydrophilic and hydrophobic, into the skin.

Several reports have detailed the ability of liposomes to deliver agents including high-molecular weight DNA into the skin. Compounds including analgesics, antibodies, hormones and high-molecular weight DNAs have been administered to the skin. The majority of applications resulted in the targeting of the upper epidermis.

Liposomes fall into two broad classes. Cationic liposomes are positively charged liposomes which interact with the negatively charged DNA molecules to form a stable complex. The positively charged DNA/liposome complex binds to the negatively charged cell surface and is internalized in an endosome. Due to the acidic pH within the endosome, the liposomes are ruptured, releasing their contents into the cell cytoplasm (Wang et al., *Biochem. Biophys. Res. Commun.*, 1987, 147, 980–985).

Liposomes which are pH-sensitive or negatively-charged, entrap DNA rather than complex with it. Since both the DNA and the lipid are similarly charged, repulsion rather than complex formation occurs. Nevertheless, some DNA is entrapped within the aqueous interior of these liposomes pH-sensitive liposomes have been used to deliver DNA encoding the thymidine kinase gene to cell monolayers in culture. Expression of the exogenous gene was detected in the target cells (Zhou et al., *Journal of Controlled Release*, 1992, 19, 269–274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Several studies have assessed the topical delivery of liposomal drug formulations to the skin. Application of liposomes containing interferon to guinea pig skin resulted in a reduction of skin herpes sores while delivery of interferon via other means (e.g. as a solution or as an emulsion) were ineffective (Weiner et al., *Journal of Drug Targeting*, 1992, 2, 405–410). Further, an additional study tested the efficacy of interferon administered as part of a liposomal formulation to the administration of interferon using an aqueous system, and concluded that the liposomal formulation was superior to aqueous administration (du Plessis et al., *Antiviral Research*, 1992, 18, 259–265).

Non-ionic liposomal systems have also been examined to determine their utility in the delivery of drugs to the skin, in particular systems comprising non-ionic surfactant and cholesterol. Non-ionic liposomal formulations comprising Novasome™ I (glyceryl dilaurate/cholesterol/polyoxyethylene-10-stearyl ether) and Novasome™ II (glyceryl distearate/cholesterol/polyoxyethylene-10-stearyl ether) were used to deliver cyclosporin-A into the dermis of mouse skin. Results indicated that such non-ionic liposomal systems were effective in facilitating the deposition of cyclosporin-A into different layers of the skin (Hu et al. *S. T. P. Pharma. Sci.*, 1994, 4, 6,466).

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside $G_{M1}$, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., *FEBS Letters*, 1987, 223, 42; Wu et al., *Cancer Research*, 1993, 53, 3765). Various liposomes comprising one or more glycolipids are known in the art. Papahadjopoulos et al. (*Ann. N.Y. Acad. Sci.*, 1987, 507, 64) reported the ability of monosialoganglioside $G_{M1}$, galactocerebroside sulfate and phosphatidylinositol to improve blood half-lives of liposomes. These findings were expounded upon by Gabizon et al. (*Proc. Natl. Acad. Sci. U.S.A.*, 1988, 85, 6949). U.S. Pat. No. 4,837,028 and WO 88/04924, both to Allen et al., disclose liposomes comprising (1) sphingomyelin and (2) the ganglioside $G_{M1}$ or a galactocerebroside sulfate ester. U.S. Pat. No. 5,543,152 (Webb et al.) discloses liposomes comprising sphingomyelin. Liposomes comprising 1,2-sn-dimyristoylphosphatidylcholine are disclosed in WO 97/13499 (Lim et al.).

Many liposomes comprising lipids derivatized with one or more hydrophilic polymers, and methods of preparation thereof, are known in the art. Sunamoto et al. (*Bull. Chem. Soc. Jpn.*, 1980, 53, 2778) described liposomes comprising a nonionic detergent, $2C_{12}15G$, that contains a PEG moiety. Illum et al. (*FEBS Lett.*, 1984, 167, 79) noted that hydrophilic coating of polystyrene particles with polymeric glycols results in significantly enhanced blood half-lives. Synthetic phospholipids modified by the attachment of carboxylic groups of polyalkylene glycols (e.g., PEG) are described by Sears (U.S. Pat. Nos. 4,426,330 and 4,534,899). Klibanov et al. (*FEBS Let.*, 1990, 268, 235) described experiments demonstrating that liposomes comprising phosphatidylethanolamine (PE) derivatized with PEG or PEG stearate have significant increases in blood circulation half-lives. Blume et al. (*Biochimica et Biophysica Acta*, 1990, 1029, 91) extended such observations to other PEG-derivatized phospholipids, e.g., DSPE-PEG, formed from the combination of distearoylphosphatidylethanolamine (DSPE) and PEG. Liposomes having covalently bound PEG moieties on their external surface are described in European Patent No. EP 0 445 131 B1 and WO 90/04384 to Fisher. Liposome compositions containing 1–20 mole percent of PE derivatized with PEG, and methods of use thereof, are described by Woodle et al. (U.S. Pat. Nos. 5,013,556 and 5,356,633) and Martin et al. (U.S. Pat. No. 5,213,804 and European Patent No. EP 0 496 813 B1). Liposomes comprising a number of other lipid-polymer conjugates are disclosed in WO 91/05545 and U.S. Pat. No. 5,225,212 (both to Martin et al.) and in WO 94/20073 (Zalipsky et al.) Liposomes comprising PEG-modified ceramide lipids are described in WO 96/10391 (Choi et al.). U.S. Pat. Nos. 5,540,935 (Miyazaki et al.) and 5,556,948 (Tagawa et al.) describe PEG-containing liposomes that can be further derivatized with functional moieties on their surfaces.

A limited number of liposomes comprising nucleic acids are known in the art. WO 96/40062 to Thierry et al. discloses methods for encapsulating high molecular weight nucleic acids in liposomes. U.S. Pat. No. 5,264,221 to Tagawa et al. discloses protein-bonded liposomes and asserts that the contents of such liposomes may include an antisense RNA. U.S. Pat. No. 5,665,710 to Rahman et al. describes certain methods of encapsulating oligodeoxynucleotides in liposomes. WO 97/04787 to Love et al. discloses liposomes comprising antisense oligonucleotides targeted to the raf gene.

Transfersomes are yet another type of liposomes, and are highly deformable lipid aggregates which are attractive candidates for drug delivery vehicles. Transfersomes may be described as lipid droplets which are so highly deformable that they are easily able to penetrate through pores which are smaller than the droplet. Transfersomes are adaptable to the environment in which they are used, e.g. they are self-optimizing (adaptive to the shape of pores in the skin), self-repairing, frequently reach their targets without fragmenting, and often self-loading. To make transfersomes it is possible to add surface edge-activators, usually surfactants, to a standard liposomal composition. Transfersomes have been used to deliver serum albumin to the skin. The transfersome-mediated delivery of serum albumin has been shown to be as effective as subcutaneous injection of a solution containing serum albumin.

Surfactants find wide application in formulations such as emulsions (including microemulsions) and liposomes. The most common way of classifying and ranking the properties of the many different types of surfactants, both natural and synthetic, is Iby the use of the hydrophile/lipophile balance (HLB). The nature of the hydrophilic group (also known as the "head") provides the most useful means for categorizing the different surfactants used in formulations (Rieger, in *Pharmaceutical Dosage Forms*, Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid su ch as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in *Pharmaceutical Dosage Forms*, Marcel Dekker, Inc., New York, N.Y., 1988, p. 285).

In one embodiment, the present invention employs various penetration enhancers to effect the efficient delivery of nucleic acids, particularly oligonucleotides, to the skin of animals. Most drugs are present in solution in both ionized and nonionized forms. However, usually only lipid soluble or lipophilic drugs readily cross cell membranes. It has been discovered that even non-lipophilic drugs may cross cell membranes if the membrane to be crossed is treated with a penetration enhancer. In addition to aiding the diffusion of non-lipophilic drugs across cell membranes, penetration enhancers also enhance the permeability of lipophilic drugs.

Penetration enhancers may be classified as belonging to one of five broad categories, i.e., surfactants, fatty acids, bile salts, chelating agents, and non-chelating non-surfactants (Lee et al., *Critical Reviews in Therapeutic Drug Carrier Systems*, 1991, p.92). Each of the above mentioned classes of penetration enhancers are described below in greater detail.

In connection with the present invention, surfactants (or "surface-active agents") are chemical entities which, when dissolved in an aqueous solution, reduce the surface tension of the solution or the interfacial tension between the aqueous solution and another liquid, with the result that absorption of oligonucleotides through the mucosa is enhanced. In addition to bile salts and fatty acids, these penetration enhancers include, for example, sodium lauryl sulfate, polyoxyethylene-9-lauryl ether and polyoxyethylene-20-cetyl ether) (Lee et al., *Critical Reviews in Therapeutic Drug Carrier Systems*, 1991, p.92); and perfluorochemical emulsions, such as FC-43. Takahashi et al., *J. Pharm. Pharmacol.*, 1988, 40, 252).

Fatty acids: Various fatty acids and their derivatives which act as penetration enhancers include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glycerol 1-monocaprate, 1-dodecylazacycloheptan-2-one, acylcarnitines, acylcholines, $C_{1-10}$ alkyl esters thereof (e.g., methyl, isopropyl and t-butyl), and mono- and di-glycerides thereof (i.e., oleate, laurate, caprate, myristate, palmitate, stearate, linoleate, etc.) (Lee et al., *Critical Reviews in Therapeutic Drug Carrier Systems*, 1991, p.92; Muranishi, *Critical Reviews in Therapeutic Drug Carrier Systems*, 1990, 7, 1–33; El Hariri et al., J. Pharm. Pharmacol., 1992, 44, 651–654).

The physiological role of bile includes the facilitation of dispersion and absorption of lipids and fat-soluble vitamins (Brunton, Chapter 38 in: Goodman & Gilman's *The Pharmacological Basis of Therapeutics*, 9th Ed., Hardman et al. Eds., McGraw-Hill, New York, 1996, pp. 934–935). Various natural bile salts, and their synthetic derivatives, act as penetration enhancers. Thus the term "bile salts" includes any of the naturally occurring components of bile as well as any of their synthetic derivatives. The bile salts of the invention include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (sodium chenodeoxycholate), ursodeoxycholic acid (UDCA), sodium tauro-24,25-dihydro-fusidate (STDHF), sodium glycodihydrofusidate and polyoxyethylene-9-lauryl ether (POE) (Lee et al., *Critical Reviews in Therapeutic Drug Carrier Systems*, 1991, page 92; Swinyard, Chapter 39 *In: Remington's Pharmaceutical Sciences*, 18th Ed., Gennaro, ed., Mack Publishing Co., Easton, Pa., 1990, pages 782–783; Muranishi, *Critical Reviews in Therapeutic Drug Carrier Systems*, 1990, 7, 1–33; Yamamoto et al., *J. Pharm. Exp. Ther.*, 1992, 263, 25; Yamashita et al., *J. Pharm. Sci.*, 1990, 79, 579–583).

Chelating agents, as used in connection with the present invention, can be defined as compounds that remove metallic ions from solution by forming complexes therewith, with the result that absorption of oligonucleotides through the mucosa is enhanced. With regards to their use as penetration enhancers in the present invention, chelating agents have the added advantage of also serving as DNase inhibitors, as most characterized DNA nucleases require a divalent metal ion for catalysis and are thus inhibited by chelating agents (Jarrett, *J. Chromatogr.*, 1993, 618, 315–339). Chelating agents of the invention include but are not limited to disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enanunes)(Lee et al., *Critical Reviews in Therapeutic Drug Carrier Systems*, 1991, page 92; Muranishi, *Critical Reviews in Therapeutic Drug Carrier Systems*, 1990, 7, 1–33; Buur et al., *J Control Rel.*, 1990, 14, 43–51).

As used herein, non-chelating non-surfactant penetration enhancing compounds can be defined as compounds that demonstrate insignificant activity as chelating agents or as surfactants but that nonetheless enhance absorption of oligonucleotides through the alimentary mucosa (Muranishi, *Critical Reviews in Therapeutic Drug Carrier Systems*, 1990, 7, 1–33). This class of penetration enhancers include, for example, unsaturated cyclic ureas, 1-alkyl- and 1-alkenylazacyclo-alkanone derivatives (Lee et al., *Critical Reviews in Therapeutic Drug Carrier Systems*, 1991, page 92); and non-steroidal anti-inflammatory agents such as diclofenac sodium, indomethacin and phenylbutazone (Yamashita et al., *J. Pharm. Pharmacol.*, 1987, 39, 621–626).

Agents that enhance uptake of oligonucleotides at the cellular level may also be added to the pharmaceutical and other compositions of the present invention. For example, cationic lipids, such as lipofectin (Junichi et at, U.S. Pat. No. 5,705,188), cationic glycerol derivatives, and polycationic molecules, such as polylysine (Lollo et al., PCT Application WO 97/30731), are also known to enhance the cellular uptake of oligonucleotides.

Other agents may be utilized to enhance the penetration of the administered nucleic acids, including glycols such as ethylene glycol and propylene glycol, pyrrols such as 2-pyrrol, azones, and terpenes such as limonene and menthone.

Certain compositions of the present invention also incorporate carrier compounds in the formulation. As used herein, "carrier compound" or "carrier" can refer to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioate oligonucleotide in hepatic tissue can be reduced when it is coadministered with polyinosinic acid, dextran sulfate, polycytidic acid or 4-acetamido-4'isothiocyano-stilbene-2,2'-disulfonic acid (Miyao et al., *Antisense Res. Dev.*, 1995, 5, 115–121; Takakura et al., *Antisense* & Nucl. Acid Drug Dev., 1996, 6, 177–183).

In contrast to a carrier compound, a "pharmaceutical carrier" or "excipient" is a pharmaceutically acceptable solvent, suspending agent or any other pharmacologically inert vehicle for delivering one or more nucleic acids to an animal. The excipient may be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc.).

Pharmaceutically acceptable organic or inorganic excipient suitable for non-parenteral administration which do not deleteriously react with nucleic acids can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

Formulations for topical administration of nucleic acids may include sterile and non-sterile aqueous solutions, non-aqueous solutions in common solvents such as alcohols, or solutions of the nucleic acids in liquid or solid oil bases. The solutions may also contain buffers, diluents and other suitable additives. Pharmaceutically acceptable organic or inorganic excipients suitable for non-parenteral administration which do not deleteriously react with nucleic acids can be used.

Suitable pharmaceutically acceptable excipients include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like.

The compositions of the present invention may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Aqueous suspensions may contain substances which increase the viscosity of the suspension including, for example, sodium carboxymethylcellulose, sorbitol and/or dextran. The suspension may also contain stabilizers.

Certain embodiments of the invention provide pharmaceutical compositions containing (a) one or more antisense compounds and (b) one or more other chemotherapeutic agents which function by a non-antisense mechanism. Examples of such chemotherapeutic agents include but are not limited to daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). See, generally, *The Merck Manual of Diagnosis and Therapy*, 15th Ed. 1987, pp. 1206–1228, Berkow et al., eds., Rahway, N.J. When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including but not limited to non-steroidal anti-inflammatory drugs and corticosteroids, and antiviral drugs, including but not limited to ribivirin, vidarabine, acyclovir and ganciclovir, may also be combined in compositions of the invention. See, generally, *The Merck Manual of Diagnosis and Therapy*, 15th Ed., Berkow et al., eds., 1987, Rahway, N.J., pages 2499–2506 and 46–49, respectively). Other non-antisense chemotherapeutic agents are also within the scope of this invention. Two or more combined compounds may be used together or sequentially.

In another related embodiment, compositions of the invention may contain one or more antisense compounds, particularly oligonucleotides, targeted to a first nucleic acid and one or more additional antisense compounds targeted to a second nucleic acid target. Numerous examples of antisense compounds are known in the art. Two or more combined compounds may be used together or sequentially.

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models. In general, dosage is from 0.01 ug to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 ug to 100 g per kg of body weight, once or more daily, to once every 20 years.

While the present invention has been described with specificity in accordance with certain of its preferred embodiments, the following examples serve only to illustrate the invention and are not intended to limit the same.

As will be recognized, the steps of certain processes of the present invention need not be performed any particular number of times or in any particular sequence. Additional objects, advantages, and novel features of this invention will become apparent to those skilled in the art upon examination of the following synthetic teachings and working examples which are intended to be illustrative of the present invention, and not limiting thereof.

EXAMPLES

Methods and Materials

2'-O-(Ethyl-2-sulfonic acid) sodiumsalt-N-3-(benzyloxy)methyl-5-methyluridine (B)

N-3-(benzyloxy)methyl-5-methyluridine A (41.57 g, 110 mmol) was dissolved in dry DMF (250 mL) and cooled to —45° C. NaH (4.8 g, 121 mmol) was added in three portions and the solution is warmed to 0° C. for one hour. The solution is cooled to −45° C. and solid 1,3,2-dioxathiolane 2,2-dioxide (15 g, 121 mmol) was added. The solution was allowed to warm to room temperature. The reaction was monitored by TLC for 5 hours which showed the reaction completed. The solvent was removed in vacuo and the residue was purified by silica gel column chromatography. The residue was applied to a column of silica gel and the product was eluted with a gradient of 5% to 10% methanol in dichloromethane. The appropriate fractions were collected and evaporated in vacuo to give 25.60 g (44%) of the title compound B, isolated as its sulfonic acid. The sulfates are produced in a 4 to 1 ratio as the 2' and 3' alkylated products. 2D $^1$H NMR TOCSY is used to identify the 2'-isomer. $^1$H NMR (DMSO-$d_6$) δ 1.81 (s, 3H), 3.55–3.78 (m, 6H), 3.88 (m, 1H, 4'H), 3.96(m, 1H), 4.13(m, 1H), 4.59(s, 2H), 5.08 (d, J=5.4 Hz 1H), 5.10 (t, J=6.3 Hz, 1H), (s, 2H), 5.84 (d, 1H), 7.28 (m, 5H), 7.93 (d, J=5.8 Hz, 6H). ESMS m/z 501.2 [M−Z].

2'-O-(Ethyl-2-sulfonic acid) sodium salt-5-methyluridine (C)

Compound B (5 g, 9.53 mM) was dissolved in a mixture of EtOH and AcOH (30 mL/30 mL). To this mixture palladium hydroxide (1 g) was added and placed on a Parr hydrogenation apparatus at 55 psi of $H_2$ overnight. The reaction was monitored by TLC (20% MeOH in dichloromethane). The solution was filtered through a bed of celite and concentrated to dryness in vacuo. The crude product C was used for the next step.

2'-O-[2-(thiomethyl)ethyl]-5-methyluridine (D)

Compound C (3.64 g, 9.53 mM, amount based on 100% conversion to N-3-(benzyloxy)methyl-5-methyluridine) was dissolved in 70 mL DMF and sodium thiomethoxide (6.68 g, 95.3 mM) was added as a solid. The reaction mixture was heated at 80° C. with monitoring by TLC (10% MeOH in $CH_2Cl_2$) showing completion at 18 hours. The reaction mixture was poured into water (50 mL) and extracted with ethyl acetate (50 mL). The organic phase was washed with brine (50 mL) dried over anhydrous $MgSO_4$, filtered and evaporated to dryness. The residue was purified by silica gel column chromatography and eluted with ethyl acetate to give compound D (1.61 g, 56%). $^1$H NMR (200 Mhz, $CDCl_3$) δ 1.92 (s, 3H), 2.15 (s, 3H), 2.69 (m, 3H), 3.20 (d, 2H), 3.64–3.88 (m, 2H), 4.05 (s, 3H), 4.21 (t, J=4.42 Hz, 1H), 4.35 (t, J=4.68 Hz 1H), 4.71 (s, 2H), 5.49 (s, 2H), 5.65 (d, J=5.48 Hz, 1H), 7.45 (s, 1H). MS (HRFAB$^+$) Calcd. for $C_{13}H_{20}N_2O_6SC_6{}^+$465.1515, found 465.1510.

5'-O-DMT-2'-O-methylthioethyl-5-methyluridine (E)

2'-O-methylthioethyl-5-methyluridine D (3.16 g, 9.53 mmol) was dissolved in pyridine (40 mL) and solid 4,4'-dimethoxytritylchloride (DMTCl) (3.23 g, 9.53 mmol) was added in one portion and the mixture was stirred overnight. The reaction was monitored by TLC (40% EtOAc in dichloromethane). The reaction mixture was partitioned between ethyl acetate and water (70 mL EtOAc/50 mL $H_2O$). The aqueous layer was extracted twice with EtOAc (25 mL each). The combined organic layers were washed with water (30 mL), brine (30 mL) and dried over $MgSO_4$. The organic layer was evaporated in vacuo to give a yellow residue. The residue was purified by silica gel column chromatography and eluted with 30% ethyl acetate in $CH_2Cl_2$. The appropriate fractions were collected and concentrated in vacuo to afford 2.05 g (34%) of the title compound E. $^1$H NMR (400 Mhz, $CDCl_3$) δ 1.42 (s, 3H), 2.03 (s, 3H), 2.74 (m, 2H), 3.13 (d, J=7.9 Hz, 1H), 3.46 (m, 2H), 3.81 (bs, 7H), 4.13 (m, 2H), 5.97 (d, 2.56 Hz, 1H), 6.83 (d, 8.76 Hz, 4H), 7.29 (m, 9H), 7.68 (s, 1H), 8.92 (bs, NH); MS (ES) m/z 633 [M+H]; Anal. Calcd for $C_{34}H_{38}N_2O_8S$+ 1.0 mol $H_2O$: C, 62.56; H, 6.18; N, 4.29 found: C, 62.87; H, 6.00; N, 4.10.

5'-O-DMT-2'-O-[2-(thiomethyl)ethyl]-5-methyluridine-3'-O-[(2-cyanoethyl) N,N-diisopropyl]phosphoramidite (F)

5'-O-DMT-2'-O-methylthioethyl-5-methyluridine E (1 g, 1.58 mM) was dissolved in dry dichloromethane (30 mL). To this solution was added; tetrazolide salt (297 mg, 1.73 mM) and 2-cyanoethyl N,N,N,N-tetraisopropylphosphorodiamidite (0.6 mL, 1.89 mM) is added dropwise to the reaction mixture. The reaction was complete by TLC (25% EtOAc in dichloromethane) after 20 h. The reaction was partitioned between EtOCc and saturated sodium bicarbonate (50 ml/50 mL). The organic layer was washed with brine, dried over $MgSO_4$, filtered and concentrated to a yellow foam. The product was purified by silica gel chromatography (25% EtOAc in dichloromethane). The appropriate fractions were collected and dried in vacuo. The residue was dissolved in a minimal amount of dry dichloromethane (5 mL) and 300 mL of hexane was added. The solvent was decanted from the precipitate. The white residue was then dried on the rotoevaporator and on high vacuum over $P_2O_5$ to give 1.10 g (83% yield) of title compound F. $^{31}P$ NMR (162 Mhz, $CDCl_3$) δ 151.17, 151.32.

5'-O-DMT-2'-O-[2-(thiomethyl)ethyl]-3'-O-succinyl-5-methyluridine (G)

Compound E (0.3 g, 0.47 mmol), was mixed with succinic anhydride (0.07 g, 0.71 mmol), DMAP (0.03 g, 0.24 mmol) and dried over $P_2O_5$ in vacuo overnight. The mixture was dissolved in $ClCH_2$—$CH_2Cl$ (1 mL), anhydrous triethylamine (0.33 mL, 2.36 mmol) was added and stirred at room temperature for 18 h. The reaction was monitored at room temperature by tlc (5% MeOH in $CH_2Cl_2$). Dichloromethane (30 mL) was added and the mixture was washed with ice cold aqueous citric acid (30 mL) and brine (30 mL). The organic phase was separated, dried over anhydrous $Na_2SO_4$ and evaporated to dryness in vacuo. The residue was purified by column chromatography by elution with 10% MeOH in $CH_2Cl_2$ containing 1% triethylamine to give compound G (0.20 g, 51%). $^1H$ NMR (400 Mhz, $CDCl_3$) δ 1.36 (s, 3H), 2.1 (s, 3H), 2.57–2.69 (m, 6H), 3.39 (d, J=2.14 Hz, 1H), 3.51–3.59 (m, 3H), 3.77 (m, 2H), 3.78 (s, 6H), 4.27 (brs, 1H), 4.31 (t, J=5.34 Hz, 1H), 5.35 (t, J=4.7 Hz, 1 H), 6.03 (d, J=5.34 Hz, 1H), 6.83 (d, J=8.97 Hz, 4H), 7.23–7.37 (m, 9H), 7.57 (s, 1H); $^{13}C$ NMR (100 Mhz, $CDCl_3$) δ 11.71, 30.07, 30.72, 33.51, 55.28, 62.52, 63.37, 70.59, 70.65, 80.41, 81.46, 86.97, 87.21, 111.32, 111.37, 127.24, 128.06, 128.17, 130.11, 135.06, 135.15, 135.34, 144.13, 150.36, 158.80, 163.63, 172.61, 176.36.

5'-O-DMT-2'-O-[2-(thiomethyl)ethyl]-5-methyluridine-3'-O-succinyl CPG (H)

Compound G was loaded on to CPG using standard methods and procedures for oligonucleotide synthesis with a loading capacity of 54 μmol/g.

Oligonucleotide Synthesis, Purification and Characterization

The amidite F was dissolved in anhydrous acetonitrile to 0.1 M and loaded onto an Expedite Nucleic Acid Synthesis system (Millipore 8909) to synthesize the oligonucleotides. The coupling efficiencies were greater than 98%. For the modified amidite 6, the coupling time was extended to 10 minutes and coupling was repeated twice. Oxidation of the phosphite intermediate was carried out using a 0.5 M solution of tert-BuOOH. All other steps in the protocol supplied by Millipore were used without modification. After completion of the synthesis, the CPG was suspended in aqueous ammonia (30%) at room temperature for 2 h to cleave the oligonucleotide. The CPG was filtered; the filtrate was then heated at 55° C. for 6 hours to effect the complete removal of the base-labile protecting groups. Ammonia was removed on a speed vac concentrator. The resulting product was purified by HPLC (Waters, C-4, 7.8×300 mm, A=50 mM triethylammonium acetate (TEAAc), pH=7, B=acetonitrile, 5 to 60% B in 55 min, Flow 2.5 mL/min., wavelength=260 nm). Detritylation with aqueous 80% acetic acid and evaporation followed by desalting by HPLC on a Waters C-4 column gave the 2'-modified oligonucleotides listed in Table I, which were analyzed by HPLC, capillary gel electrophoresis (CGE) and mass spectrometry.

Nuclease Stability Determination

Oligonucleotides, at a final concentration of 2 μM, were incubated with snake venom phosphodiesterase (0.005 IU/mL) in 50 mM Tris-HCl, pH 7.5, 8 mM $MgCl_2$ at 37° C. The total volume was 100 μL. At each time point 10 μL aliquots of each reaction mixture were placed in a 500 μL microfuge tubes and put in a boiling water bath for two minutes. The samples were then cooled on ice, quick spun to bring the entire volume to the bottom of the tube, and desalted on a Millipore 0.025 micron filter disk (Bedford, Mass.) that was floating in water in a 60 mm petrie dish. After 30–60 minutes on the membrane the sample was diluted with 200 μL distilled $H_2O$ and analyzed by gel-filled capillary electrophoresis. The oligonucleotide and metabolites were separated and analyzed using the Beckman P/ACE MDQ capillary electrophoresis instrument using a 100 μL ID 30 cm coated capillary (Beckman No. 477477) with eCAP ssDNA 100-R gel (Beckman No. 477621) and Tris-Borate Urea buffer (Beckman No. 338481). The samples were injected electrokinetically using a field strength of between 5–10 kV for a duration of between 5 and 10 seconds. Separation wash achieved at 40° C. with an applied voltage of 15 kV. The percentage of full length oligonucleotide was calculated by integration using Caesar v. 6 software (Senetec Software, New Jersey) followed by correction for differences in extinction coefficient for oligonucleotides of different length.

Procedure

Binding of Oligonucleotide to Human Serum Albumin

The 5'-end of each oligonucleotide was end labeled with $^{32}P$ using T4 polynucleotide kinase and standard procedures. Unincorporated label was removed using a G25 column and was confirmed by polyacrylamide gel electrophoresis. A fixed concentration of labeled oligonucleotide (50 nM) was incubated with increasing concentrations of human serum albumin (Fraction V, essentially Fatty Acid Free, essentially globulin free, Sigma) and incubated at 25° C. for one hour in PBS plus 0.1 mM EDTA and 0.005% Tween 80. Experiments with longer incubation times demonstrated that full equilibrium was achieved in less than one hour. Albumin-oligo mixtures were placed on the membranes (Ultrafree-MC 30 000, Millipore) and spun very gently at 3000 rpm (725×g) for 3–6 min until ~20% of the volume had passed through the filter. Aliquots of the initial mix (before filtration) and the filtrate were counted in the scintillation counter. After appropriate correction for background, concentration of free and bound oligonucleotide was calculated. The low concentration of oligonucleotide, relative to albumin, allows for detection of binding to only the tightest binding site on the albumin. Thus, fraction of oligonucleotide bound was plotted vs. total albumin concentration and data were fit to a two state model:

$$K_A + A \leftrightarrow (OA)$$

where O is unbound oligonucleotide, A is unbound albumin, (OA) is the oligonucleotide-albumin complex and $K_A$ is the equilibrium association constant.

Crystallization and Structure Determination

Optimal crystallization conditions for the modified decamer were screened by the sparse matrix crystallization technique, using the Hampton Research (Laguna Niguel, Calif.) nucleic acid mini screen. Crystals for data collection were grown by the hanging drop vapor diffusion method. Equal volumes of a 2 mM oligonucleotide solution in water and a buffer solution, containing 40 mM sodium cacodylate (pH 7.0), 80 mM potassium chloride, 12 mM spermine tetrahydrochloride and 10% (v/v) 2-methyl-2,4-pentanediol (MPD), were mixed and equilibrated against 1 mL 35% (v/v) MPD. Diffraction data to a maximum resolution of 1.2 Å were collected on a single flash-frozen (100 K) crystal at a wavelength of 1 Å on the 5-ID beamline at the Advanced Photon Source (DuPont-Northwestern-Dow Collaborative Access Team, Argonne, Ill.), using a MARCCD detector. Data were integrated and merged in the DENZO/SCALEPACK suite. The structure was solved by the molecular replacement method using the program AMORE. Crystallographic refinements were performed with the programs CNS and SHELX-97.

Example 1a

5'-O-DMT-2'-O-(2-methylthioethyl)-5-methyluridine-3'-[(2-cyanoethyl)-N,N-diisopropylphosphoramidite] (4)

Figure 1:
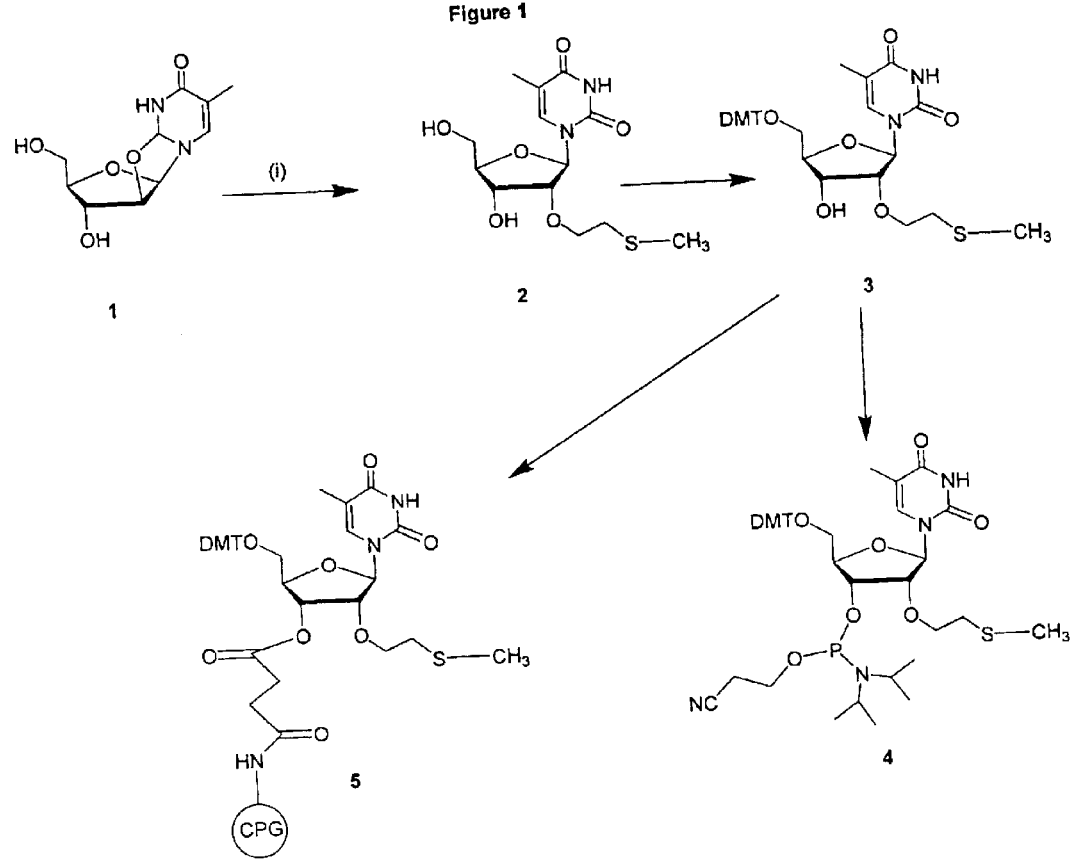
FIG. 1 depicts treatment of the 5'hydroxyl of 2'-O-[2-(thiomethyl)ethyl]-5-methyluridine 2 with 4,4'-dimethoxytrityl chloride (DMTCI) to give 5-O-DMT-2-O-[2-(thiomethyl)ethyl]-5-methyluridine followed by phosphitylation of compound 3 to form 5'-O-DMT-2'-O-(2-methylthioethyl)-5-methyluridine-3'-[(2-cyanoethyl)-N,N-diisopropylphosphoramidite] 4 or succinylation of compound 3 to form 5'-O-DMT-2=O-[2-(thiomethyl)ethyl]-3'-O-succinyl-5-methyluridine CPG 5.

Compound 4 is synthesized according to FIG. 1. 2,2'-anhydro-5-methyluridine 1 is heated at 160° C. with borate ester of S-methyl-2-thioethanol in S-methyl-2-thioethanol (Available from Aldrich, Milwaukee, Wis.) to yield the compound 2 which is selectively tritylated at 5'-position with DMTCI (4,4'-dimethoxytrityl chloride) and DMAP [4-(dimethylaminopyridine) in pyridine to yield the compound 3. Phosphitylation of the compound 3 at the 3'-position with N,N-diisopropylamine tetrazolide and 2-cyanoethyl-N,N,N,N-tetraisopropylphosphor-amidite yield the compound 4.

Example 1b

5'-O-DMT-2'-(2-methylthioethyl)-5-methyluridine-3'-O-succinyl CPG (5)

Compound 3 (FIG. 1) is treated with succinic anhydride and DMAP in dichloroethane at 60° C. to yield the 3'-O-succinyl derivative. This is coupled to CPG using 2-(1H-benzotriazole)-1-yl)-1.1.3.3-tetramethyluronium tetrafluorborate and N-methylmorpholine in DMF to yield support bound compound 5. (References: Kumar, P.; Sharma, A. K.; Sharma, P.; Garg, B. S.; Gupta, K. C. *Nucleosides and Nucleotides* 1996, 15, 879–888. (b) TBTU mediated synthesis of functionalized CPG synthesis; Bayer, E.; Bleicher, K.; Maier, M. A.; Z. *Naturforsch.* 1995, 50b, 1906–1100.)

Example 2a

5'-O-DMT-2'-O-(2-methylthioethyl)-N4-benzoyl-5-methylcytidine-3'-[(2-cyanoethyl)-N,N-diisopropylphosphoramidite] (8)

Figure 2:
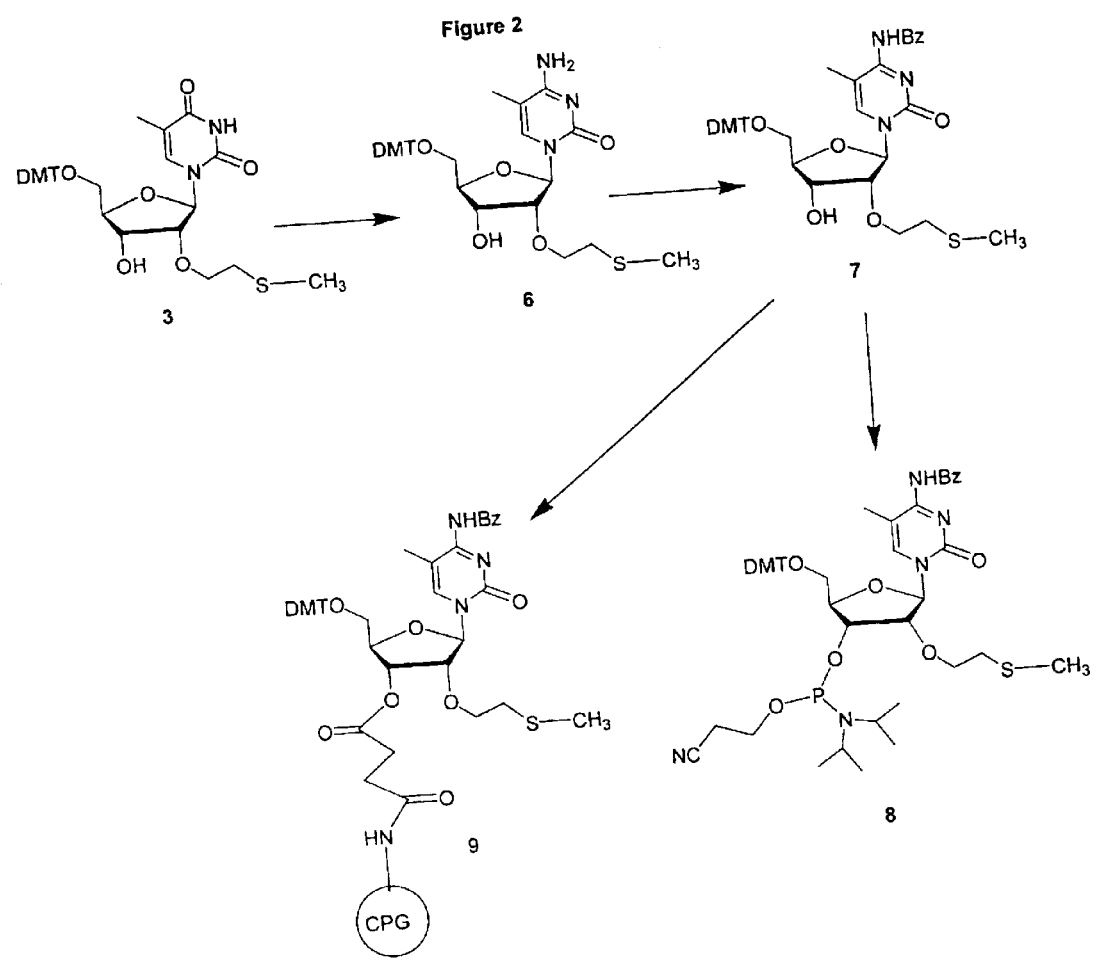
FIG. 2 depicts formation of 5'-O-DMT-2'-O-(2-methylthioethyl)-N4-benzoyl-5-methylcytidine-3'-[(2-cyanoethyl)-N,N-diisopropylphosphoramidite] 8 and 5'-O-DMT-2-(2-methylthioethyl)-N4-benzoyl-5-methylcytidine-3'-O-succinyl CPG 9.

Compound 8 is obtained as described in FIG. 2. Compound 3 is converted into 5-methylcytidine derivative 6 by following a reported procedure (Reference: Rivakar, K. J.; Reese, C. B.; J. Chem. Soc. Perkin. Trans. 1 1982, 1171). The resulting material is then benzoylated at N-4 position with TMSCl, pyridine and benzoyl chloride to yield the compound 7. Phosphytilation of compound 7 with N,N-diisopropylamine tetrazolide and 2-cyanoethyl-N,N,N',N'-tetraisopropylphosphor-amidite yields the compound 8.

Example 2b

5'-O-DMT-2'-O-(2-methylthioethyl)-N4-benzoyl-5-methylcytidine-3'-O-succinyl CPG (9).

Compound 7 (FIG. 2) is converted into 3'-O-succinyl derivative using succinic anhydride and DMAP in dichloroethane at 60° C. The succinyl derivative is coupled to amino alkyl CPG using 2(1H-benzotriazole)-1-yl)-1,1,3,3-tetramethyluronium tetraflouroborate and N-methylmorpholine in DMF to yield the compound 9.

Example 3a

5'-O-DMT-2'-O-(2-methylthioethyl)-uridine-3'-[(2-cyanoethyl)-N,N-diisopropylphosphoramidite) (13)

Figure 3:
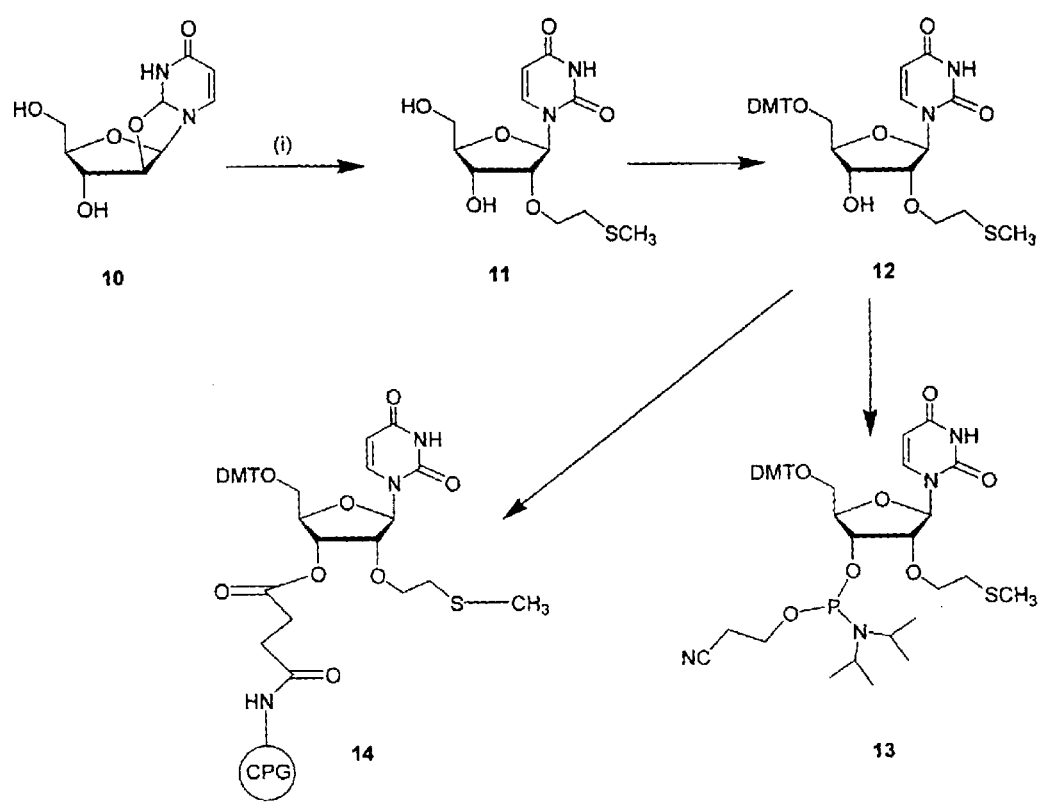
FIG. 3 depicts formation of 5'-O-DMT-2'-O-(2-methylthioethyl)-uridine-3'-[(2-cyanoethyl)-N,N-diisopropylphosphoramidite) 13 and 5'-O-DMT-2'-O-(2-methylthioethyl)-uridine-3'-O-succinyl CPG 14.

Compound 13 is synthesized according to FIG. 3. 2,2'-anhydrouridine 10 is heated at 160° C. with the borate ester of S-methyl-2-thioethanol in S-methyl-2-thioethanol to yield compound 11 which is selectively tritylated at the 5'-position with DMTCl and DMAP in pyridine to yield compound 12. Phosphitylation of compound 12 at 3'position with N,N-diisopropylamine tetrazolide and 2-cyanoethyl-N,N,N',N'-tetraisopropylphosphoramidite will yield the compound 13.

Example 3b

5'-O-DMT-2'-O-(2-methylthioethyl)uridine-3'-O-succinyl CPG (14)

Compound 12 (FIG. 3) is treated with succinic anhydride and DMAP in dichloroethane at 60° C. The resulting 3'-O-succinyl derivative attached to CPG using 2-(1H-benzotriazole)-1,1,3,3-tetramethyluronium tetraflouroborate and N-methylmorpholine in DMF to yield compound 14.

Example 4a

5'-O-DMT-2'-O-(2-methylthioethyl)-N4-benzoyl-cytidine-3'-[(2-cyanoethyl)-diisopropylphosphoramidite] (17)

Figure 4:
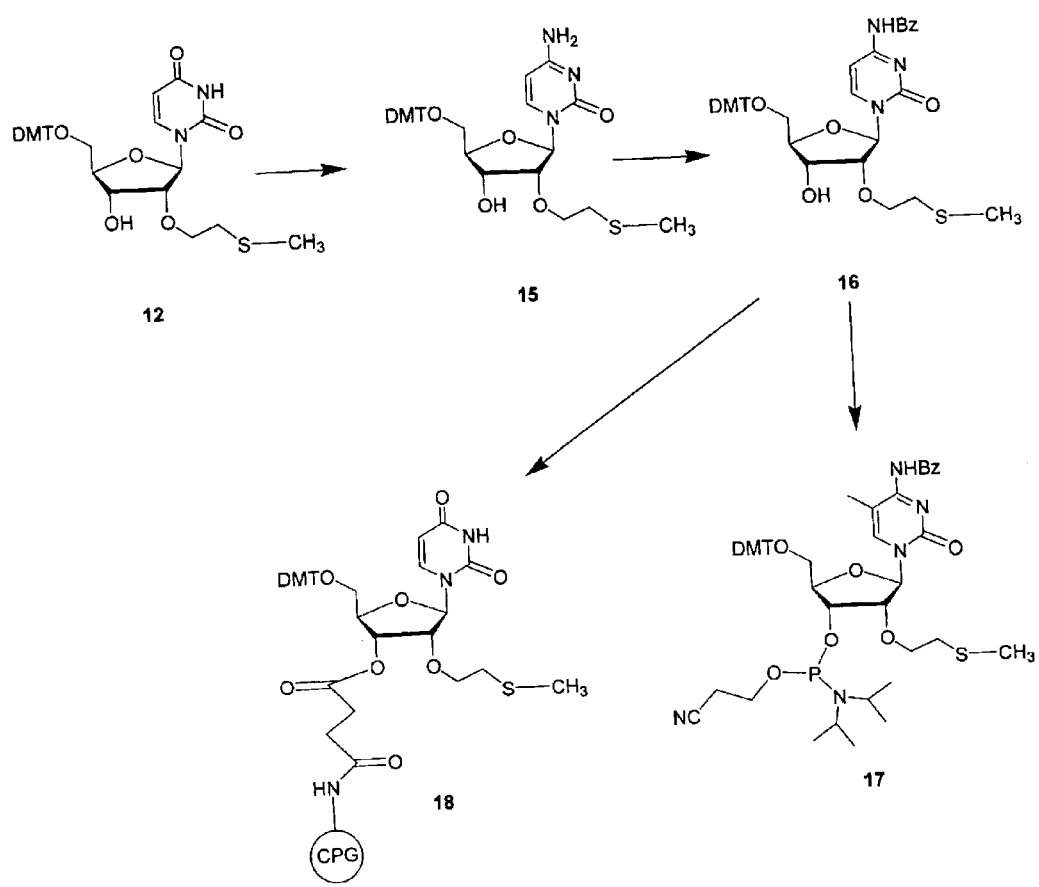
FIG. 4 depicts formation of 5'-O-DMT-2'-O-(2-methylthioethyl)-N4-benzoyl-cytidine-3'-[(2-cyanoethyl)-diisopropylphosphoramidite] 17 and 5'-O-DMT-2'-O-(2-methylthioethyl)-N4-benzoyl-cytidine-3'-O-succinyl CPG 18.

Compound 16 is synthesized a described in FIG. 4. Compound 12 is converted into the cytidine derivative 15 by following standard protocols. The resulting compound is benzoylated with TMSCl, pyridine and benzoyl chloride to yield compound 16. Treatment with N,N-diisopropylamine tetrazolide and 2-cyanoethyl-N,N,N',N'-tetraisopropylphosphoramidite will yield compound 17.

Example 4b

5'-O-DMT-2'-O-(2-methylthioethyl)-N4-benzoyl-cytidine-3'-O-succinyl CPG (18)

Compound 16 (FIG. 4) is treated with succinic anhydride and DMAP in dichloroethane at 60° C. The resulting succinyl derivative is coupled to CPG using 2-(1H-benzotriazole)-1,1,3,3-tetramethyluronium tetraflouroborate and N-methylmorpholine in DMF to yield compound 18.

Example 5a

5'-O-DMT-2'-O-(2-methylthioethyl)-$N^6$-benzoyl-adenosine-3'-[(2-cyanoethyl)-N,N-diisopropylphosphoramidite] (24)

Adenosine 19 is alkylated with S-methyl-2-thioethanol chloride using NaH in DMF to yield a mixture of 2' and 3'-isomers (20 and 21 respectively). The isomers are separated by silica gel flash column chromatography. The 2'-isomer is benzoylated by treatment with TMSCl, Pyridine and benzoyl chloride to yield the compound 22. Compound 22 is tritylated by treatment with DMTCI, DMAP and pyridine. The tritylated compound 23 is treated N,N-diisopropylamine tetrazolide and 2-cyanoethyl-N,N,N',N'-tetraisopropylphosphoramidite in acetonitrile to yield compound 24.

Example 5b

5'-O-DMT-2'-O-(2-methylthioethyl)-$N^6$-benzoyl-adenosine-3'-O-succinyl CPG (25)

Compound 23 is converted into 3'-O-succinyl derivative using succinic anhydride and DMAP in dichloroethane at 60° C. The succinyl derivative is coupled to amino alkyl CPG using 2-(1H-benzotriazole)-1-yl)-1,1,3,3-tetramethyluronium tetraflouroborate and N-methylmorpholine in DMF to yield 25.

Example 6a

5'-O-DMT-2'-O-(2-methylthioethyl)-$N^2$-isobutryl-guanosine-3'-[(2-cyanoethyl) -N,N-diisopropylphosphoramidite] (31)

Diaminopurine riboside 26 is alkylated with S-methyl-2-thioethylchloride in DMF and NaH to yield a mixture of 2' and 3'-isomers (27 and 28 respectively). The mixture of 2' and 3'-isomers is treated with adenosine deaminase in phosphate buffer (pH 7.4) to yield 2'-O-(2-methylthioethyl) guanosine 29. Compound 29 is converted into isobutyryl derivative at N-2 position using TMSCl, pyridine and isobutyryl chloride followed by selective tritylation at the 5'-position to yield compound 30. Phosphitylation of compound 30 with N,N-diisopropylamine tetrazolide and 2-cyanoethyl-N,N,N',N'-tetraisopropylphosphoramidite in acetonitrile yields compound 31.

Example 6b
5'-O-DMT-2'-O-(2-methylthioethyl)-$N^2$-isobutyryl-guanosine-3'-O-succinyl CPG (32)

Figure 5:
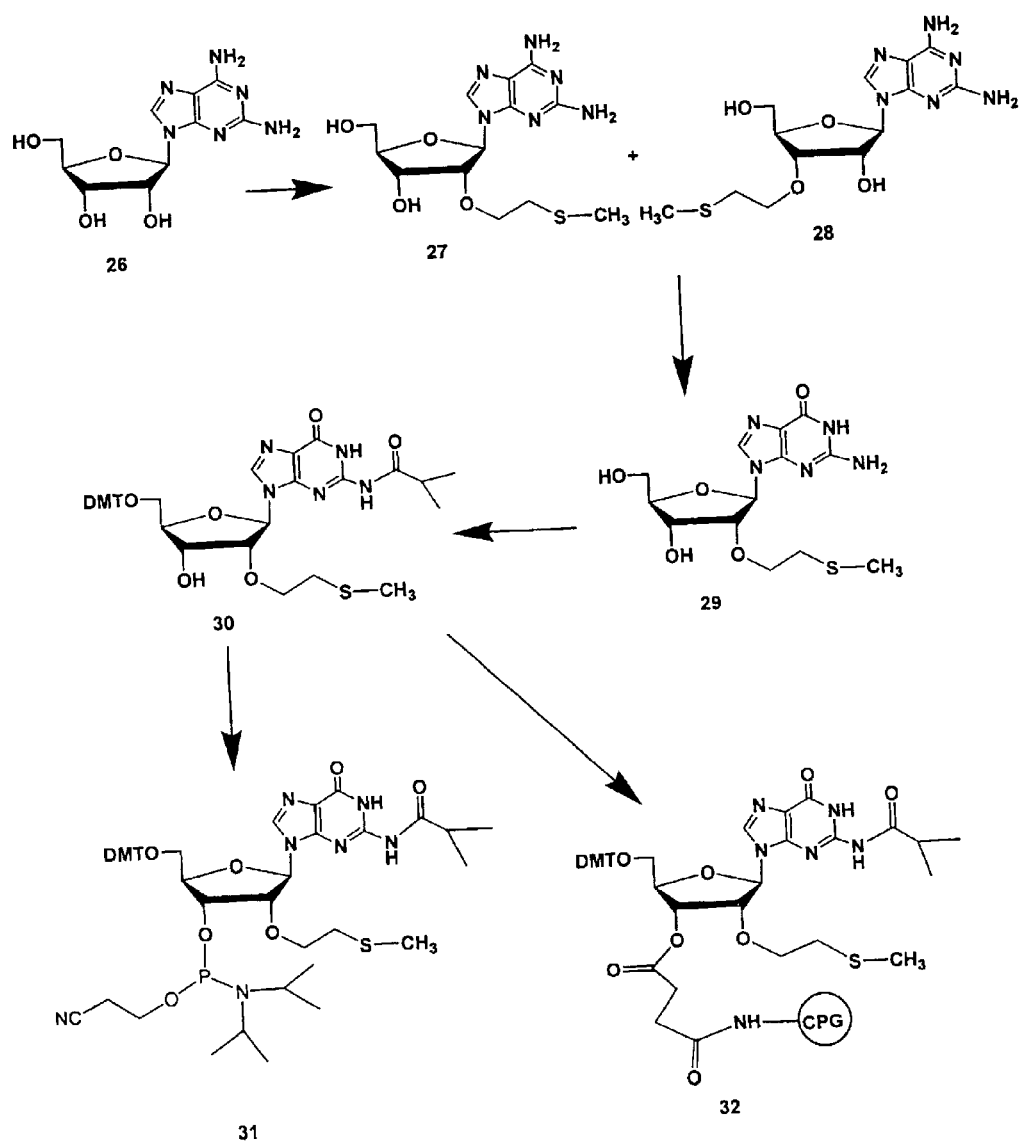
FIG. 5 depicts formation of 5'-O-DMT-2'-O-(2-methylthioethyl)-$N^2$ isobutryl-guanosine-3'-[(2-cyanoethyl)-N,N-diisopropylphosphoramidite] 31 and 5'-O-DMT-2'-O-(2-methylthioethyl)-$N^2$-isobutyryl-guanosine-3'-O-succinyl CPG 32.

Compound 30 (FIG. 5) is treated with succinic anhydride and DMAP in dichloroethane at 60° C. The succinyl derivative is coupled to CPG using 2-(1H-benzotriazole)1-yl)-1,1,3,3-tetramethyluronium tetraflouroborate and N-methylmorpholine in DMF to yield the compound 32.

Example 7a
5'-O-DMT-2'-O-(2-methylthioethyl)-2-fluoro-adenosine-3'-[(2-cyanoethyl)-N,N-diisopropylphosphoramidite] (35)

Compound 27 is treated with $NaNO_2$, 48% $HBF_4$ at –10° C. to yield compound 33 using a published procedure (Montgomery, J. A.; Hewson, K. J. Am. Chem. Soc. 1960, 82, 463). Compound 33 is tritylated using DMTCl and DMAP in pyridine. The tritylated compound 34 is phosphitylated using N,N-diisopropylamine tetrazolide and 2-cyanoethyl-N,N,N',N'-tetraisopropylphosphoramidite in acetonitrile to yield the compound 35.

Example 7b
5'-O-DMT-2'-O-(2-methylthioethyl)-2-fluoro-adenosine-3'-O-succinyl CPG (36)

Figure 6:
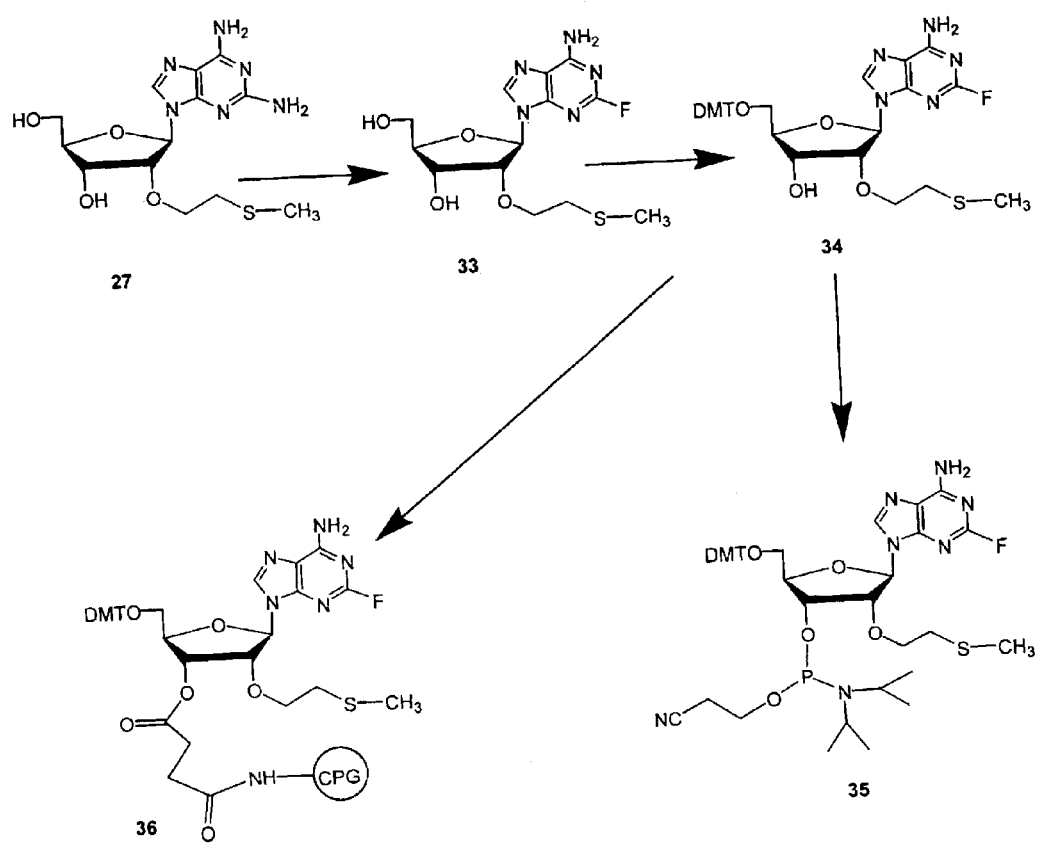
FIG. 6 depicts formation of 5'-O-DMT-2'-O-(2-methylthioethyl)-2-fluoro-adenosine-3'-[(2-cyanoethyl)-N,N-diisopropylphosphoramidite] 35 and 5'-O-DMT-2'-O-(2-methylthioethyl)-2-fluoro-adenosine-3'-O-succinyl CPG 36.

Compound 34 (FIG. 6) is succinylated using succinic anhydride and DMAP in dichloroethane at 60° C. The succinyl derivative is coupled to CPG using 2-(1H-benzotriazole)-1-yl)-1,1,3,3-tetramethyluronium tetraflouroborate and N-methylmorpholine in DMF to yield the compound 36.

Example 8a
5'-O-DMT-2'-O-(2-methylthioethyl)-5-methyluridine-3'-[(2-cyanoethyl)-N,N-diisopropylphosphoramidite] (39)

Compound 39 is synthesized as illustrated in FIG. 1. Compound 1 is heated at 160° C. with borate ester of S-methyl-2-thioethanol in S-methyl-2-thioethanol (Source: Aldrich, Milwaukee) to yield compound 37 which is tritylated using DMTCl and DMAP in pyridine to yield compound 38. Phosphitylation of compound 38 with N,N-diisopropylamine tetrazolide and 2-cyanoethyl-N,N,N',N'-tetraisopropylphosphoramidite yields compound 39.

Example 8b
5'-O-DMT-2'-O-(2-phenylthioethyl)-5-methyluridine-3'-O-succinyl CPG (40)

Figure 7:
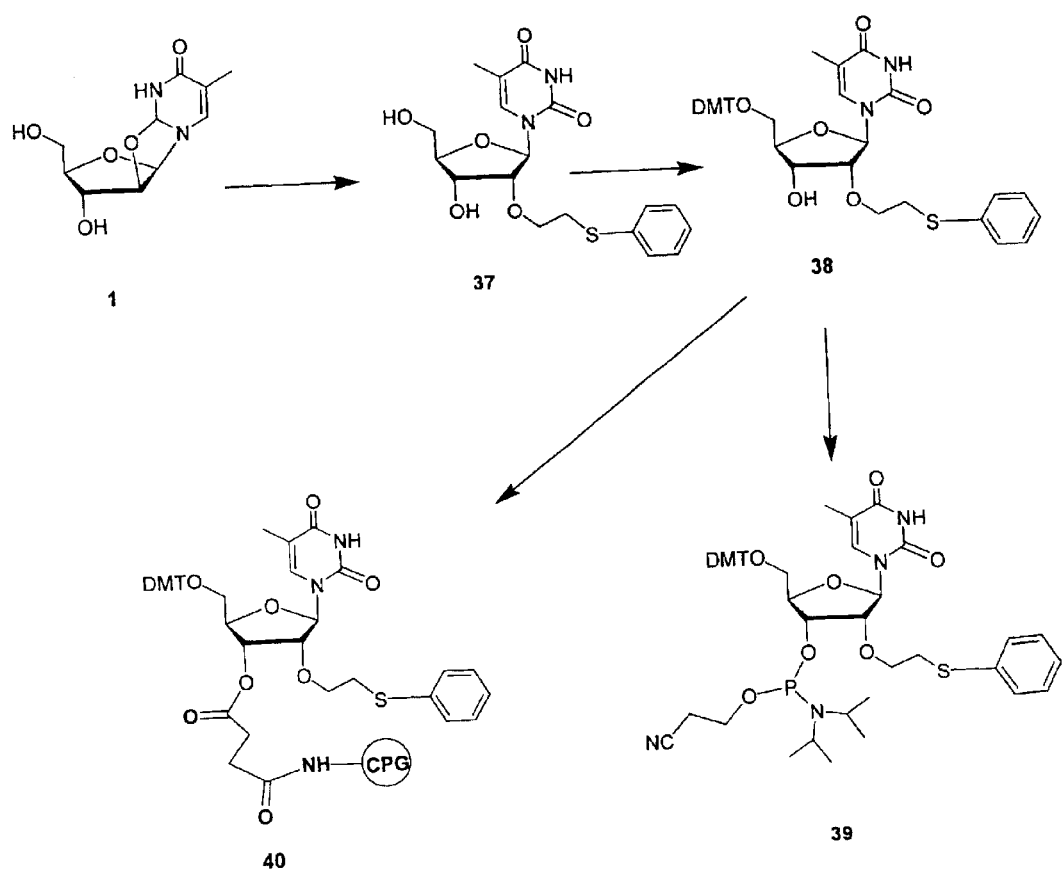
FIG. 7 depicts formation of 5'-O-DMT-2'-O-(2-methylthioethyl)-5-methyluridine-3'-[(2-cyanoethyl)-N,N-diisopropylphosphoramidite] 39 and 5'-O-DMT-2'-O-(2-phenylthioethyl)-5-methyluridine-3'-O-succinyl CPG 40.

Compound 38 (FIG. 7) is sucinylated using succinic anhydride and DMAP in dichloroethane at 60° C. The succinylated derivative is attached to CPG using 2-(1H-benzotriazole)-1-yl)-1,1,3,3-tetramethyluronium tetraflouroborate and N-methylmorpholine in DMF to yield the compound 40.

Example 9a
5'-O-DMT-2'-O-(2-phenylthioethyl)-N4-benzoyl-5-methylcytidine-3'-[(2-cyanoethyl)-diisopropylphosphoramidite] (43)

Figure 8:
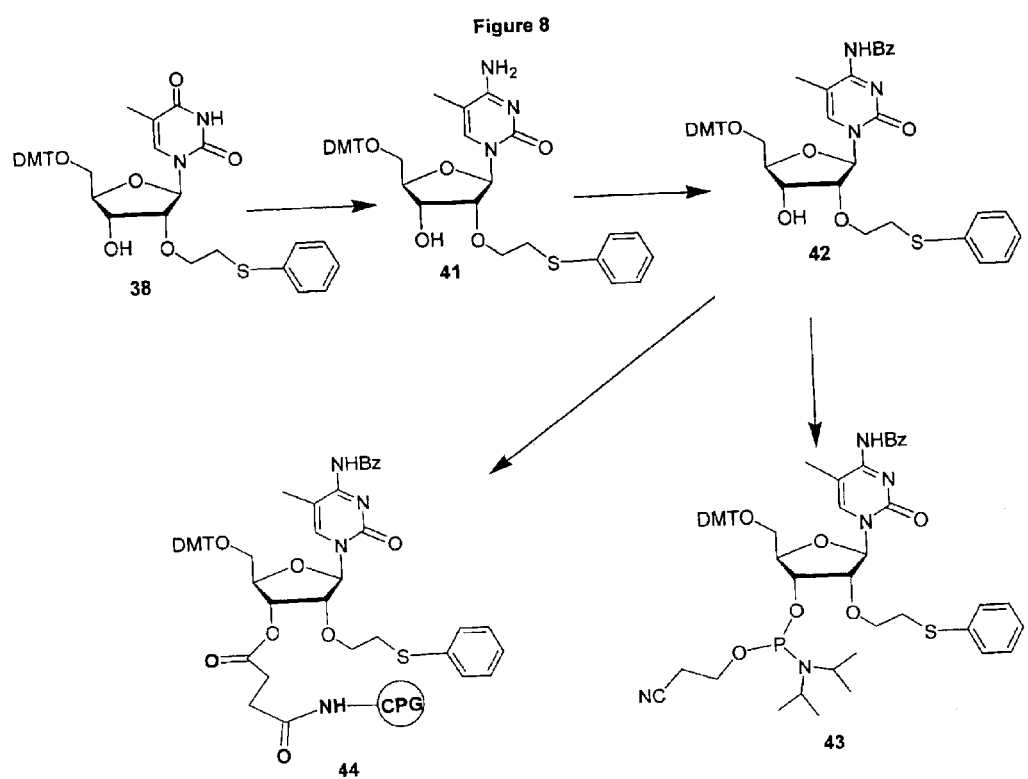
FIG. 8 depicts formation of 5'-O-DMT-2'-O-(2-phenylthioethyl)-N4-benzoyl-5-methylcytidine-3'-[(2-cyanoethyl)-diisopropylphosphoramidite] 43 and 5'-O-DMT-2'-O-(2-phenylthioethyl)-N4-benzoyl-5-methylcytidine-3'-O-succinyl CPG 44.

Compound 38 is obtained as described illustrated in FIG. 8. Compound 38 is converted into the 5-methylcytidine derivative 41 by following a reported procedure (Reference: Divakar, K. J.; Reese, C. B.; J. Chem. Soc. Perkin. Trans. 1 1982, 1171). The 5-methylcytidine derivative is them benzoylated with TMSCl, pyridine and benzoyl chloride to yield compound 42. Phosphitylation with N,N-diisopropylamine tetrazolide and 2-cyanoethyl-N,N,N',N'-tetraisopropylphosphor -amidite yields compound 43.

Example 9b
5'-O-DMT-2'-O-(2-phenylthioethyl)-N4-benzoyl-5-methylcytidine-3'-O-succinyl CPG (44)

Compound 42 (FIG. 8) is converted into the 3'-O-succinyl derivative using succinic anhydride and DMAP in dichloroethane at 60° C. The succinyl derivative is coupled to CPG in the presence of 2-(1H-benzotriazole)-1-yl)-1,1,3,3-tetramethyluronium tetraflouroborate and N-methylmorpholine in DMF to yield compound 44.

Example 10a
5'-O-DMT-2'-O-(2-phenylthioethyl)-$N^6$-benzoyl-adenosine-3'-[(2-cyanoethyl) -N,N-diisopropylphosphoramidite] (49)

Figure 9:
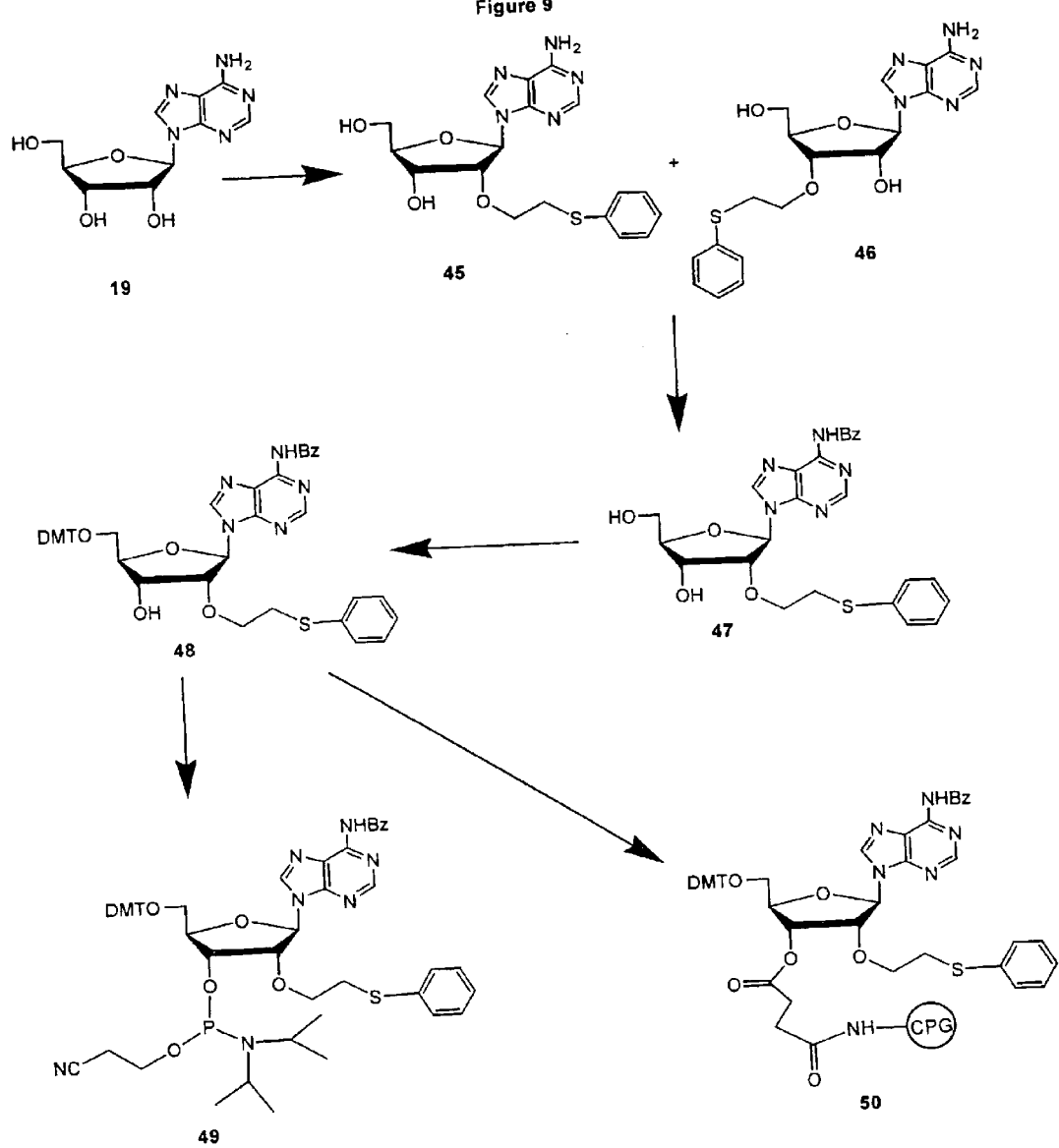
FIG. 9 depicts formation of 5'-O-DMT-2'-O-(2-phenylthioethyl)-$N^6$-benzoyl-adenosine-3'-[(2-cyanoethyl)-N,N-diisopropylphosphoramidite] 49 and 5'-O-DMT-2'-O-(2-phenylthioethyl)-$N^6$-benzoyl-adenosine-3'-O-succinyl CPG 50.

Compound 49 is synthesized as illustrated FIG. 9. Adenosine is alkylated with S-methyl-2-thioethanol chloride in DMF and NaH to yield a mixture of the 2' and 3'-isomers (45 and 46 respectively). The two isomers are separated by silica gel flash column chromatography. The 2'-isomer is then benzoylated with TMSCl, pyridine and benzoyl chloride to yield compound 47. Compound 47 is tritylated with DMTCl, DMAP and pyridine to give compound 48 which is then phosphitylated N,N-diisopropylamine tetrazolide and 2-cyanoethyl-N,N,N',N'-tetraisopropylphosphor-amidite in acetonitrile to yield compound 49.

Example 10b
5'-O-DMT-2'-O-(2-phenylthioethyl)-$N^6$-benzoyl-adenosine-3'-O-succinyl CPG (50)

Compound 48 (FIG. 9) is converted into the 3'-O-succinyl derivative using succinic anhydride and DMAP in dichloroethane at 60° C. The succinyl derivative is coupled to CPG in the presence of 2-(1H-benzotriazole)-1-yl)-1,1,3,3-tetramethyluronium tetraflouroborate and N-methylmorpholine in DMF to yield the compound 50.

Example 11a
5'-O-DMT-2'-O-(2-phenylthioethyl)-$N^2$-isobutryl-guanosine-3'-[(2-cyanoethyl)-N,N-diisopropylphosphoramidite] (55)

Diaminopurine riboside 26 is alkyalted with S-phenyl-2-thioethylchloride in DMF and NaH to yield a mixture of the 2' and 3'-isomers (51 and 52 respectively). The mixture of 2' and 3'-isomers is treated with adenosine deaminase in phosphate buffer (pH 7.4) to yield 2'-O-(2-phenylthioethyl) guanosine 53. Compound 53 is converted into the isobutyryl derivative using TMSCl, pyridine and isobutyryl chloride followed by tritylation to give compound 54. Phosphitylation of compound 54 with N,N-diisopropylamine tetrazolide and 2-cyanoethyl-N,N,N',N'-tetraisopropylphosphoramidite in acetonitrile yields compound 55.

Example 11b
5'-O-DMT-2'-O-(2-phenylthioethyl)-$N^2$-isobutryl-guanosine-3'-O-succinyl CPG (56)

Figure 10:
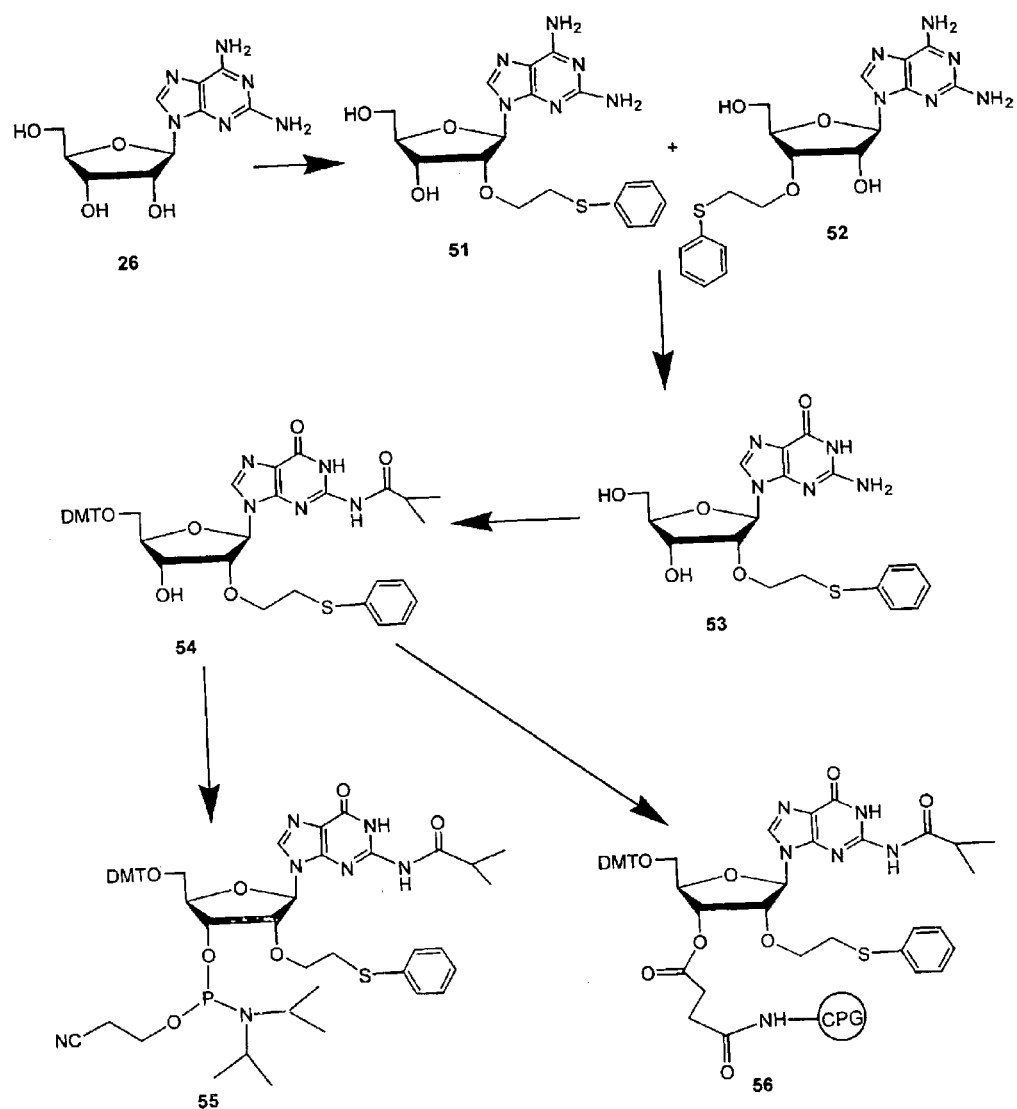
FIG. 10 depicts formation of 5'-O-DMT-2'-O-(2-phenylthioethyl)-$N^2$-isobutryl-guanosine-3'-[(2-cyanoethyl)-N,N-diisopropylphosphoramidite] 55 and 5'-O-DMT-2'-O-(2-phenylthioethyl)-$N^2$-isobutryl-guanosine-3'-O-succinyl CPG 56.

Compound 54 (FIG. 10) is succinylated using succinic anhydride and DMAP in dichloroethane at 60° C. The succinyl derivative is coupled to CPG using 2-(1H-benzotriazole)-1-yl)-1,1,3,3-tetramethyluronium tetraflouroborate and N-methylmorpholine in DMF to yield compound 56.

Example 12a
5'-O-DMT-2'-O-(2-phenylthioethyl)-2-fluoro-adenosine-3'-[(2-cyanoethyl)-N,N-diisopropylphosphoramidite] (59)

Compound 51 is treated with NaNO$_2$, 48% HBF$_4$ at −10° C. to yield compound 57 which is tritylated using DMTCl, DMAP in pyridine to yield compound 58. Compound 58 is further phosphitylated with N,N-diisopropylamine tetrazolide and 2-cyanoethyl-N,N,N',N'-tetraisopropylphosphoramidite in acetonitrile to yield compound 59.

Example 12b
5'-O-DMT-2'-O-(2-phenylthioethyl)-2-fluoro-adenosine-3'-O-succinyl CPG (60)

Figure 11:
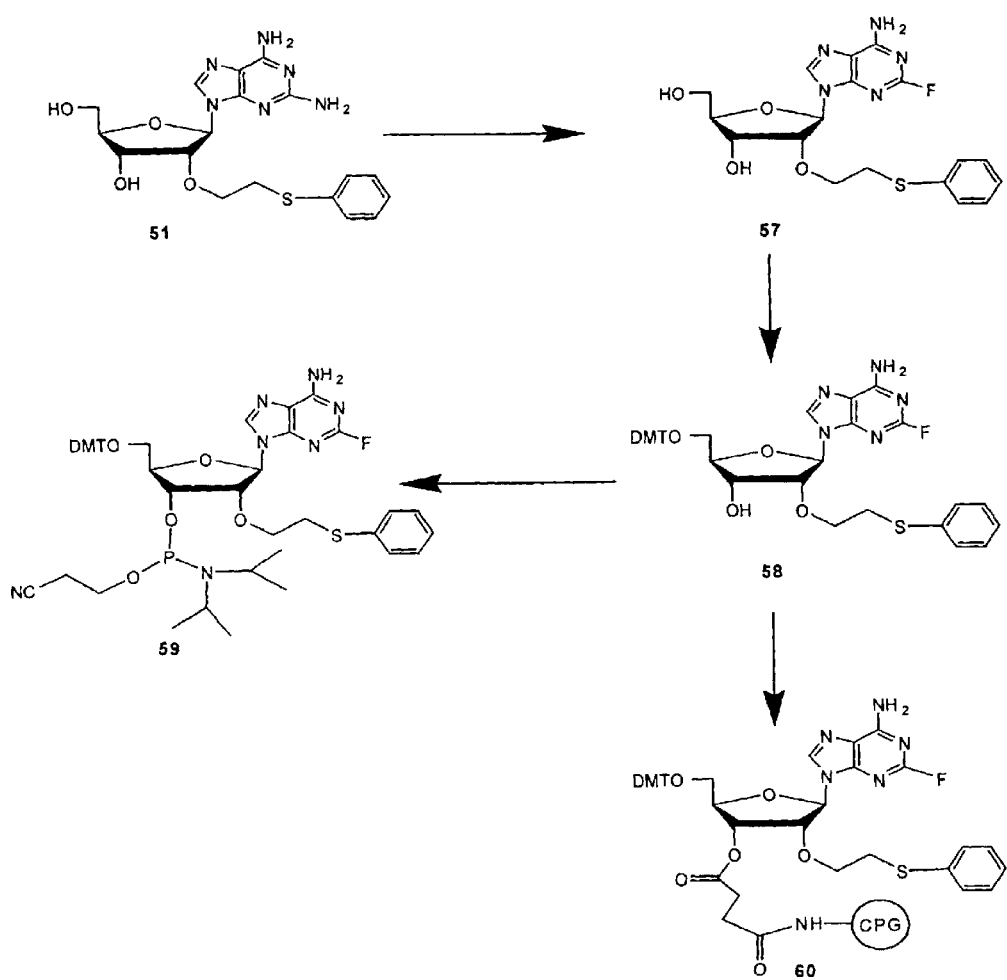
FIG. 11 depicts formation of 5'-O-DMT-2'-O-(2-phenylthioethyl)-2-fluoro-adenosine-3'-[(2-cyanoethyl)-N,N-diisopropylphosphoramidite] 59 and 5'-O-DMT-2'-O-(2-phenylthioethyl)-2-fluoro-adenosine-3'-O-succinyl CPG 60.

Compound 58 (FIG. 11) is converted into 3'-O-succinyl derivative using succinic anhydride and DMAP in dichloroethane at 60° C. The succinyl derivative is coupled to CPG using 2-(1H-benzotriazole)-1-yl)-1,1,3,3-tetramethyluronium tetraflouroborate and N-methylmorpholine in DMF to yield compound 60.

Example 13a
5'-O-DMT-2'-O-(2-methanesulfinyl-ethyl)-5-methyluridine-3'-[(2-cyanoethyl)-diisopropylphosphoramidite] (62)

Compound 3 is treated with CSO [1-S-(+)-10-camphorsulfonyl)oxaziridine] in CH$_3$CN to yield compound 61. Compound 61 is phosphitylated with N,N-diisopropylamine tetrazolide and 2-cyanoethyl-N,N,N',N'-tetraisopropylphosphoramidite in acetonitrile to yield compound 62.

Example 13b
5'-O-DMT-2'-O-(2-methanesulfinylethyl)-5-methyluridine-3'-O-succinyl CPG (63)

Figure 12:
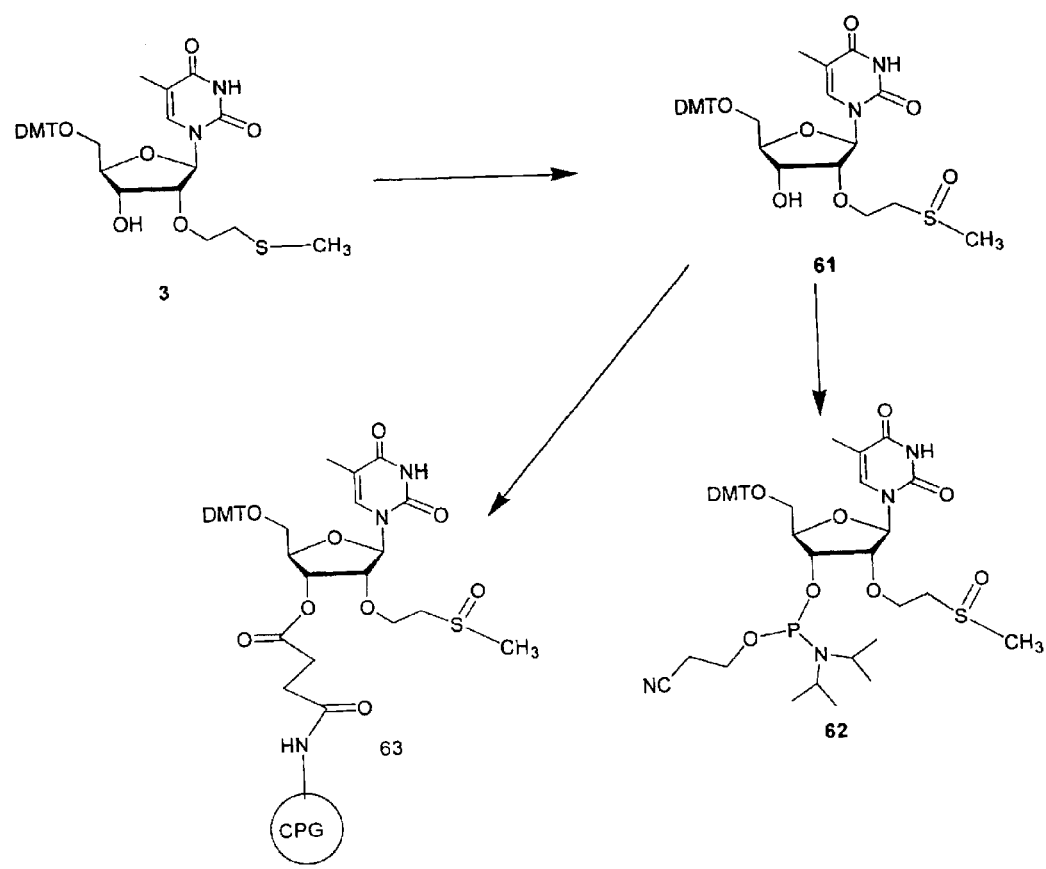
FIG. 12 depicts formation of 5'-O-DMT-2'-O-(2-methanesulfinyl-ethyl)-5-methyluridine-3'-[(2-cyanoethyl)-diisopropylphosphoramidite] 62 and 5'-O-DMT-2'-O-(2-methanesulfinylethyl)-5-methyluridine-3'-O-succinyl CPG 63.

Compound 61 (FIG. 12) is succinylated using succinic anhydride and DMAP in dichloroethane at 60° C. The succinyl derivative is coupled to CPG using 2-(1H-benzotriazole)-1-yl)-1, 1,3,3-tetramethyluronium tetraflouroborate and N-methylmorpholine in DMF to yield compound 63.

Example 14a
5'-O-DMT-2'-O-(2-methanesulfonyl-ethyl)-5-methyluridine-3'-[(2-cyanoethyl)-diisopropylphosphoramidite] (65)

Compound 3 is treated with H$_2$O$_2$ in acetone as described in a published procedure (Baker, A. D.; Scharfman, R.; Stein, C. A. *Tetrahedron Lett.* 1984, 24, 2957.) to yield the compound 64. Compound 64 is phosphitylated with N,N-diisopropylamine tetrazolide and 2-cyanoethyl-N,N,N',N'-tetraisopropylphosphoramidite in acetonitrile to yield compound 65.

Example 14b
5'-O-DMT-2'-O-(2-methanesulfonylethyl)-5-methyluridine-3'-O-succinyl CPG (66)

Figure 13:
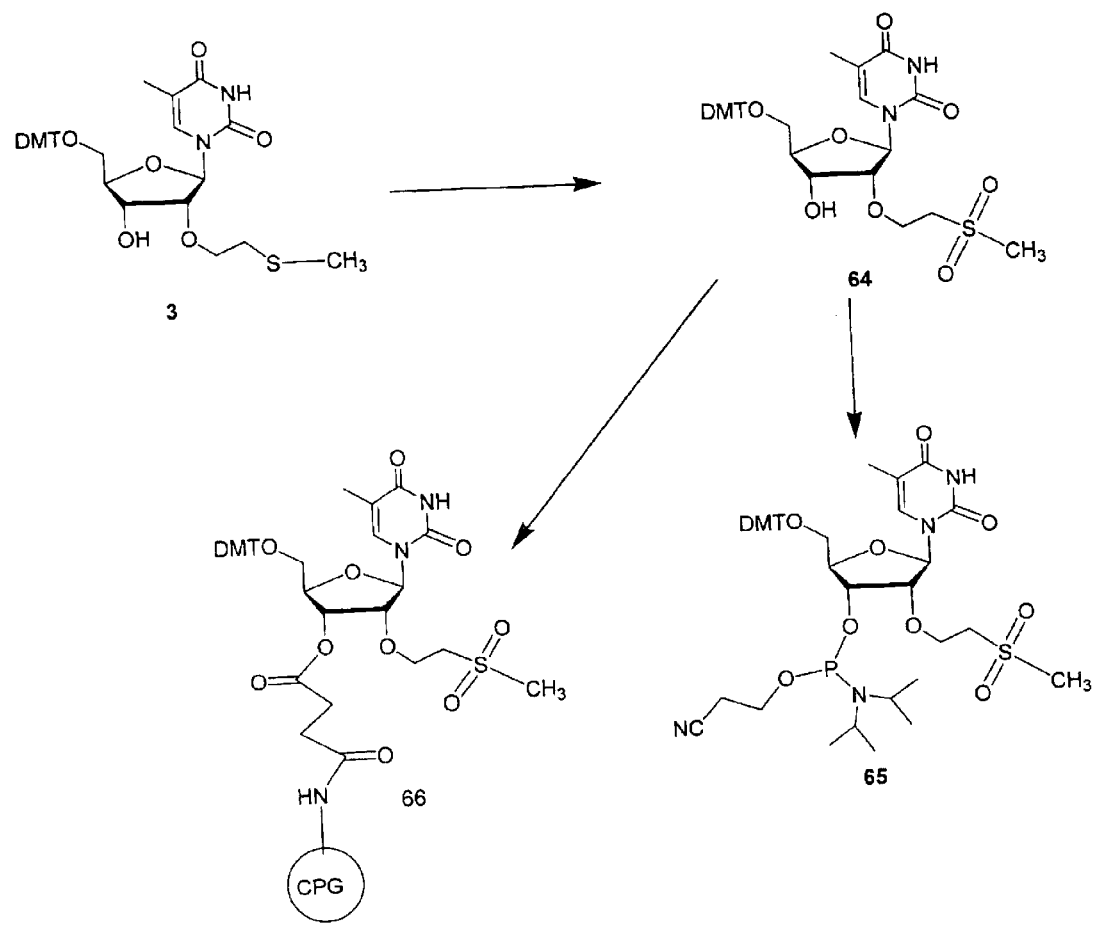
FIG. 13 depicts formation of 5'-O-DMT-2'-O-(2-methanesulfonyl-ethyl)-5-methyluridine-3'-[(2-cyanoethyl)-diisopropylphosphoramidite] 65 and 5'-O-DMT-2'-O-(2-methanesulfonylethyl)-5-methyluridine-3'-O-succinyl CPG 66.

Compound 64 (FIG. 13) is succinylated using succinic anhydride and DMAP in dichloroethane at 60° C. The succinyl derivative is coupled to CPG using 2-(1H-benzotriazole)-1-yl)-1,1,3,3-tetramethyluronium tetraflouroborate and N-methylmorpholine in DMF to yield compound 66.

Example 15a
5'-O-DMT-2'-O-[2-(methoxy)ethyl]-5-[[2-(methylthio)ethyl]amino]uridine-3'-[(2-cyanoethyl)-N,N-diisopropylphosphoramidite] (70)

Figure 15:
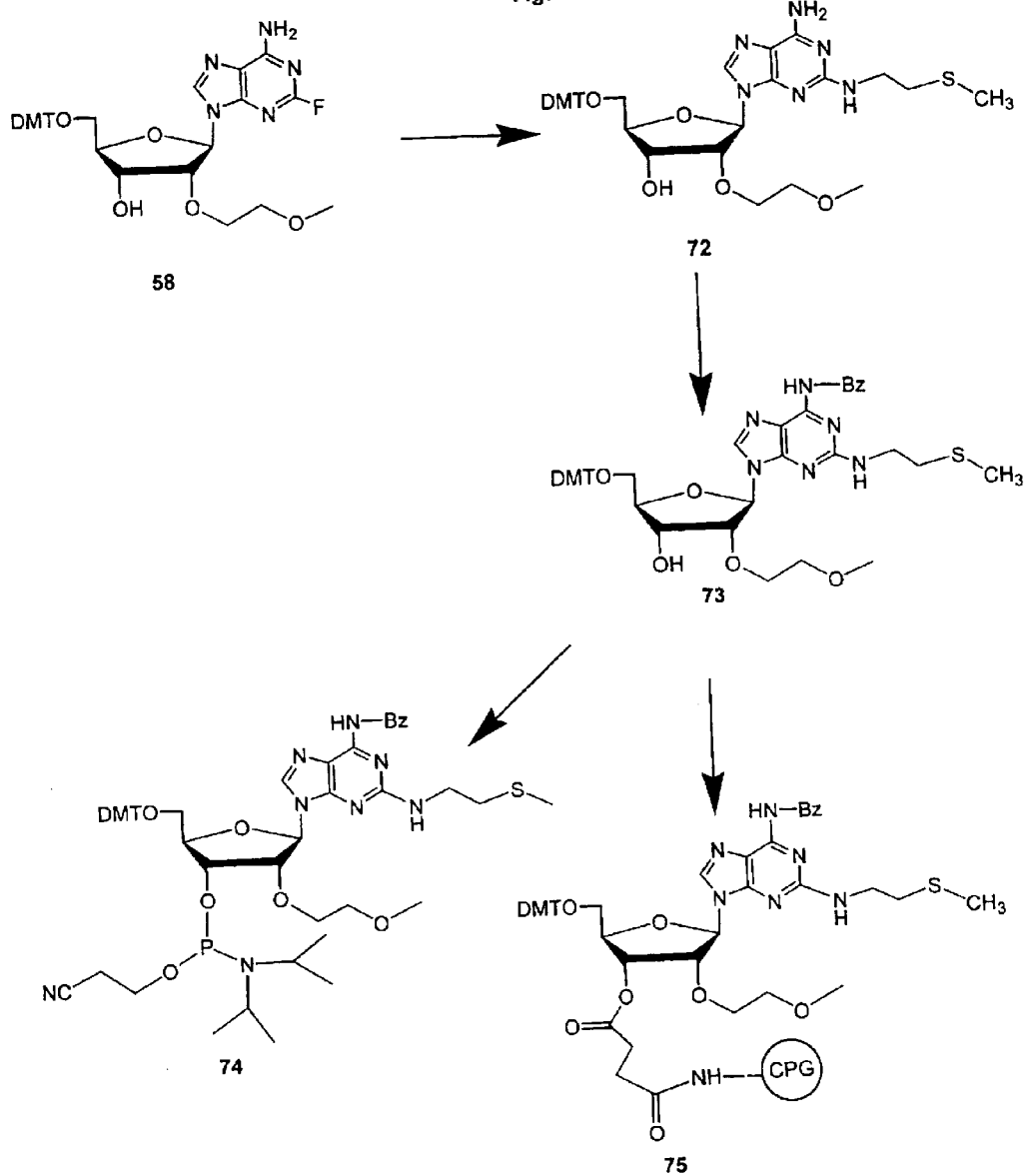
FIG. 15 depicts formation of N4-Benzoyl-5'-O-DMT-2'-O-[2-(methoxy)ethyl]-$N^2$-[2-(methylthio)ethyl]-2-aminoadenosine-3'-[(2-cyanoethyl)-N,N-diisopropylphosphoramidite] 74 and N4-Benzoyl-5'-O-DMT-2'-O-[2-(methoxy)ethyl]-$N^2$-[2-(methylthio)ethyl]-2-aminoadenosine uridine-3'-O-succinyl CPG 75.

Compound 67 is prepared starting from 2'-O-[2-(methoxy)ethyl]uridine according to the literature procedure (Reference: Ross, B. S. et. al. Nucleosides Nucleotides, 1997, 16, 1641–1643). It is then alkylated with 2-thiomethyl ethylamine (prepared according to patent JP 59164763) to give 68 (FIG. 15). Compound 68 is tritylated to give compound 69 which is phosphitylated to give compound 70.

Example 15b
5'-O-DMT-2'-O-[2-(methoxy)ethyl]-5-[[2-(methylthio)ethyl]amino]uridine-3'-O-succinyl CPG (71)

Figure 14:
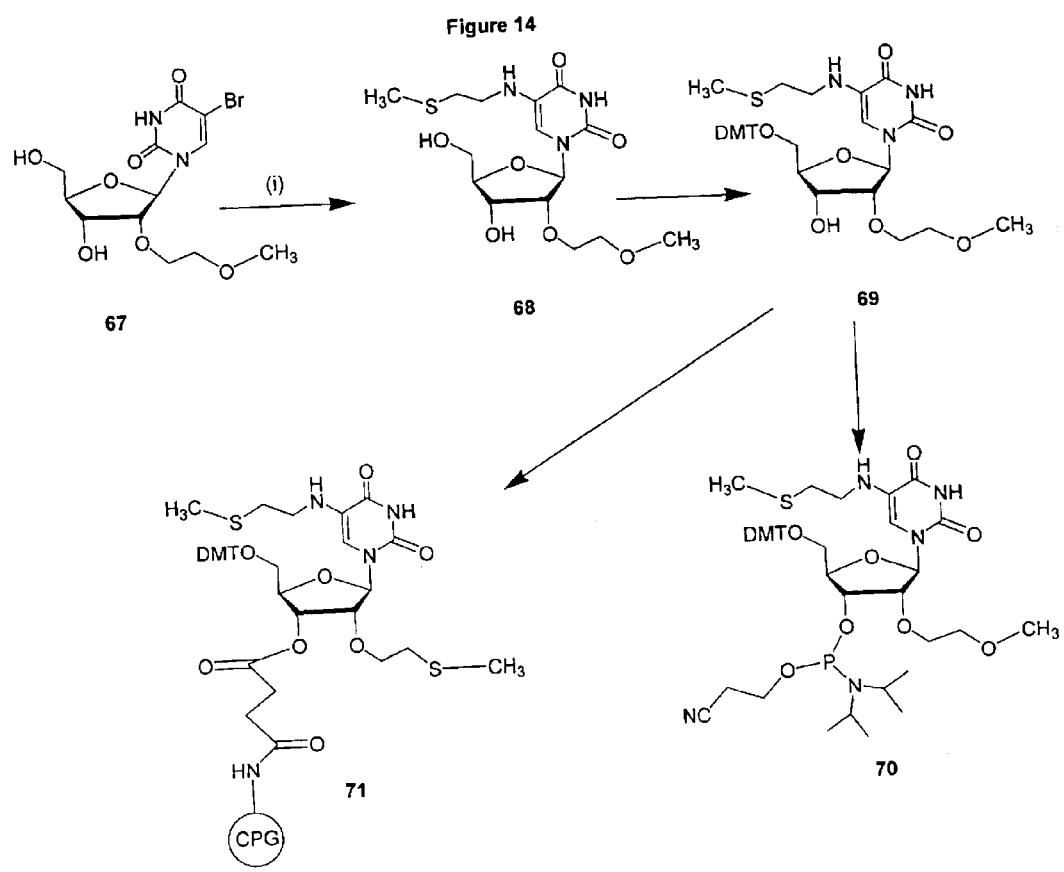
FIG. 14 depicts alkylation of 2'-O-[2-(methoxy)ethyl] uridine with 2-thiomethyl ethylamine followed by tritylation and phosphitylation to give 5'-O-DMT-2'-O-[2-(methoxy)ethyl]-5-[[2-(methylthio)ethyl]amino]uridine-3'-[(2-cyanoethyl)-N,N-diisopropylphosphoramidite] 70 and succinylation of compound 69 to yield 5'-O-DMT-2'-O-[2-(methoxy)ethyl]-5-[[2-(methylthio)ethyl]amino]uridine-3'-O-succinyl CPG 71.

Compound 69 (FIG. 14) is succinylated using succinic anhydride and DMAP in dichloroethane at 60° C. The succinyl derivative is coupled to CPG using 2-(1H-benzotriazole)-1-yl)-1,1,3,3-tetramethyluronium tetrafluoroborate and N-methylmorpholine in DMF to yield compound 71.

Example 16a
N4-Benzoyl-5'-O-DMT-2'-O-[2-(methoxy)ethyl]-N$^2$-[2-aminoadenosine-3'-[(2-cyanoethyl)-N,N-diisopropylphosphoramidite] (74)

Compound 58 is treated with 2-thiomethyl ethylamine (prepared according to patent JP 59164763) to give compound 72. Compound 72 is N4-benzoylated under transient protection conditions to give compound 73. Compound 73 is phosphitylated to give compound 74.

Example 16b
N4-Benzoyl-5'-O-DMT-2'-O-[2-(methoxy)ethyl]-N$^2$-[2(methylthio)ethyl]-2-aminoadenosine uridine-3'-O-succinyl CPG (75)

Compound 73 (FIG. 15) is succinylated using succinic anhydride and DMAP in dichloroethane at 60° C. The succinyl derivative is coupled to CPG using 2-(1H-benzotriazole)-1-yl)-1,1,3,3-tetramethyluronium tetrafluoroborate and N-methylmorpholine in DME to yield compound 75.

Example 17a
5'-O-DMT-2'-O-[2-(methoxy)ethyl]-5-[2-(phenylthio)ethyl]amino]uridine-3'-[(2cyanoethyl)-N,N-diisopropylphosphoramidite] (78)

Figure 16:
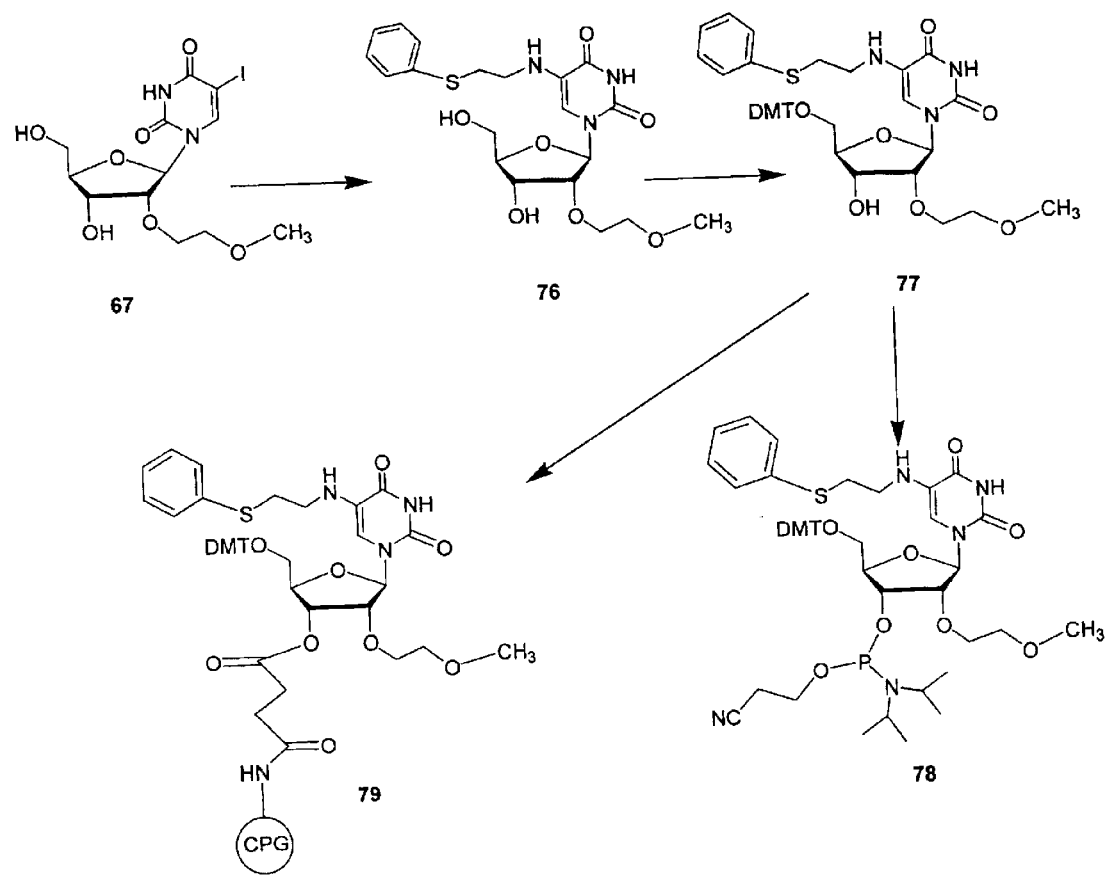
FIG. 16 depicts formation of 5'-O-DMT-2'-O-[2-(methoxy)ethyl]-5-[[2-(phenylthio)ethyl]amino]uridine-3'-[(2-cyanoethyl)-N,N-diisopropylphosphoramidite] 78 and 5'-O-DMT-2'-O-[2-(methoxy)ethyl]-5-[[2-(phenylthio) ethyl]amino]uridine-3'-O-succinyl CPG 79.

Compound 67 is treated with 2-thiophenyl ethylamine (prepared according to patent JP 59164763) to give compound 76 (FIG. 16). Compound 76 is tritylated at to give compound 77 followed by phosphitylation to give compound 78.

Example 17b
5'-O-DMT-2'-O-[2-(methoxy)ethyl]-5-[[2-(phenylthio)ethyl]amino]uridine-3'-O-succinyl CPG (79)

Compound 77 (FIG. 16) is succinylated using succinic anhydride and DMAP in dichloroethane at 60° C. The succinyl derivative is coupled to CPG using 2-(1H-benzotriazole)-1-yl)-1,1,3,3-tetramethyluronium tetrafluoroborate and N-methylmorpholine in DMF to yield compound 79.

Example 18a
N4-Benzoyl-5'-O-DMT-2'-O-[2-(methoxy)ethyl]-N$^2$-[2-(phenylthio)ethyl]-2-aminoadenosine-3'-[(2-cyanoethyl)-N,N-diisopropylphosphoramidite] (82)

Figure 17:
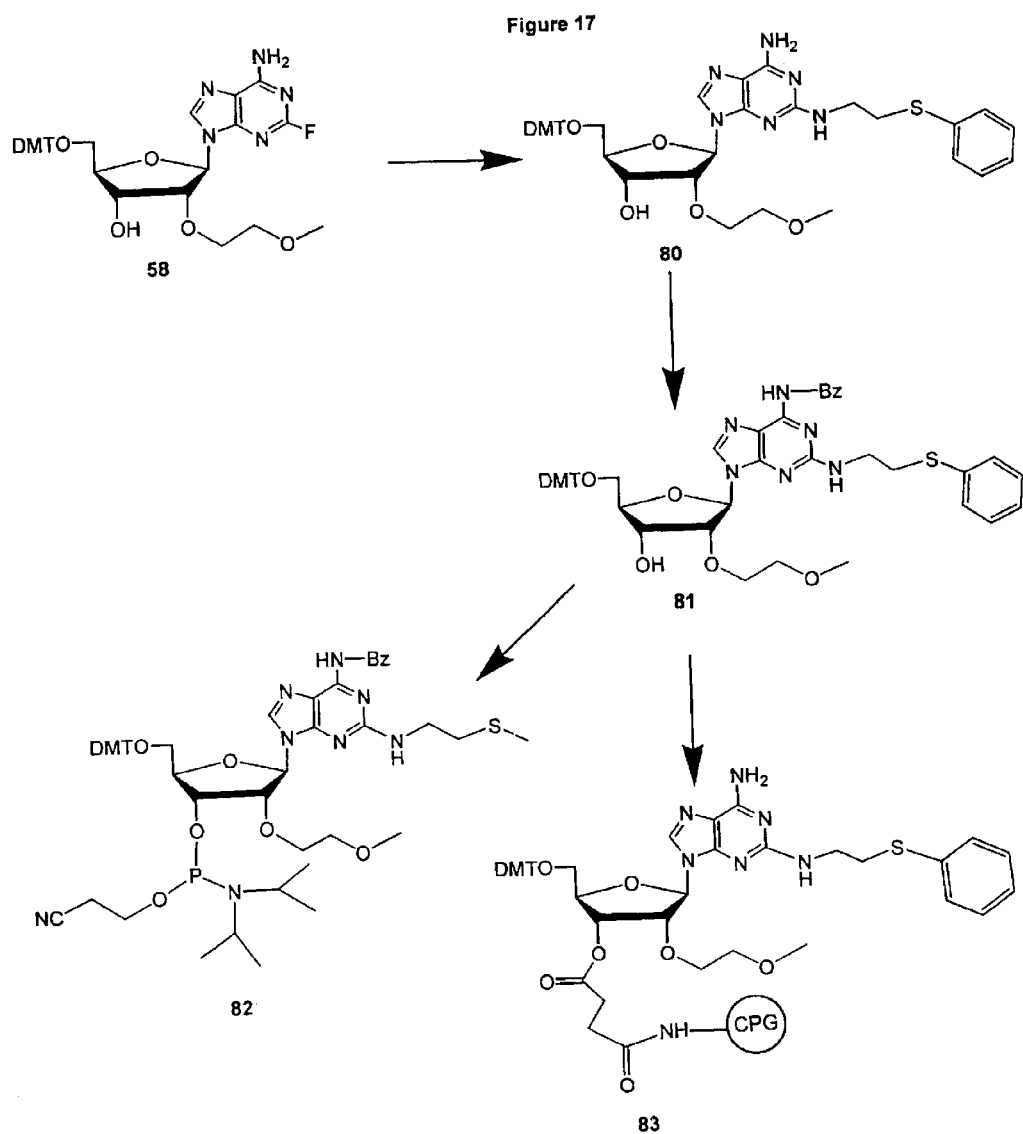
FIG. 17 depicts formation of N4-Benzoyl-5'-O-DMT-2'-O-[2-(methoxy)ethyl]-$N^2$-[2-(phenylthio)ethyl]-2- aminoadenosine-3'-[(2-cyanoethyl)-N,N-diisopropylphosphoramidite] 82 and N4-Benzoyl-5'-O-DMT-2'-O-[2-(methoxy)ethyl]-N²-[2-(phenylthio)ethyl]-2-aminoadenosine-3'-O-succinyl CPG 83.

Compound 58 is treated with 2-thiophenyl ethylamine (prepared according to patent JP 59164763) to give compound 80 (FIG. 17). Compound 80 is benzoylated under transient protection conditions to give compound 81. Compound 81 is phosphitylated to give compound 82.

Example 18b
N4-Benzoyl-5'-O-DMT-2'-O-[2-(methoxy)ethyl]-N$^2$-[2-(phenylthio)ethyl]-2-aminoadenosine-3'-O-succinyl CPG (83)

Compound 81 (FIG. 17) is succinylated using succinic anhydride and DMAP in dichloroethane at 60° C. The succinyl derivative is coupled to CPG using 2-(1H-benzotriazole) 1-yl)-1,1,3,3-tetramethyluronium tetrafluoroborate and N-methylmorpholine in DMF to yield the compound 83.

Example 19a

5'-O-DMT-2'-O-[2-(methoxy)ethyl]-5-[[2-(phenylthio)ethyl]oxo]uridine-3'-[(2-cyanoethyl)-N,N-diisopropylphosphoramidite] (87)

Compound 84 is prepared from 5-hydroxy-2'-deoxy uridine according to a published literature procedure (LaFrancois, C. J. et. al. Chem. Res. Toxicol, 1998, 11 (1), 75–83, Bruce, R. et. al. Nucleosides Nucleotides, 1997, 16, 1641–1643) with borate ester of 2-methoxy ethanol (FIG. 19). Compound 84 is silylated using 1,3-dichloro-1,1,3,3-tetraisopropyldisiloxane in pyridine which is further alkylated with 2-thiophenyl ethyliodide (prepared according to Anklam, E. et al. Helv. Chim. Acta, 1987, 70, 2110–2117) to give 85. Compound 85 is tritylated to give compound 86 followed by phosphitylation to give compound 87.

Example 19b

5'-O-DMT-2'-O-[2-(methoxy)ethyl]-5-[[2-(phenylthio)ethyl]oxo]uridine-3'-O-succinyl CPG (88)

Compound 86 (FIG. 18) is succinylated using succinic anhydride and DMAP in dichloroethane at 60° C. The succinyl derivative is coupled to CPG using 2-(1H-benzotriazole)-1-yl)-1,1,3,3-tetramethyluronium tetrafluoroborate and N-methylmorpholine in DMF to yield compound 88.

Example 20a

5'-O-DMT-2'-O-[2-(methoxy)ethyl]-5-[[2-(methylthio)ethyl]oxo]uridine-3'-[(2-cyanoethyl)-N,N-diisopropylphosphoramidite] (91)

Compound 84 is silylated using 1,3-dichloro-1,1,3,3-tetraisopropyldisiloxane in pyridine which is further alkylated with 2-thiomethyl ethyliodide (prepared according to the reported procedure Anklam, E. et. al. Helv. Chim. Acta, 1987, 70, 2110–2117) to give 89. Compound 89 is tritylated at the 5'-position to give compound 90 followed by phosphitylation to give compound 91.

Example 20b

5'-O-DMT-2'-O-[2-(methoxy)ethyl]-5-[[2-(phenylthio)ethyl]oxo]uridine-3'-O-succinyl CPG (92)

Compound 90 (FIG. 19) is converted into the 3'-O-succinyl derivative using succinic anhydride and DMAP in dichloroethane at 60° C. The succinyl derivative is coupled to amino alkyl CPG using 2-(1H-benzotriazole)-1-yl)1,1,3,3-tetramethyluronium tetrafluoroborate and N-methylmorpholine in DMF to yield compound 92.

Example 21a

N4-Benzoyl-5'-O-DMT-2'-O-[2-(methoxy)ethyl]-$N^2$-[2-(methanesulfinyl)ethyl]-2-aminoadenosine-3'-[(2-(cyanoethyl)-N,N-diisopropylphosphoramidite] (94)

Compound 73 is treated with CSO in $CH_3CN$ to yield the compound 93 (FIG. 20). Compound 93 is phosphitylated with N,N-diisopropylamine tetrazolide and 2-cyanoethyl-N,N,N'N'-tetraisopropylphosphoramidite in acetonitrile to yield compound 94.

Example 21b

N4-Benzoyl-5'-O-DMT-2'-O-[2-(methoxy)ethyl]-[$N^2$-[2-(methanesulfinyl)ethyl]-2-aminoadenosine-3'-O-succinyl CPG (95)

Compound 93 (FIG. 20) is succinylated using succinic anhydride and DMAP in dichloroethane at 60° C. The succinyl derivative is coupled to CPG using 2-(1H-benzotriazole)-1-yl)-1,1,3,3-tetramethyluronium tetrafluoroborate and N-methylmorpholine in DMF to yield the compound 95.

Example 22a

5'-O-DMT-2'-O-[2-(methoxy)ethyl]-5-[2-(methanesulfinyl)ethyl]aminouridine-3'-[(2-cyanoethyl)-N,N-diisopropylphosphoramidite](97)

Compound 69 is treated with CSO in $CH_3CN$ to yield compound 96 (FIG. 21). Compound 96 is phosphitylated with N,N-diisopropylamine tetrazolide and 2-cyanoethyl-N,N,N'N'-tetraisopropylphosphoramidite in acetonitrile to yield compound 97.

Example 22b

5'-O-DMT-2'-O-[2-(methoxy)ethyl]-5-[2-(methanesulfinyl)ethyl]aminouridine-3'-O-succinyl CPG (98)

Compound 96 (FIG. 21) is treated with succinic anhydride and DMAP in dichloroethane at 60° C. The succinyl derivative is coupled to CPG using 2-(1H-benzotriazole)-1-yl)-1,1,3,3-tetramethyluronium tetrafluoroborate and N-methylmorpholine in DMF to yield compound 98.

Example 23a

5'-O-DMT-2'-O-[2-(methoxy)ethyl]-5-[2-(methanesulfinyl)ethyl]oxouridine-3'-[(2-cyanoethyl)-N,N-diisopropylphosphoramidite] (100)

Compound 90 is treated with CSO in $CH_3CN$ to yield the compound 99. Compound 99 is phosphitylated with N,N-diisopropylamine tetrazolide and 2-cyanoethyl-N,N,N'N'-tetraisopropylphosphoramidite in acetonitrile to yield compound 100.

Example 23b

5'-O-DMT-2'-O-[2-(methoxy)ethyl]-5-[2-(methanesulfinyl)ethyl]oxouridine-3'-O-succinyl CPG (101)

Compound 99 (FIG. 22) is treated with succinic anhydride and DMAP in dichloroethane at 60° C. The succinyl derivative is coupled to CPG using 2-(1H-benzotriazole)-1-yl)-1,1,3,3-tetramethyluronium tetrafluoroborate and N-methylmorpholine in DMF to yield compound 101.

Example 24

5'-O-DMT-3'-O-[2-(methylthio)ethyl]-$N^6$-benzoyl-adenosine-2'-O-succinyl CPG (104)

Compound 21 is benzoylated with TMSCl, p-*yridine and benzoyl chloride to yield compound 102 (FIG. 23). Compound 102 is tritylated using DMTCl, DMAP and pyridine. The resulting compound 103 is treated with succinic anhydride and DMAP in dichloroethane at 60° C. The succinyl derivative is coupled to CPG using 2-(1H-benzotriazole)-1-yl)-1,1,3,3-tetramethyluronium tetrafluoroborate and N-methylmorpholine in DMF to give compound 104.

Example 25

5'-O-[2-(methylthio)ethyl]-2'-O-[2-(methylthio)ethyl]-5-methyluridine-3-[(2-cyanoethyl)-N,N-diisopropylphosphoramidite] (106)

Compound 2 is alkylated at the 5'-position with 2-(thiomethyl) ethyliodide in the presence of a base to give compound 105 (FIG. 24). Compound 105 is phosphitylated with N,N-diisopropylamine tetrazolide and 2-cyanoethyl-N,N,N'N'-tetraisopropylphosphoramidite to give compound 106.

Example 26
N-[2-(tert-Butyloxycarbonylamino)ethyl]-N-[5-[2-(methylthio)ethyl]urac-1-yl]acetylglycine (108)

Compound 107 was prepared according to a literature procedure (Rasmussen, H. et. al. Nature Struct. Biol, 1997, 4, 98–101). Compound 107 is treated with 2-thiomethyl ethylamine using triethyl amine and DMF to give compound 108.

Example 27
Synthesis of oligonucleotide containing 2'-O-(2-methanesulfinylethyl) modification using 2'-O-(2-methylthioethyl) Modified Amidite (D)

A solution of amidite D (0.1 M, in anhydrous acetonitrile) was used for the synthesis of the modified oligonucleotide. For incorporation of the D phosphoramidite a solution was delivered in two portions, each followed by a 5 minute coupling wait time. All other steps in the protocol supplied by Millipore were used without modification Oxidation of the internucleotide phosphite to phosphate was carried out using a 0.5 M solution of CSO in anhydrous acetonitrile. The 2'-O-(2-methylthioethyl) group was converted into 2'-O-(2-methanesulfinylethyl) group under these oxidation conditions with coupling efficiencies greater than 97%. After completion of the synthesis the CPG was suspended in aqueous ammonium hydroxide (30 wt. %) and kept at room temperature for 2 hours. The CPG was filtered the filtrate was heated at 55° C. for 6 hours to complete the removal of all protecting groups. The crude oligonucleotides were purified by HPLC (Waters, C-4, 7.8×300 mm, A=50 mM ammonium acetate, pH=7, B=acetonitrile, 5 to 60% B in 55 Min, Flow 2.5 mL min$^{-1}$, $\lambda$=260 nm). Detritylation with aqueous 80% acetic acid followed by desalting gave 2'-modified oligonucleotides. Oligonucleotides were analyzed by HPLC, CGE and mass spectroscopy.

2'-O-(2-methanesulfinylethyl) modified oligonucleotide

| | ES MS[#] | |
|---|---|---|
| SEQ ID NO.: 10 | Calcd | Found |
| 5' T*CC AGG T*GT* CCG CAT* C 3' | 5560.76 | 5561.06 |

T* = 2'-O-(2-methanesulfinylethyl)-5-methyluridine, [#]DMT on

Results and Discussion

There is an efficient scheme to synthesize the 2'-O-TME modified 5-methyluridine nucleoside A and the corresponding amidite B involving alkylation of the 2'-O-position. Alkylation of the 2'-O-position of a nucleoside using a five- or six-membered cyclic sulfate followed by nucleophilic displacement creates a modified nucleoside in only two or three synthetic steps. Treatment of the nucleoside A N-3-benzyloxymethyl-5-methyluridine with NaH in DMF at −45° C. followed by addition of the cyclic sulfate (1,3,2-dioxathiolane 2,2-dioxide) afforded the compound B in 63% yield. The selectivity for 2' over 3'-alkylation was about 3:1. The BOM group of the sulfate derivative B was removed via catalytic hydrogenation over a palladium hydroxide catalyst before nucleophilic displacement with NaSCH$_3$ to give compound C. Due to the stability of the sodium sulfate salt as a leaving group, subsequent nucleophilic displacement with sodium methylmercaptide required somewhat vigorous reaction conditions as reflux temperatures were needed to give the key intermediate D. In the alternate route, the N-3-BOM derivative of compound D was proved to be more difficult to deprotect due to poisoning of the palladium hydroxide catalyst by the sulfide side chain. The 5'-hydroxyl group of the crude compound D was converted to the DMT-protected compound (E) and subsequently converted to the 3'-phosphoramidite F in 63% yield. The nucleoside E was converted to the corresponding succinate and loaded onto controlled pore glass (CPG) to obtain the functionalized CPG H with 56 $\mu$mol/g loading capacity.

To synthesize the oligonucleotides, amidite F was dissolved in acetonitrile to afford a 0.1 M solution and loaded onto an Expedite DNA synthesizer. Coupling time was extended to 5 min and this step was carried out twice. Except for this modification, the standard protocols as specified for a Millipore Expedite Nucleic Acid Synthesis System were followed. Since thio ethers are sensitive to I$_2$/H$_2$O, the standard oxidizing agent used for oxidizing trivalent phosphorous was a 0.5 M solution of tert-BuOOH in acetonitrile. The oligonucleotides were deprotected with aqueous NH$_3$ at 55° C. and purified by HPLC on a C-4 column to afford the pure oligonucleotides in 95% full length purity by CGE analysis. All the oligonucleotides were characterized by HPLC and ES MS analysis (Table I).

TABLE I

Oligonucleotides containing 2'-O-[2-(methylthio)ethyl]- 5-methyluridine (T*) modifications

| SEQ. ID No.: | Sequence 5' to 3' | Mass Calc. | Mass Found | HPLC[a] Retention Time Min. |
|---|---|---|---|---|
| 1 | GCG T*T*T* T*T*T* T*T*T* T*GC G | 5778.34 | 5776.00 | 38.08 |
| 2 | CTC GTA CT*T* T*T*C CGG TCC | 5754.85 | 5752.8 | 31.43 |
| 2 | CTC GTA CT*T* T*T*C CGG TCC | 5194.38 | 5193.60 | 26.89 |
| 3 | TTT TTT TTT TTT TTT T*T*T* T* | 6080.09 | 9078.40 | 33.51 |

[a]Waters, C-4, 3.9 × 30 mm. A = 50 mm triethylammonium acetate, B = acetonitrile 5 to 60% B in 55 min., Flow 1.5 ml/min, $\lambda$ = 260 nm.

The binding affinity of 2'-O-MTE modified oligonucleotides to target RNA was determined by obtaining the tm values from the temperature dependent UV absorbency profile of the duplexes. The binding affinity of the modified oligonucleotides with 2'-O-(2-methylthioethyl)-RNA is similar to that of the 2'-O-(2-methoxyethyl) oligomers (Table II). This observed difference of 1.2° C./modification translates to a nearly 2° C. increase/modification when compared to the first generation 2'-deoxyphosphorothioate (2'-H/P=S) compounds. This is surprising considering that the sulfur atom is larger than oxygen and can cause steric hindrance in the RNA-antisense oligomer duplex that forms. Secondly, the sulfur atom should cause a weaker gauche effect than the oxygen atom, and the gauche effect has been used to explain the high binding affinity of the 2'-methoxyethyl group. While we do not wish to be bound by any particular theory, we presently believe the hydrophobicity of the sulfur causes water squeezing from the minor groove resulting in the observed stabilization.

TABLE II

Tm data for the oligonucleotides containing 2'-O-(2-methylthioethyl) modifications against complementary RNA

| SEQ. ID NO.: | Oligonucleotide Sequence5' to 3' | No. of Modifications | Tm (° C.) | Δ Tm (° C.) | Δ Tm (° C.) Modifications |
|---|---|---|---|---|---|
| 4 | GCG TTT TTT TTT TGC G | | 48.3 | | |
| 1 | GCG T*T*T* T*T*T* T*T*T* T*GC G | 10 | 60.1 | 11.8 | 1.18 |
| 5 | GCG TTT TTT TTT TGC G | 10 | 60.4$^a$ | 12.1$^a$ | 1.2$^a$ |
| 6 | CTC GTA CTT TTC CGG TCC | | 61.8 | | |
| 7 | CTC GTA CT*T* T*T*C* CGG TCC | 4 | 66.4 | 4.64 | 1.16 |
| 8 | CTC GTA CTT TTC CGG TCC | 4 | 65.3$^a$ | 3.5$^a$ | 0.9$^a$ |
| 9 | TCC AGG TGT CCG CAT C | | 62.3 | | |
| 10 | T*CC AGG T*GT* CCG CAT* C | 4 | 66.58 | 4.28 | 1.07 |
| 11 | T CC AGG T GT CCG CAT C | | 65.9$^a$ | 3.6$^a$ | 0.9$^a$ |

T* = 2'-O-(MTE)-5-methyluridine, T = 2'-O-MOE-5-methyluridine, $^a$Values from reference 2.

Binding of the 2'-O-MTE modified oligonucleotide SEQ ID NO.: 1 with human serum albumin was measured by ultrafiltration techniques. In these experiments 2'-O-methylthioethyl oligomer exhibited moderate protein binding even as a diester while the 2'-O-methoxyethyl oligomer showed no binding (Table III). The 2'-O-methylthioethyl oligomer exhibited weaker binding than 2'-deoxyphosphorothioate oligonucleotides. This moderate binding property of 2'-O-MTE is expected to improve the pharmacokinetic properties of the antisense drug compounds with this modification.

TABLE III $K_d$ values for the oligonucleotides SEQ. ID NO.: 1 5' GCG T*T*T* T*T*T* T*T*T* T*GC G 3' binding to human serum albumin

| SEQ ID NO.: | T* Chemistry | $K_d$ ($\mu$M) |
|---|---|---|
| 12 | full P = O, 2'-deoxy | No binding |
| 13 | P = O, 2'-O-MOE | No binding |
| 14 | P = O, 2'-O-MTE | 188 |
| 15 | fully P = S, 2'-deoxy | 30 |

In order to determine the nuclease resistance of this modification, oligonucleotide SEQ. ID NO.: 3 (Table I) was digested with Snake Venom Phosphodiesterase (SVPD). For comparison, oligonucleotides with the 2'-O-MOE modification in the same construct and 2'-deoxy analogs were also subjected to SVPD digestion under the same nuclease digestion conditions. The products of digestion at different time intervals were analyzed by capillary gel electrophoresis (CGE) and quantified. FIG. 28 shows the comparative nuclease resistance of these compounds. It was observed that the 2'-O-MTE modified oligonucleotide degraded much faster than the 2'-O-MOE modified oligonucleotide.

In conclusion, the 2'-O-MTE modified oligonucleotides exhibits enhanced protein binding relative to 2'-O-MOE-modified oligonucleotides. The enhanced protein binding is expected to help enhance the biodistribution of 2'-O-MTE phosphodiester oligomers.

We undertook structural studies to explain this difference. A decamer palindrome was synthesized incorporating 2'-O-MTE modification and its crystal structure was determined.

The same modification with 2'-O-MOE was studied and reported by Tereshko et al.

The decamer with 2'-O-MTE duplex exhibits a standard A-type geometry with all 2'-deoxyriboses and the ribose moieties from modified residues adopting typical C3'-endo puckers. The 2'-O-MTE substituent of residue T16 is well defined in electron density maps. Its geometry is very similar to that observed for a 2'-O-(2-methoxyethyl) (2'-O-MOE) substituent in the crystal structure of a decamer duplex with two incorporated 2'-O-MOE-modified thymidines. In both cases the conformation around the C—C bond of the central ethyl linker falls into a sc range. The torsion angles O2'-CA'-CB'-SC' and O2'-CA2'-CB'-OC' are −73° and −43° for the MTE and MOE substituents, respectively (substituent atoms are numbered alphabetically). As previously observed in crystal structures of nucleic acid duplexes bearing 2'-O-MOE modifications, the 2'-O-MTE substituent of residue T16 provides a binding site for a water molecule. This water forms hydrogen bonds to the 3'- and the 2'-oxygen atoms as well as to the sulfur atom of the MTE substituent. Unlike in the crystal structure of the decamer duplex containing single 2'-O-MOB modifications per strand, the TOE-substituent of residue T6 appears disordered. We cannot attribute the fact that we were unable to locate the substituent in the electron density maps to the limited resolution of the crystal structure. Rather, the 2'-O-MTE substituent may exhibit a lower degree of conformational preorganization compared with the 2'-O-MOE substituent. The particular hydration motif found for 2'-O-MOE-modified residues as well as the 2'-O-MTE-modified residue T16 in the present structure probably stabilizes their synclinal conformations. Moreover, the excellent nuclease resistance provided by the 2'-O-MOE modification may partly be due to the limited conformational flexibility of the substituent as well as the formation of a water network that spans substituent, sugar and phosphate group. The higher flexibility and subsequent lack of a stable water structure observed for one of the two 2'-O-MTE substitutes in our crystal structure may hint at possible origins of the more limited resistant to exonuclease degradation seen for the 2'-O-MTE modification relative to

What is claimed is:

1. A compound of formula II:

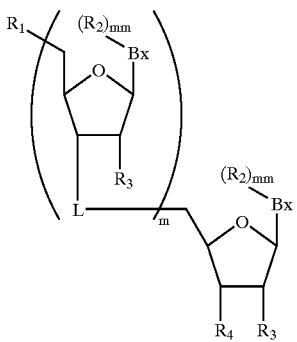

wherein:
- each Bx is an optionally protected heterocyclic base moiety;
- $R_1$ is hydrogen, hydroxyl, a protected hydroxyl, a nucleoside, a nucleotide, an oligonucleoside, an oligonucleotide or a group of formula I;
- $R_4$ is hydrogen, hydroxyl, a protected hydroxyl, a nucleoside, a nucleotide, an oligonucleoside, an oligonucleotide or a group of formula I;
- each $R_2$ is a group of formula I:

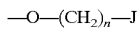

wherein:
- each n is, independently, from 1 to about 10;
- each J is, independently, a sulfonic acid (—S(=O)$_2$OH), a sulfonate salt (—S(=O)$_2$O$^-$X$^+$), a sulfoxide (—S(=O)—Z), a sulfone (—S(=O)$_2$—Z), —SH, —S—S—Z, or a thiol (—S—Z);
- each X$^+$ is a metal cation;
- each Z is, independently, selected from the group consisting of $C_1$–$C_{20}$ alkyl, $C_2$–$C_{20}$ alkenyl, $C_2$–$C_{20}$ alkynyl, $C_5$–$C_{20}$ aryl and $C_5$–$C_{20}$ aryl substituted $C_1$–$C_{20}$ alkyl;
- each $R_3$ is, independently, hydrogen, hydroxyl, a protected hydroxyl, an optionally protected sugar substituent group or a group of formula I;
- L is an internucleoside linking group;
- m is from 3 to about 50; and
- each mm is, independently, 0 or 1;
- wherein at least one of said L is other than a phosphodiester internucleoside linkage and at least one of said $R_1$, $R_2$ and $R_4$ is a group of formula I.

2. The compound of claim 1 wherein at least one $R_3$ is an optionally protected sugar substituent group.

3. The compound of claim 1 wherein at least two of said $R_1$, $R_2$, $R_3$, and $R_4$ are groups of formula I.

4. The compound of claim 3 wherein at least two of said $R_3$ are, independently, groups of formula I.

5. The compound of claim 1 wherein substantially all $R_3$ are groups of formula I.

6. The compound of claim 1 wherein $R_1$ is a group of formula I.

7. The compound of claim 1 wherein $R_4$ is a group of formula I.

8. The compound of claim 1 wherein J is —S—Z and Z is a straight or branched $C_1$ to $C_{20}$ alkyl group.

9. The compound of claim 8 wherein said alkyl group is methyl, ethyl or propyl.

10. The compound of claim 9 wherein said alkyl group is methyl.

11. The compound of claim 1 wherein J is —S—Z and Z is aryl having from 5 to about 14 carbon atoms.

12. The compound of claim 1 wherein Z is phenyl.

13. The compound of claim 1 wherein at least one J is a sulfonic acid.

14. The compound of claim 1 wherein at least one J is a sulfonate salt.

15. The compound of claim 14 wherein X$^+$ is Na$^+$.

16. The compound of claim 1 wherein at least one J is a sulfoxide.

17. The compound of claim 16 wherein Z is substituted or unsubstituted $C_1$–$C_{20}$ alkyl or substituted or unsubstituted $C_5$–$C_{20}$ aryl.

18. The compound of claim 1 wherein at least one J is a sulfone.

19. The compound of claim 18 wherein Z is substituted or unsubstituted $C_1$–$C_{20}$ alkyl or substituted or unsubstituted $C_5$–$C_{20}$ aryl.

20. The compound of claim 1 wherein said internucleoside linking group is a phosphorus-containing internucleoside linking group.

21. The compound of claim 20 wherein said internucleoside linking group is a phosphodiester, a phosphorothioate or a phosphorodithioate.

22. The compound of claim 1 wherein m is from about 8 to about 30.

23. The compound of claim 1 wherein m is from about 15 to about 25.

24. The compound of claim 1 wherein each mm is 0.

25. The compound of claim 1 wherein n is 2.

26. The compound of claim 1 wherein each of said Bx is independently selected from the group consisting of adenine, guanine, thymine, cytosine, uracil, 5-methylcytosine (5-me-C), 5-hydroxymethyl cytosine, xanthine, hypoxanthine, 2-aminoadenine, alkyl derivatives of adenine and guanine, 2-thiouracil, 2-thiothymine, 2-thiocytosine, 5-halouracil, 5-halocytosine, 5-propynyl uracil, 5-propynyl cytosine, 6-azo uracil, 6-azo cytosine, 6-azo thymine, 5-uracil (pseudouracil), 4-thiouracil, 8-substituted adenines and guanines, 5-substituted uracils and cytosines, 7-methylguanine, 7-methyladenine, 8-azaguanine, 8-azaadenine, 7-deazaguanine, 7-deazaadenine, 3-deazaguanine and 3-deazaadenine.

27. The compound of claim 1 wherein each optionally protected sugar substituent groups is, independently, $C_1$–$C_{20}$ alkyl, $C_2$–$C_{20}$ alkenyl, $C_2$–$C_{20}$ alkynyl, $C_5$–$C_{20}$ aryl, —O-alkyl, —O-alkenyl, —O-alkynyl, —O-alkylamino, —O-alkylalkoxy, —O-alkylaminoalkyl, —O-alkyl imidazole, —OH, —SH, —S-alkyl, —S-alkenyl, —S-alkynyl, —N(H)-alkyl, —N(H)-alkenyl, —N(H)-alkynyl, —N(alkyl)$_2$, —O-aryl, —S-aryl, —NH-aryl, —O-aralkyl, —S-aralkyl, —N(H)-aralkyl, phthalimido (attached at N), halogen, amino, keto (—C(=O)—R), carboxyl (—C(=O)OH), nitro (—NO$_2$), nitroso (—N=O), cyano (—CN), trifluoromethyl (—CF$_3$), trifluoromethoxy (—O—CF$_3$), imidazole, azido (—N$_3$), hydrazino (—N(H)—NH$_2$), aminooxy (—O—NH$_2$), isocyanato (—N=C=O), sulfoxide (—S(=O)—R), sulfone (—S(=O)$_2$—R), disulfide (—S—S—R), silyl, heterocycle, carbocycle, intercalator, reporter group, conjugate, polyamine, polyamide, polyalkylene glycol, and polyethers of the formula (—O-alkyl)$_m$, where m is 1 to about 10;

wherein each R is, independently, hydrogen, a protecting group or substituted or unsubstituted alkyl, alkenyl, or alkynyl wherein said substituted alkyl, alkenyl, or alkynyl are substituted with haloalkyl, alkenyl, alkoxy, thioalkoxy, haloalkoxy, aryl groups as well as halogen, hydroxyl, amino, azido, carboxy, cyano, nitro, mercapto, sulfides, sulfones, and sulfoxides;

or each sugar substituent group has one of formula VI or VII:

wherein:

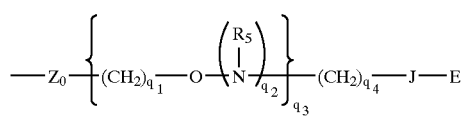

VI

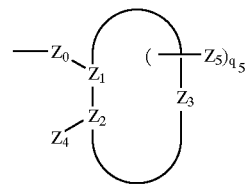

VII $Z_0$ is O, S or NH;

J is a single bond, O or C(=O);

E is $C_1$–$C_{10}$ alkyl, N(R$_5$)(R$_6$), N(R$_5$)(R$_7$), N=C(R$_{5a}$)(R$_{6a}$), N=C(R$_{5a}$)(R$_{7a}$) or has formula IX;

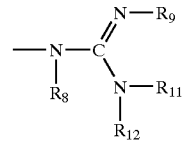

IX each R$_8$, R$_9$, R$_{11}$ and R$_{12}$ is, independently, hydrogen, C(O)R$_{13}$, substituted or unsubstituted $C_1$–$C_{10}$ alkyl, substituted or unsubstituted $C_2$–$C_{10}$ alkenyl, substituted or unsubstituted $C_2$–$C_{10}$ alkynyl, alkylsulfonyl, arylsulfonyl, a chemical functional group or a conjugate group, wherein the substituent groups are selected from hydroxyl, amino, alkoxy, carboxy, benzyl, phenyl, nitro, thiol, thioalkoxy, halogen, alkyl, aryl, alkenyl and alkynyl;

or optionally, R$_{11}$ and R$_{12}$, together form a phthalimido moiety with the nitrogen atom to which they are attached;

each R$_{13}$ is, independently, substituted or unsubstituted $C_1$–$C_{10}$ alkyl, trifluoromethyl, cyanoethyloxy, methoxy, ethoxy, t-butoxy, allyloxy, 9-fluorenylmethoxy, 2-(trimethylsilyl)-ethoxy, 2,2,2-trichloroethoxy, benzyloxy, butyryl, iso-butyryl, phenyl or aryl;

R$_5$ is hydrogen, a nitrogen protecting group or —T—L,

R$_{5a}$ is hydrogen, a nitrogen protecting group or —T—L,

T is a bond or a linking moiety;

L is a chemical functional group, a conjugate group or a solid support material;

each R$_6$ and R$_7$ is, independently, H, a nitrogen protecting group, substituted or unsubstituted $C_1$–$C_{10}$ alkyl, substituted or unsubstituted $C_2$–$C_{10}$ alkenyl, substituted or unsubstituted $C_2$–$C_{10}$ alkynyl, wherein said substitution is hydroxyl, amino, alkoxy, carboxy, benzyl, phenyl, nitro, thiol, thioalkoxy, halogen, alkyl, aryl, alkenyl, alkynyl; NH$_3^+$, N(R$_{14}$)(R$_{15}$), guanidino or acyl where said acyl is an acid amide or an ester;

or R$_6$ and R$_7$, together, are a nitrogen protecting group, are joined in a ring structure that optionally includes an additional heteroatom selected from N and O or are a chemical functional group;

each R$_{14}$ and R$_{15}$ is, independently, H, $C_1$–$C_{10}$ alkyl, a nitrogen protecting group, or R$_{14}$ and R$_{15}$, together, are a nitrogen protecting group;

or R$_{14}$ and R$_{15}$ are joined in a ring structure that optionally includes an additional heteroatom selected from N and O;

$Z_4$ is OX, SX or $N(X)_2$;

each X is, independently, H, $C_1$–$C_8$ alkyl, $C_1$–$C_8$ haloalkyl, $C(=NH)N(H)R_{16}$, $C(=O)N(H)R_{16}$ or $OC(=O)N(H)R_{16}$;

$R_{16}$ is H or $C_1$–$C_8$ alkyl;

$Z_1$, $Z_2$ and $Z_3$ comprise a ring system having from about 4 to about 7 carbon atoms or having from about 3 to about 6 carbon atoms and 1 or 2 heteroatoms wherein said heteroatoms are selected from oxygen, nitrogen and sulfur and wherein said ring system is aliphatic, unsaturated aliphatic, aromatic, or saturated or unsaturated heterocyclic;

$Z_5$ is alkyl or haloalkyl having 1 to about 10 carbon atoms, alkenyl having 2 to about 10 carbon atoms, alkynyl having 2 to about 10 carbon atoms, aryl having 6 to about 14 carbon atoms, $N(R_5)(R_6)$ $OR_5$, halo, $SR_5$ or CN;

each $q_1$ is, independently, an integer from 1 to 10;

each $q_2$ is, independently, 0 or 1;

$q_3$ is 0 or an integer from 1 to 10;

$q_4$ is an integer from 1 to 10;

$q_5$ is from 0, 1 or 2; and provided that when $q_3$ is 0, $q_4$ is greater than 1.

28. A compound of formula II:

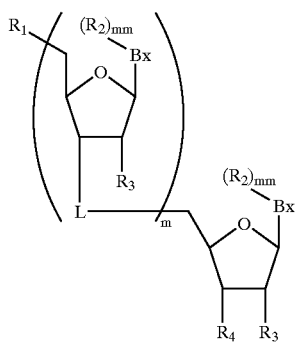

(II)

wherein:

each Bx is an optionally protected heterocyclic base moiety;

$R_1$ is hydrogen, hydroxyl, a protected hydroxyl, a nucleoside, a nucleotide, an oligonucleotide, an oligonucleotide or a group of formula I;

$R_4$ is hydrogen, hydroxyl, a protected hydroxyl, a nucleoside, a nucleotide, an oligonucleotide, an oligonucleotide or a group of formula I;

each $R_2$ is a group of formula 1:

$$—O—(CH_2)_n—J \qquad (I)$$

wherein:

each n is, independently, from 1 to about 10;

each J is, independently, a sulfonic acid ($—S(=O)_2OH$), a sulfonate salt ($—S(=O)_2O^-X^+$), a sulfoxide ($—S(=O)—Z$), a sulfone ($—S(=O)_2—Z$), $—SH$, $—S—S—Z$, or a thiol ($—S—Z$);

each $X^+$ is a metal cation;

each Z is, independently, selected from the group consisting of $C_1$–$C_{20}$ alkyl, $C_2$–$C_{20}$ alkenyl, $C_2$–$C_{20}$ alkynyl, $C_5$–$C_{20}$ aryl and $C_5$—$C_{20}$ aryl substituted $C_1$–$C_{20}$ alkyl;

each $R_3$ is, independently, hydrogen, hydroxyl, a protected hydroxyl, an optionally protected sugar substituent group or a group of formula I;

L is an internucleoside linking group;

m is from 3 to about 50; and each mm is, independently, 0 or 1;

wherein at least one of said L is other than a phosphodiester internucleoside linkage and at least two of said $R_1$, $R_2$, $R_3$ and $R_4$ are groups of formula I.

* * * * *

UNITED STATES PATENT AND TRADEMARK OFFICE
CERTIFICATE OF CORRECTION

PATENT NO.    : 6,921,812 B1
DATED         : July 26, 2005
INVENTOR(S)   : Thazha P. Prakash et al.

It is certified that error appears in the above-identified patent and that said Letters Patent is hereby corrected as shown below:

Column 66,
Lines 7 and 10, delete "oligonucleotide" and insert -- oligonucleoside --.

Signed and Sealed this

Thirteenth Day of June, 2006

JON W. DUDAS
*Director of the United States Patent and Trademark Office*

SEQUENCE LISTING

<160> NUMBER OF SEQ ID NOS: 15

<210> SEQ ID NO 1
<211> LENGTH: 16
<212> TYPE: DNA
<213> ORGANISM: Artificial Sequence
<220> FEATURE:
<223> OTHER INFORMATION: Primer Oligonucleotide
<220> FEATURE:
<221> NAME/KEY: misc_feature
<222> LOCATION: (4)..(13)
<223> OTHER INFORMATION: 2'-O-[2-methylthio)ethyl]-5-methyluridine

<400> SEQUENCE: 1
gcgttttttt tttgcg                                               16

<210> SEQ ID NO 2
<211> LENGTH: 18
<212> TYPE: DNA
<213> ORGANISM: Artificial Sequence
<220> FEATURE:
<223> OTHER INFORMATION: Primer Oligonucleotide
<220> FEATURE:
<221> NAME/KEY: misc_feature
<222> LOCATION: (8)..(11)
<223> OTHER INFORMATION: 2'-O-[2-methylthio)ethyl]-5-methyluridine

<400> SEQUENCE: 2 ctcgtactttt tccggtcc                                            18

<210> SEQ ID NO 3
<211> LENGTH: 19
<212> TYPE: DNA
<213> ORGANISM: Artificial Sequence
<220> FEATURE:
<223> OTHER INFORMATION: Primer Oligonucleotide
<220> FEATURE:
<221> NAME/KEY: misc_feature
<222> LOCATION: (16)..(19)
<223> OTHER INFORMATION: 2'-O-[2-(methylthio)ethyl]-5-methyluridine

<400> SEQUENCE: 3
tttttttttt tttttttt                                             19

<210> SEQ ID NO 4
<211> LENGTH: 16
<212> TYPE: DNA
<213> ORGANISM: Artificial Sequence
<220> FEATURE:
<223> OTHER INFORMATION: Primer Oligonucleotide
<220> FEATURE:
<221> NAME/KEY: misc_feature
<222> LOCATION: (16)..(19)
<223> OTHER INFORMATION: 2'-O-[2-(methylthio)ethyl]-5-methyluridine

<400> SEQUENCE: 4
gcgttttttt tttgcg                                               16

<210> SEQ ID NO 5
<211> LENGTH: 16
<212> TYPE: DNA
<213> ORGANISM: Artificial Sequence
<220> FEATURE:
<223> OTHER INFORMATION: Primer Oligonucleotide
<220> FEATURE:
<221> NAME/KEY: misc_feature
<222> LOCATION: (4)..(13)
<223> OTHER INFORMATION: 2'-O-MOE-5-methyluridine -continued

```
<400> SEQUENCE: 5
gcgttttttt tttgcg                                              16

<210> SEQ ID NO 6
<211> LENGTH: 18
<212> TYPE: DNA
<213> ORGANISM: Artificial Sequence
<220> FEATURE:
<223> OTHER INFORMATION: Primer Oligonucleotide

<400> SEQUENCE: 6
ctcgtacttt tccggtcc                                            18

<210> SEQ ID NO 7
<211> LENGTH: 18
<212> TYPE: DNA
<213> ORGANISM: Artificial Sequence
<220> FEATURE:
<223> OTHER INFORMATION: Primer Oligonucleotide
<220> FEATURE:
<221> NAME/KEY: misc_feature
<222> LOCATION: (8)..(12)
<223> OTHER INFORMATION: 2'-O-(MTE)-5-methyluridine

<400> SEQUENCE: 7
ctcgtacttt tccggtcc                                            18

<210> SEQ ID NO 8
<211> LENGTH: 18
<212> TYPE: DNA
<213> ORGANISM: Artificial Sequence
<220> FEATURE:
<223> OTHER INFORMATION: Primer Oligonucleotide
<220> FEATURE:
<221> NAME/KEY: misc_feature
<222> LOCATION: (8)..(11)
<223> OTHER INFORMATION: 2'-O-(MOE)-5-methyluridine

<400> SEQUENCE: 8
ctcgtacttt tccggtcc                                            18

<210> SEQ ID NO 9
<211> LENGTH: 16
<212> TYPE: DNA
<213> ORGANISM: Artificial Sequence
<220> FEATURE:
<223> OTHER INFORMATION: Primer Oligonucleotide

<400> SEQUENCE: 9
tccaggtgtc cgcatc                                              16

<210> SEQ ID NO 10
<211> LENGTH: 16
<212> TYPE: DNA
<213> ORGANISM: Artificial Sequence
<220> FEATURE:
<223> OTHER INFORMATION: Primer Oligonucleotide
<220> FEATURE:
<221> NAME/KEY: misc_feature
<222> LOCATION: (1)..(1)
<223> OTHER INFORMATION: 2'-O-(MTE)-5-methyluridine
<220> FEATURE:
<221> NAME/KEY: misc_feature
<222> LOCATION: (7)..(7)
<223> OTHER INFORMATION: 2'-O-(MTE)-5-methyluridine
<220> FEATURE:
<221> NAME/KEY: misc_feature
<222> LOCATION: (9)..(9)
```

```
<223> OTHER INFORMATION: 2'-O-(MTE)-5-methyluridine
<220> FEATURE:
<221> NAME/KEY: misc_feature
<222> LOCATION: (15)..(15)
<223> OTHER INFORMATION: 2'-O-(MTE)-5-methyluridine

<400> SEQUENCE: 10
tccaggtgtc cgcatc                                                      16

<210> SEQ ID NO 11
<211> LENGTH: 16
<212> TYPE: DNA
<213> ORGANISM: Artificial Sequence
<220> FEATURE:
<223> OTHER INFORMATION: Primer Oligonucleotide
<220> FEATURE:
<221> NAME/KEY: misc_feature
<222> LOCATION: (1)..(1)
<223> OTHER INFORMATION: 2'-O-MOE-5-methyluridine
<220> FEATURE:
<221> NAME/KEY: misc_feature
<222> LOCATION: (7)..(7)
<223> OTHER INFORMATION: 2'-O-MOE-5-methyluridine
<220> FEATURE:
<221> NAME/KEY: misc_feature
<222> LOCATION: (9)..(9)
<223> OTHER INFORMATION: 2'-O-MOE-5-methyluridine
<220> FEATURE:
<221> NAME/KEY: misc_feature
<222> LOCATION: (15)..(15)
<223> OTHER INFORMATION: 2'-O-MOE-5-methyluridine

<400> SEQUENCE: 11
tccaggtgtc cgcatc                                                      16

<210> SEQ ID NO 12
<211> LENGTH: 16
<212> TYPE: DNA
<213> ORGANISM: Artificial Sequence
<220> FEATURE:
<223> OTHER INFORMATION: Primer Oligonucleotide
<220> FEATURE:
<221> NAME/KEY: misc_feature
<222> LOCATION: (4)..(13)
<223> OTHER INFORMATION: P=O; 2'-deoxy

<400> SEQUENCE: 12
gcgttttttt tttgcg                                                      16

<210> SEQ ID NO 13
<211> LENGTH: 16
<212> TYPE: DNA
<213> ORGANISM: Artificial Sequence
<220> FEATURE:
<223> OTHER INFORMATION: Primer Oligonucleotide
<220> FEATURE:
<221> NAME/KEY: misc_feature
<222> LOCATION: (4)..(13)
<223> OTHER INFORMATION: P=O; 2'-O-MOE

<400> SEQUENCE: 13
gcgttttttt tttgcg                                                      16

<210> SEQ ID NO 14
<211> LENGTH: 16
<212> TYPE: DNA
<213> ORGANISM: Artificial Sequence
<220> FEATURE:
<223> OTHER INFORMATION: Primer Oligonucleotide
<220> FEATURE:
<221> NAME/KEY: misc_feature
```

```
<222> LOCATION: (4)..(13)
<223> OTHER INFORMATION: P=O; 2'-O-MTE

<400> SEQUENCE: 14 gcgtttttttt tttgcg                                              16

<210> SEQ ID NO 15
<211> LENGTH: 16
<212> TYPE: DNA
<213> ORGANISM: Artificial Sequence
<220> FEATURE:
<223> OTHER INFORMATION: Primer Oligonucleotide
<220> FEATURE:
<221> NAME/KEY: misc_feature
<222> LOCATION: (4)..(13)
<223> OTHER INFORMATION: P=S; 2'-deoxy

<400> SEQUENCE: 15 gcgtttttttt tttgcg                                              16
```